US012735478B2

(12) United States Patent
Hosen et al.

(10) Patent No.: US 12,735,478 B2
(45) Date of Patent: Sep. 15, 2026

(54) ANTI-CD98HC ANTIBODY

(71) Applicant: OSAKA UNIVERSITY, Osaka (JP)

(72) Inventors: Naoki Hosen, Osaka (JP); Haruo Sugiyama, Osaka (JP); Atsushi Kumanogoh, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

(21) Appl. No.: 18/356,489

(22) Filed: Jul. 21, 2023

(65) Prior Publication Data

US 2023/0357390 A1 Nov. 9, 2023

Related U.S. Application Data

(63) Continuation of application No. 17/527,681, filed on Nov. 16, 2021, now abandoned, which is a continuation of application No. 15/751,717, filed as application No. PCT/JP2016/073503 on Aug. 9, 2016, now abandoned.

(30) Foreign Application Priority Data

Aug. 10, 2015 (JP) ................................ 2015-158414

(51) Int. Cl.

| | |
|---|---|
| ***C07K 16/28*** | (2006.01) |
| ***A61K 38/17*** | (2006.01) |
| ***A61K 39/00*** | (2006.01) |
| ***A61P 35/00*** | (2006.01) |
| ***C07K 16/30*** | (2006.01) |
| ***C07K 19/00*** | (2006.01) |
| ***C12N 15/62*** | (2006.01) |

(52) U.S. Cl.

CPC ............. *C07K 16/28* (2013.01); *A61P 35/00* (2018.01); *C07K 16/2896* (2013.01); *C07K 16/3061* (2013.01); *C07K 19/00* (2013.01); *C12N 15/62* (2013.01); *A61K 38/1709* (2013.01); *A61K 2039/505* (2013.01); *C07K 2317/33* (2013.01); *C07K 2317/34* (2013.01); *C07K 2317/565* (2013.01); *C07K 2317/732* (2013.01); *C07K 2317/734* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 7,438,908 | B2 * | 10/2008 | De Santis | C07K 16/18 435/7.1 |
| 9,676,850 | B2 * | 6/2017 | Saunders | A61K 47/6849 |
| 2003/0017516 | A1 | 1/2003 | Herman | |
| 2009/0041719 | A1 | 2/2009 | Ishibashi | |
| 2010/0143367 | A1 | 6/2010 | Tahara et al. | |
| 2011/0280884 | A1 | 11/2011 | Tahara et al. | |
| 2012/0045446 | A1 | 2/2012 | Hosen et al. | |
| 2013/0052197 | A1 | 2/2013 | Yasutomo | |
| 2015/0307621 | A1 | 10/2015 | Tahara et al. | |

FOREIGN PATENT DOCUMENTS

| | | |
|---|---|---|
| EP | 3336185 | 6/2018 |
| JP | 5566374 | 9/2011 |
| JP | 2012-145500 | 8/2012 |
| JP | 2015-501639 | 1/2015 |
| WO | 2007/114496 | 10/2007 |
| WO | 2008/017828 | 2/2008 |
| WO | 2011/118804 | 9/2011 |
| WO | 2013/078377 | 5/2013 |

OTHER PUBLICATIONS

Nawashiro et al., "The Role of CD98 in Astrocytic Neoplasms", Human Cell, 15(1): 25-31 (2002).

Lonial et al., "Elotuzumab in Combination With Lenalidomide and Low-Dose Dexamethasone in Relapsed or Refractory Multiple Myeloma", Journal of Clinical Oncology, 30(16): 1953-1959 (2012).

De Weers et al., "Daratumumab, a Novel Therapeutic Human CD38 Monoclonal Antibody, Induces Killing of Multiple Myeloma and Other Hematological Tumors", The Journal of Immunology, 186(3): 1840-1848 (2011).

Zhao et al., "A Herceptin-Based Chimeric Antigen Receptor with Modified Signaling Domains Leads to Enhanced Survival of Transduced T Lymphocytes and Antitumor Activity", The Journal of Immunology, 183(9): 5563-5574 (2009).

Maude et al., "Chimeric Antigen Receptor T Cells for Sustained Remissions in Leukemia", N Engl J Med., 371(16): 1507-1517 (2014).

Maher et al., "Human T-lymphocyte cytotoxicity and proliferation directed by a single chimeric TCRζ/CD28 receptor", Nature Biotechnology, 20(1): 70-75 (2002).

English language translation of the International Search Report, issued Sep. 27, 2016 in corresponding International Patent Application No. PCT/JP2016/073503.

Paul (Fundamental Immunology, 3rd Edition, 1993, pp. 292-295) (Year: 1993).

Bendig M. M. (Methods: A Companion to Methods in Enzymology, 1995, 8:83-93) (Year: 1995).

Rudikoff et al. (Proceedings of the National Academy of Sciences USA, vol. 79, p. 1979-1983, 1982) (Year: 1982).

Johnson and Wu (Methods in Molecular Biology, Antibody Engineering: Methods and Protocols, vol. 248, p. 11-25, 2004) (Year: 2004).

(Continued)

*Primary Examiner* — Robert A Wax
*Assistant Examiner* — Julia A Rossi
(74) *Attorney, Agent, or Firm* — Wenderoth, Lind & Ponack, L.L.P.

(57) ABSTRACT

Provided is an antibody effective in treating tumors and the like. The antibody recognizes an epitope that contains an N-glycosylation site of human CD98 hc and that is exposed by inhibiting N-linked glycosylation.

8 Claims, 21 Drawing Sheets

Specification includes a Sequence Listing.

(56) References Cited

OTHER PUBLICATIONS

Extended European Search Report issued Mar. 30, 2022 in corresponding European Patent Application No. 21203138.9.
Itoh, K. et al., "Identification of cell proliferation-associated epitope on CD98 oncoprotein using phage display random peptide library", Cancer Science, vol. 98, No. 11, pp. 1696-1700, Nov. 2007.
Hayes, G.M. et al., "Antitumor activity of an anti-CD98 antibody", International Journal of Cancer, vol. 137, No. 3, pp. 710-720, Aug. 2015.
Powlesland, A.S. et al., "Targeted glycoproteomic identification of cancer cell glycosylation" Glycobiology, vol. 19, No. 8, pp. 899-909, May 2009.
Dubel (Handbook of Therapeutic Antibodies, 2007, p. 100-101) (Year: 2007).

* cited by examiner

A
MM1s
Bortezomib
0nM
10nM
R8H283
:Isotype control
:R8H283
B
Bortezomib
0nM
2nM
MM
1.1%
0.84%
CD38
CD138
T
CD19
CD3
MM
T
R8H283
MM
T
MEM108
:Isotype control
:R8H283/MEM-108

A
R8H283 or mIgG
Tumor volumes (mm3)
control mIgG (10mg/kg)
R8H283 (10mg/kg)
Days after start of the treatment
B
Control mIgG
R8H283
C
R8H283 or mIgG
Tumor volumes (mm3)
mIgG (1mg/kg)
R8H283 (1mg/kg)
Days after start of the treatment hMMSC2
mMMSC2
I371L
D374/ A375Q
A376G
D391N/ F395I/ P396F/ D397H
F395I/ P396F/ D397H
G4001R/ A401P
A404L
R8H283
:Isotype control
:R8H283
MFI
20
15
10
5
0
hCD98hc
mCD98hc
I371L
D374/A375Q
A376G
D391N/F395I/P396F/D397H
FPD395/6/7IFH
G400R/A401P
A404L

SEQUENCE LISTING

```
Sequence total quantity: 57
SEQ ID NO: 1           moltype = AA  length = 4
FEATURE                Location/Qualifiers
REGION                 1..4
                       note = VH CDR1 of R8H283 antibody
source                 1..4
                       mol_type = protein
                       organism = synthetic construct
SEQUENCE: 1
GFTF                                                                4

SEQ ID NO: 2           moltype = AA  length = 10
FEATURE                Location/Qualifiers
REGION                 1..10
                       note = VH CDR2 of R8H283 antibody
source                 1..10
                       mol_type = protein
                       organism = synthetic construct
SEQUENCE: 2
IRLKSNNYAT                                                          10

SEQ ID NO: 3           moltype = AA  length = 8
FEATURE                Location/Qualifiers
REGION                 1..8
                       note = VH CDR3 of R8H283 antibody
source                 1..8
                       mol_type = protein
                       organism = synthetic construct
SEQUENCE: 3
SRLPSFDY                                                            8

SEQ ID NO: 4           moltype = AA  length = 106
```

```
FEATURE                Location/Qualifiers
REGION                 1..106
                       note = VH of R8H283 antibody
source                 1..106
                       mol_type = protein
                       organism = synthetic construct
SEQUENCE: 4
EVKLEESGGG LVQPGGSMKL SCVASGFTFS NYWMNWVRQS PEKGLEWVAE IRLKSNNYAT  60
HYAESVKGRF TISRDDSKSS VYLQMNNLRA EDTGIYYCSR LPSFDY                106

SEQ ID NO: 5           moltype = AA  length = 436
FEATURE                Location/Qualifiers
REGION                 1..436
                       note = Heavy chain of R8H283 antibody
source                 1..436
                       mol_type = protein
                       organism = synthetic construct
SEQUENCE: 5
EVKLEESGGG LVQPGGSMKL SCVASGFTFS NYWMNWVRQS PEKGLEWVAE IRLKSNNYAT  60
HYAESVKGRF TISRDDSKSS VYLQMNNLRA EDTGIYYCSR LPSFDYAKTT APSVYPLAPV  120
CGDTTGSSVT LGCLVKGYFP EPVTLTWNSG SLSSGVHTFP AVLQSDLYTL SSSVTVTSST  180
WPSQSITCNV AHPASSTKVD KKIEPRGPTI KPCPPCKCPA PNLLGGPSVF IFPPKIKDVL  240
MISLSPIVTC VVVDVSEDDP DVQISWFVNN VEVHTAQTQT HREDYNSTLR VVSALPIQHQ  300
DWMSGKEFKC KVNNKDLPAP IERTISKPKG SVRAPQVYVL PPPEEEMTKK QVTLTCMVTD  360
FMPEDIYVEW TNNGKTELNY KNTEPVLDSD GSYFMYSKLR VEKKNWVERN SYSCSVVHEG  420
LHNHHTTKSF SRTPGK                                                 436

SEQ ID NO: 6           moltype = AA  length = 11
FEATURE                Location/Qualifiers
REGION                 1..11
                       note = VL CDR1 of R8H283 antibody
source                 1..11
                       mol_type = protein
                       organism = synthetic construct
SEQUENCE: 6
KSLLHSNGNT Y                                                      11

SEQ ID NO: 7           moltype =   length =
SEQUENCE: 7
000

SEQ ID NO: 8           moltype = AA  length = 9
FEATURE                Location/Qualifiers
REGION                 1..9
                       note = VL CDR3 of R8H283 antibody
source                 1..9
                       mol_type = protein
                       organism = synthetic construct
SEQUENCE: 8
MQHLEYPFT                                                         9

SEQ ID NO: 9           moltype = AA  length = 132
FEATURE                Location/Qualifiers
REGION                 1..132
                       note = VL of R8H283 antibody
source                 1..132
                       mol_type = protein
                       organism = synthetic construct
SEQUENCE: 9
MRCLAEFLGL LVLWIPGAIG DIVMTQAAPS VPVTPGESVS ISCRSTKSLL HSNGNTYLYW  60
FLQRPGQSPQ LLIYRMSNLA SGVPDRFSGS GSGTAFTLRI TRVEAEDVGI YYCMQHLEYP  120
FTFGAGTKLE LK                                                     132

SEQ ID NO: 10          moltype = AA  length = 238
FEATURE                Location/Qualifiers
REGION                 1..238
                       note = Light chain of R8H283 antibody
source                 1..238
                       mol_type = protein
                       organism = synthetic construct
SEQUENCE: 10
MRCLAEFLGL LVLWIPGAIG DIVMTQAAPS VPVTPGESVS ISCRSTKSLL HSNGNTYLYW  60
FLQRPGQSPQ LLIYRMSNLA SGVPDRFSGS GSGTAFTLRI TRVEAEDVGI YYCMQHLEYP  120
FTFGAGTKLE LKADAAPTVS IFPPSSEQLT SGGASVVCFL NNFYPKDINV KWKIDGSERQ  180
NGVLNSWTDQ DSKDSTYSMS STLTLTKDEY ERHNSYTCEA THKTSTSPIV KSFNRNEC    238

SEQ ID NO: 11          moltype = DNA  length = 12
FEATURE                Location/Qualifiers
misc_feature           1..12
```

```
                        note = VH CDR1 of R8H283 antibody
source                  1..12
                        mol_type = other DNA
                        organism = synthetic construct
SEQUENCE: 11
ggattcactt tc                                                      12

SEQ ID NO: 12           moltype = DNA  length = 30
FEATURE                 Location/Qualifiers
misc_feature            1..30
                        note = VH CDR2 of R8H283 antibody
source                  1..30
                        mol_type = other DNA
                        organism = synthetic construct
SEQUENCE: 12
attagattga aatctaataa ttatgcaaca                                   30

SEQ ID NO: 13           moltype = DNA  length = 24
FEATURE                 Location/Qualifiers
misc_feature            1..24
                        note = VH CDR3 of R8H283 antibody
source                  1..24
                        mol_type = other DNA
                        organism = synthetic construct
SEQUENCE: 13
tccagactcc cgtcctttga ctac                                         24

SEQ ID NO: 14           moltype = DNA  length = 318
FEATURE                 Location/Qualifiers
misc_feature            1..318
                        note = VH of R8H283 antibody
source                  1..318
                        mol_type = other DNA
                        organism = synthetic construct
SEQUENCE: 14
gaagtgaagc ttgaggagtc tggaggaggc ttggtgcaac ctggaggatc catgaaactc  60
tcctgtgttg cctctggatt cactttcagt aattactgga tgaactgggt ccgccagtct  120
ccagagaagg ggcttgagtg ggttgctgaa attagattga aatctaataa ttatgcaaca  180
cattatgcgg agtctgtgaa agggaggttc accatctcaa gagatgattc caaaagtagt  240
gtctacctgc aaatgaacaa cttaagagct gaagacactg gcatttatta ctgttccaga  300
ctcccgtcct ttgactac                                                318

SEQ ID NO: 15           moltype = DNA  length = 1308
FEATURE                 Location/Qualifiers
misc_feature            1..1308
                        note = Heavy chain of R8H283 antibody
source                  1..1308
                        mol_type = other DNA
                        organism = synthetic construct
SEQUENCE: 15
gaagtgaagc ttgaggagtc tggaggaggc ttggtgcaac ctggaggatc catgaaactc  60
tcctgtgttg cctctggatt cactttcagt aattactgga tgaactgggt ccgccagtct  120
ccagagaagg ggcttgagtg ggttgctgaa attagattga aatctaataa ttatgcaaca  180
cattatgcgg agtctgtgaa agggaggttc accatctcaa gagatgattc caaaagtagt  240
gtctacctgc aaatgaacaa cttaagagct gaagacactg gcatttatta ctgttccaga  300
ctcccgtcct ttgactacgc taaaacaaca gccccatcgg tctatccact ggcccctgtg  360
tgtggagata caactggctc ctcggtgact ctaggatgcc tggtcaaggg ttatttccct  420
gagccagtga ccttgacctg gaactctgga tccctgtcca gtggtgtgca caccttccca  480
gctgtcctgc agtctgacct ctacaccctc agcagctcag tgactgtaac ctcgagcacc  540
tggcccagcc agtccatcac ctgcaatgtg gcccacccgg caagcagcac caaggtggac  600
aagaaaattg agcccagagg gcccacaatc aagccctgtc ctccatgcaa atgcccagca  660
cctaacctct tgggtggacc atccgtcttc atcttccctc caaagatcaa ggatgtactc  720
atgatctccc tgagccccat agtcacatgt gtggtggtgg atgtgagcga ggatgaccca  780
gatgtccaga tcagctggtt tgtgaacaac gtggaagtac acacagctca gacacaaacc  840
catagagagg attacaacag tactctccgg gtggtcagtg ccctccccat ccagcaccag  900
gactggatga gtggcaagga gttcaaatgc aaggtcaaca acaaagacct cccagcgccc  960
atcgagagaa ccatctcaaa acccaaaggg tcagtaagag ctccacaggt atatgtcttg  1020
cctccaccag aagaagagat gactaagaaa caggtcactc tgacctgcat ggtcacagac  1080
ttcatgcctg aagacattta cgtggagtgg accaacaacg ggaaaacaga gctaaactac  1140
aagaacactg aaccagtcct ggactctgat ggttcttact tcatgtacag caagctgaga  1200
gtggaaaaga agaactgggt ggaaagaaat agctactcct gttcagtggt ccacgagggt  1260
ctgcacaatc accacacgac taagagcttc tcccggactc cgggtaaa               1308

SEQ ID NO: 16           moltype = DNA  length = 33
FEATURE                 Location/Qualifiers
misc_feature            1..33
                        note = VL CDR1 of R8H283 antibody
source                  1..33
                        mol_type = other DNA
```

```
                        organism = synthetic construct
SEQUENCE: 16
aagagtctcc tgcatagtaa tggcaacact tac                          33

SEQ ID NO: 17           moltype =   length =
SEQUENCE: 17
000

SEQ ID NO: 18           moltype = DNA  length = 27
FEATURE                 Location/Qualifiers
misc_feature            1..27
                        note = VL CDR3 of R8H283 antibody
source                  1..27
                        mol_type = other DNA
                        organism = synthetic construct
SEQUENCE: 18
atgcaacatc tagaatatcc tttcacg                                 27

SEQ ID NO: 19           moltype = DNA  length = 435
FEATURE                 Location/Qualifiers
misc_feature            1..435
                        note = Variable Light chain of R8H283 antibody
source                  1..435
                        mol_type = other DNA
                        organism = synthetic construct
SEQUENCE: 19
aaggggactc aagacttttt gtatcaagtt ctcagaatga ggtgcctagc tgagttcctg  60
gggctgcttg tgctctggat ccctggagcc attggggata ttgtgatgac tcaggctgca  120
ccctctgtac ctgtcactcc tggagagtca gtatccatct cctgcaggtc tactaagagt  180
ctcctgcata gtaatggcaa cacttacttg tattggttcc tgcagaggcc aggccagtct  240
cctcagctcc tgatatatcg gatgtccaac cttgcctcag gagtcccaga caggttcagt  300
ggcagtgggt caggaactgc tttcacactg agaatcacta gagtggaggc tgaggatgtg  360
ggtatttatt actgtatgca acatctagaa tatcctttca cgttcggtgc tgggaccaag  420
ctggagctga aacgg                                              435

SEQ ID NO: 20           moltype = DNA  length = 753
FEATURE                 Location/Qualifiers
misc_feature            1..753
                        note = Light chain of R8H283 antibody
source                  1..753
                        mol_type = other DNA
                        organism = synthetic construct
SEQUENCE: 20
aaggggactc aagacttttt gtatcaagtt ctcagaatga ggtgcctagc tgagttcctg  60
gggctgcttg tgctctggat ccctggagcc attggggata ttgtgatgac tcaggctgca  120
ccctctgtac ctgtcactcc tggagagtca gtatccatct cctgcaggtc tactaagagt  180
ctcctgcata gtaatggcaa cacttacttg tattggttcc tgcagaggcc aggccagtct  240
cctcagctcc tgatatatcg gatgtccaac cttgcctcag gagtcccaga caggttcagt  300
ggcagtgggt caggaactgc tttcacactg agaatcacta gagtggaggc tgaggatgtg  360
ggtatttatt actgtatgca acatctagaa tatcctttca cgttcggtgc tgggaccaag  420
ctggagctga aacgggcaga tgctgcacca actgtatcca tcttcccacc atccagtgag  480
cagttaacat ctggaggtgc ctcagtcgtg tgcttcttga acaacttcta ccccaaagac  540
atcaatgtca agtggaagat tgatggcagt gaacgacaaa atggcgtcct gaacagttgg  600
actgatcagg acagcaaaga cagcacctac agcatgagca gcaccctcac gttgaccaag  660
gacgagtatg aacgacataa cagctatacc tgtgaggcca ctcacaagac atcaacttca  720
cccattgtca agagcttcaa caggaatgag tgt                          753

SEQ ID NO: 21           moltype = AA  length = 529
FEATURE                 Location/Qualifiers
source                  1..529
                        mol_type = protein
                        organism = Homo sapiens
SEQUENCE: 21
MSQDTEVDMK EVELNELEPE KQPMNAASGA AMSLAGAEKN GLVKIKVAED EAEAAAAAKF  60
TGLSKEELLK VAGSPGWVRT RWALLLLFWL GWLGMLAGAV VIIVRAPRCR ELPAQKWWHT  120
GALYRIGDLQ AFQGHGAGNL AGLKGRLDYL SSLKVKGLVL GPIHKNQKDD VAQTDLLQID  180
PNFGSKEDFD SLLQSAKKKS IRVILDLTPN YRGENSWFST QVDTVATKVK DALEFWLQAG  240
VDGFQVRDIE NLKDASSFLA EWQNITKGFS EDRLLIAGTN SSDLQQILSL LESNKDLLLT  300
SSYLSDSGST GEHTKSLVTQ YLNATGNRWC SWSLSQARLL TSFLPAQLLR LYQLMLFTLP  360
GTPVFSYGDE IGLDAAALPG QPMEAPVMLW DESSFPDIPG AVSANMTVKG QSEDPGSLLS  420
LFRRLSDQRS KERSLLHGDF HAFSAGPGLF SYIRHWDQNE RFLVVLNFGD VGLSAGLQAS  480
DLPASASLPA KADLLLSTQP GREEGSPLEL ERLKLEPHEG LLLRFPYAA         529

SEQ ID NO: 22           moltype = AA  length = 65
FEATURE                 Location/Qualifiers
source                  1..65
                        mol_type = protein
                        organism = Homo sapiens
SEQUENCE: 22
```

```
FSYGDEIGLD AAALPGQPME APVMLWDESS FPDIPGAVSA NMTVKGQSED PGSLLSLFRR  60
LSDQR                                                              65

SEQ ID NO: 23           moltype = AA  length = 45
FEATURE                 Location/Qualifiers
source                  1..45
                        mol_type = protein
                        organism = Homo sapiens
SEQUENCE: 23
FSYGDEIGLD AAALPGQPME APVMLWDESS FPDIPGAVSA NMTVK                  45

SEQ ID NO: 24           moltype = AA  length = 225
FEATURE                 Location/Qualifiers
source                  1..225
                        mol_type = protein
                        organism = Homo sapiens
SEQUENCE: 24
VILDLTPNYR GENSWFSTQV DTVATKVKDA LEFWLQAGVD GFQVRDIENL KDASSFLAEW  60
QNITKGFSED RLLIAGTNSS DLQQILSLLE SNKDLLLTSS YLSDSGSTGE HTKSLVTQYL  120
NATGNRWCSW SLSQARLLTS FLPAQLLRLY QLMLFTLPGT PVFSYGDEIG LDAAALPGQP  180
MEAPVMLWDE SSFPDIPGAV SANMTVKGQS EDPGSLLSLF RRLSD                  225

SEQ ID NO: 25           moltype = DNA  length = 42
FEATURE                 Location/Qualifiers
misc_feature            1..42
                        note = Primer
source                  1..42
                        mol_type = other DNA
                        organism = synthetic construct
SEQUENCE: 25
ccggaattcc caccatgagc caggacaccg aggtggatat ga                     42

SEQ ID NO: 26           moltype = DNA  length = 44
FEATURE                 Location/Qualifiers
misc_feature            1..44
                        note = Primer
source                  1..44
                        mol_type = other DNA
                        organism = synthetic construct
SEQUENCE: 26
aaaggatcct catcaggccg cgtaggggaa gcggagcagc agcc                   44

SEQ ID NO: 27           moltype = DNA  length = 44
FEATURE                 Location/Qualifiers
misc_feature            1..44
                        note = Primer
source                  1..44
                        mol_type = other DNA
                        organism = synthetic construct
SEQUENCE: 27
ccggaattcc caccatgagc caggacaccg aagtggacat gaaa                   44

SEQ ID NO: 28           moltype = DNA  length = 35
FEATURE                 Location/Qualifiers
misc_feature            1..35
                        note = Primer
source                  1..35
                        mol_type = other DNA
                        organism = synthetic construct
SEQUENCE: 28
cgcggatcct catcaggcca caaaggggaa ctgta                             35

SEQ ID NO: 29           moltype = DNA  length = 27
FEATURE                 Location/Qualifiers
misc_feature            1..27
                        note = Primer
source                  1..27
                        mol_type = other DNA
                        organism = synthetic construct
SEQUENCE: 29
tcattctgga ccttactccc aactacc                                      27

SEQ ID NO: 30           moltype = DNA  length = 27
FEATURE                 Location/Qualifiers
misc_feature            1..27
                        note = Primer
source                  1..27
                        mol_type = other DNA
                        organism = synthetic construct
```

```
SEQUENCE: 30
ggtagttggg agtaaggtcc agaatga                                    27

SEQ ID NO: 31           moltype = DNA  length = 18
FEATURE                 Location/Qualifiers
misc_feature            1..18
                        note = Primer
source                  1..18
                        mol_type = other DNA
                        organism = synthetic construct
SEQUENCE: 31
ttccggcggc tgagtgac                                              18

SEQ ID NO: 32           moltype = DNA  length = 18
FEATURE                 Location/Qualifiers
misc_feature            1..18
                        note = Primer
source                  1..18
                        mol_type = other DNA
                        organism = synthetic construct
SEQUENCE: 32
gtcactcagc cgccggaa                                              18

SEQ ID NO: 33           moltype = DNA  length = 23
FEATURE                 Location/Qualifiers
misc_feature            1..23
                        note = Primer
source                  1..23
                        mol_type = other DNA
                        organism = synthetic construct
SEQUENCE: 33
agctacgggg atgagattgg cct                                        23

SEQ ID NO: 34           moltype = DNA  length = 23
FEATURE                 Location/Qualifiers
misc_feature            1..23
                        note = Primer
source                  1..23
                        mol_type = other DNA
                        organism = synthetic construct
SEQUENCE: 34
aggccaatct catccccgta gct                                        23

SEQ ID NO: 35           moltype = DNA  length = 33
FEATURE                 Location/Qualifiers
misc_feature            1..33
                        note = Primer
source                  1..33
                        mol_type = other DNA
                        organism = synthetic construct
SEQUENCE: 35
ttggcctgga tgcagctgcc cttcctggac agc                             33

SEQ ID NO: 36           moltype = DNA  length = 33
FEATURE                 Location/Qualifiers
misc_feature            1..33
                        note = Primer
source                  1..33
                        mol_type = other DNA
                        organism = synthetic construct
SEQUENCE: 36
gctgtccagg aagggcagct gcatccaggc caa                             33

SEQ ID NO: 37           moltype = DNA  length = 18
FEATURE                 Location/Qualifiers
misc_feature            1..18
                        note = Primer
source                  1..18
                        mol_type = other DNA
                        organism = synthetic construct
SEQUENCE: 37
tgcccttcct ggacagcc                                              18

SEQ ID NO: 38           moltype = DNA  length = 18
FEATURE                 Location/Qualifiers
misc_feature            1..18
                        note = Primer
source                  1..18
                        mol_type = other DNA
```

```
                        organism = synthetic construct
SEQUENCE: 38
ggctgtccag gaagggca                                            18

SEQ ID NO: 39           moltype = DNA  length = 30
FEATURE                 Location/Qualifiers
misc_feature            1..30
                        note = Primer
source                  1..30
                        mol_type = other DNA
                        organism = synthetic construct
SEQUENCE: 39
ccagcttccc tgacatccca ggggctgtaa                               30

SEQ ID NO: 40           moltype = DNA  length = 30
FEATURE                 Location/Qualifiers
misc_feature            1..30
                        note = Primer
source                  1..30
                        mol_type = other DNA
                        organism = synthetic construct
SEQUENCE: 40
ttacagcccc tgggatgtca gggaagctgg                               30

SEQ ID NO: 41           moltype = DNA  length = 26
FEATURE                 Location/Qualifiers
misc_feature            1..26
                        note = Primer
source                  1..26
                        mol_type = other DNA
                        organism = synthetic construct
SEQUENCE: 41
ctgtaagtgc caacatgact gtgaag                                   26

SEQ ID NO: 42           moltype = DNA  length = 26
FEATURE                 Location/Qualifiers
misc_feature            1..26
                        note = Primer
source                  1..26
                        mol_type = other DNA
                        organism = synthetic construct
SEQUENCE: 42
cttcacagtc atgttggcac ttacag                                   26

SEQ ID NO: 43           moltype = DNA  length = 29
FEATURE                 Location/Qualifiers
misc_feature            1..29
                        note = Primer
source                  1..29
                        mol_type = other DNA
                        organism = synthetic construct
SEQUENCE: 43
gggatgagtt aggcctggat gcagctgcc                                29

SEQ ID NO: 44           moltype = DNA  length = 25
FEATURE                 Location/Qualifiers
misc_feature            1..25
                        note = Primer
source                  1..25
                        mol_type = other DNA
                        organism = synthetic construct
SEQUENCE: 44
ggcctaactc atccccgtag ctgaa                                    25

SEQ ID NO: 45           moltype = DNA  length = 27
FEATURE                 Location/Qualifiers
misc_feature            1..27
                        note = primer
source                  1..27
                        mol_type = other DNA
                        organism = synthetic construct
SEQUENCE: 45
ggcctgcagg ctgcccttcc tggacag                                  27

SEQ ID NO: 46           moltype = DNA  length = 27
FEATURE                 Location/Qualifiers
misc_feature            1..27
                        note = Primer
source                  1..27
```

```
                        mol_type = other DNA
                        organism = synthetic construct
SEQUENCE: 46
ggcagcctgc aggccaatct catcccc                                         27

SEQ ID NO: 47           moltype = DNA  length = 27
FEATURE                 Location/Qualifiers
misc_feature            1..27
                        note = Primer
source                  1..27
                        mol_type = other DNA
                        organism = synthetic construct
SEQUENCE: 47
gatgcaggtg cccttcctgg acagcct                                         27

SEQ ID NO: 48           moltype = DNA  length = 27
FEATURE                 Location/Qualifiers
misc_feature            1..27
                        note = primer
source                  1..27
                        mol_type = other DNA
                        organism = synthetic construct
SEQUENCE: 48
aagggcacct gcatccaggc caatctc                                         27

SEQ ID NO: 49           moltype = DNA  length = 27
FEATURE                 Location/Qualifiers
misc_feature            1..27
                        note = primer
source                  1..27
                        mol_type = other DNA
                        organism = synthetic construct
SEQUENCE: 49
ctgtggaatg agtccagcat ctttcac                                         27

SEQ ID NO: 50           moltype = DNA  length = 27
FEATURE                 Location/Qualifiers
misc_feature            1..27
                        note = primer
source                  1..27
                        mol_type = other DNA
                        organism = synthetic construct
SEQUENCE: 50
ggactcattc cacagcatga ctggagc                                         27

SEQ ID NO: 51           moltype = DNA  length = 30
FEATURE                 Location/Qualifiers
misc_feature            1..30
                        note = primer
source                  1..30
                        mol_type = other DNA
                        organism = synthetic construct
SEQUENCE: 51
agcttatttc acatcccagg ggctgtaagt                                      30

SEQ ID NO: 52           moltype = DNA  length = 30
FEATURE                 Location/Qualifiers
misc_feature            1..30
                        note = primer
source                  1..30
                        mol_type = other DNA
                        organism = synthetic construct
SEQUENCE: 52
gatgtgaaat aagctggact catcccacag                                      30

SEQ ID NO: 53           moltype = DNA  length = 29
FEATURE                 Location/Qualifiers
misc_feature            1..29
                        note = primer
source                  1..29
                        mol_type = other DNA
                        organism = synthetic construct
SEQUENCE: 53
tcccaaggcc tgtaagtgcc aacatgact                                       29

SEQ ID NO: 54           moltype = DNA  length = 28
FEATURE                 Location/Qualifiers
misc_feature            1..28
                        note = primer
```

-continued

```
source                 1..28
                       mol_type = other DNA
                       organism = synthetic construct
SEQUENCE: 54
ttacaggcct tgggatgtca gggaagct                              28

SEQ ID NO: 55          moltype = DNA  length = 27
FEATURE                Location/Qualifiers
misc_feature           1..27
                       note = primer
source                 1..27
                       mol_type = other DNA
                       organism = synthetic construct
SEQUENCE: 55
gtaagtctca acatgactgt gaagggc                               27

SEQ ID NO: 56          moltype = DNA  length = 27
FEATURE                Location/Qualifiers
misc_feature           1..27
                       note = primer
source                 1..27
                       mol_type = other DNA
                       organism = synthetic construct
SEQUENCE: 56
catgttgaga cttacagccc ctgggat                               27

SEQ ID NO: 57          moltype = AA  length = 44
FEATURE                Location/Qualifiers
source                 1..44
                       mol_type = protein
                       organism = Mus musculus
SEQUENCE: 57
FSYGDELGLQ GALPGQPAKA PLMPWNESSI FHIPRPVSLN MTVK            44
```

ANTI-CD98HC ANTIBODY

TECHNICAL FIELD

Disclosed are a novel antibody, its use, and the like.

INCORPORATION BY REFERENCE OF SEQUENCE LISTING

A sequence listing in electronic (XML file) format is filed with this application and incorporated herein by reference. The name of the XML file is "AttachD_SEQLISTING-1169"; its date of creation is Feb. 19, 2026; and the size of the file is 73,160 bytes.

BACKGROUND ART

Multiple myeloma, which is a typical example of a disease causing neoplastic growth of plasma cells, accounts for about 1% of all cancers and a little more than 10% of all malignant hematological tumors. Multiple myeloma is a disease in which a plasma cell present in bone marrow becomes cancerous and undergoes monoclonal growth. In multiple myeloma, abnormal plasma cells (myeloma cells) spread to the bone marrow throughout the body and grow in every part of the bone marrow throughout the entire body. When the abnormal plasma cells grow, various symptoms, including bone breakage, appear. The myeloma cells produce M protein, which is an abnormal immunoglobulin, increasing the M protein concentration in blood, and the blood therefore becomes viscous. The M protein does not function as a usual antibody, which recognizes a foreign substance that has entered the body, such as a pathogen, and thus reduces immunocompetence. These phenomena affect many organs and cause various symptoms. Typical symptoms are bone pain and bone damage, hypercalcaemia, nephropathy and renal failure, anemia, etc.

Treatments of multiple myeloma mainly applied at present are proteasome inhibitors, iMIDs, such as thalidomide and its derivatives, specifically lenalidomide, chemotherapy using, for example, melphalan in combination with prednisone, and hematopoietic stem cell transplantation. However, the myeloma cells eventually acquire resistance to these therapeutic agents in most cases. Thus, the reality is that with the current treatment approaches, a myeloma patient has an unpromising prognosis with an average survival period after onset of from about 3 years to 5 years. In addition, a problem arises in that these therapeutic agents do not specifically act on only target tumor cells; therefore, the agents show toxicity also to normal cells, thereby causing serious side effects.

There have been attempts to develop a treatment method for multiple myeloma by using a monoclonal antibody. For example, an anti-CS1 antibody (Patent Literature 1) and an anti-CD38 antibody (Patent Literature 2) have been applied in clinical settings only recently.

CITATION LIST

Non-Patent Literature

NPL 1: Lonial et al., official journal of the American Society of Clinical Oncology, 2012 Jun. 1; 30 (16): 1953-1959.

NPL 2: de Weers et al., Journal of immunology, 2011 Feb. 1; 186 (3): 1840-1848

NPL 3: J Immunol. 2009 Nov. 1; 183 (9): 5563-74.

NPL 4: N Engl J Med. 2014 Oct. 16; 371 (16): 1507-17.

Non-patent Literature 5: Nat Biotechnol. 2002 January; 20 (1): 70-5.

SUMMARY OF INVENTION

Technical Problem

The anti-CS1 antibody shows relatively high specificity to myeloma cells, but the use of the antibody alone does not necessarily show a high degree of anti-myeloma effect. The efficacy of the antibody as a single drug has not been demonstrated in clinical trials. The combinational use of the anti-CS1 antibody with lenalidomide was found to increase the antitumor effect of the anti-CS1 antibody, and the anti-CS1 antibody was approved by the FDA for this combinational use. Although the anti-CD38 antibody was also approved by the FDA, CD38 is an antigen exhibiting low specificity as a treatment target of multiple myeloma due to its expression in normal blood cells, including many CD34-positive hematopoietic progenitor cells. In view of this current status, an object is to provide a more effective means to treatment of diseases involving neoplastic growth of plasma cells, such as multiple myeloma.

Solution to Problem

The present inventors conducted extensive research to achieve the object and came to a new perspective that even if a protein were not specific to myeloma cells, if post-translational modification of the protein were specific to myeloma cells, an antibody that recognizes it would be myeloma specific. The inventors then expected that by isolating antibodies specifically biding to myeloma cells and myeloma progenitor cells, and identifying the proteins that the antibodies recognize, it will be revealed whether the proteins are specific to myeloma cells, or whether antibodies recognize only those having some myeloma-specific post-translational modification despite the proteins' non-specificity to myeloma cells. They further assumed that ultimately, it will become possible to obtain an antibody that only recognizes a protein having post-translational modification specific to myeloma cells and myeloma progenitor cells as described above.

Based on this concept, the present inventors prepared, using multiple myeloma cell lines, 10,000 clones or more of monoclonal antibodies that bind to these cell lines, selected antibodies that do not bind to normal blood cells from the clones, and identified proteins recognized by the antibodies. As a result, as shown in the Examples described later, they identified R8H283 antibody and revealed that the antigen bound by the R8H283 antibody was CD98hc. Although CD98hc is expressed in normal blood cells, the R8H283 antibody was confirmed to specifically recognize myeloma cells because the epitope for the R8H283 antibody is present in the region affected by the presence of the N-glycan on CD98hc, and because the way the N-glycan attaches differs between a myeloma cell (including myeloma plasma cells and myeloma progenitor cells) and a normal blood cell.

Additionally, the inventors confirmed that the R8H283 antibody has cytotoxic activity, that the proliferation of myeloma cells can be inhibited by administering the antibody to an animal transplanted with myeloma cells, and that the R8H283 antibody recognizes various other tumor cells in addition to myeloma cells. After further research and exhaustive consideration based on these findings, the inventors have provided inventions represented by the following subject matter.

1. Antibody

Item 1-1.

An anti-human CD98hc antibody, whose affinity for human CD98hc increases when a sugar chain bound to the human CD98hc is removed.

Item 1-1.5.

An anti-human CD98hc antibody, whose affinity for a cell that expresses human CD98hc increases when the cell treated with tunicamycine.

Item 1-2.

An anti-human CD98hc antibody, whose affinity for a CD98hc variant in which amino acid residues at positions 395 to 397 of human CD98hc are replaced by amino acid residues of mouse-originated CD98hc is equivalent to its affinity for the mouse-originated CD98hc.

Item 1-3.

An anti-human CD98hc antibody, whose affinity for a CD98hc variant in which amino acid residues at positions 400 and 401 of human CD98hc are replaced by amino acid residues of mouse-originated CD98hc is equivalent to its affinity for the mouse-originated CD98hc.

Item 1-4.

An antibody recognizing an epitope that comprises an N-glycosylation site of human CD98hc, and that is exposed by inhibiting N-linked glycosylation.

Item 1-5.

An antibody, whose epitope is present within a region affected by the presence of an N-glycan on human CD98hc.

Item 1-6.

An antibody comprising characteristics recited in at least two items selected from the group consisting of Items 1-1 to 1-5.

Item 1-7.

An antibody according to Item 1-5 or 1-6, wherein the region is the amino acid sequence of SEQ ID NO: 24 on human CD98hc.

Item 1-8.

An antibody according to Item 1-5 or 1-6, wherein the region is the amino acid sequence of SEQ ID NO: 22 on human CD98hc.

Item 1-9.

An antibody according to Item 1-9, wherein the region is the amino acid sequence of SEQ ID NO: 23 on human CD98hc.

Item 1-10.

An antibody according to any one of Items 1-1 to 1-9, whose epitope is present within a region of the amino acid sequence of SEQ ID NO: 24.

Item 1-11.

An antibody, whose epitope is present within a region of the amino acid sequence of SEQ ID NO: 24 of human CD98hc.

Item 1-12.

An antibody according to any one of Items 1-1 to 1-11 whose epitope is present within a region of the amino acid sequence of SEQ ID NO: 22.

Item 1-13.

An antibody, whose epitope is present within a region of the amino acid sequence of SEQ ID NO: 22 of human CD98hc.

Item 1-14.

An antibody according to any one of Items 1-1 to 1-13, whose epitope is present within a region of the amino acid sequence of SEQ ID NO: 23.

Item 1-15.

An antibody, whose epitope is present within a region of the amino acid sequence of SEQ ID NO: 23 of human CD98hc.

Item 1-16.

An antibody according to any one of Items 1-1 to 1-15, whose epitope is identical to an epitope for R8H283 antibody.

Item 1-17.

An antibody according to any one of Items 1-1 to 1-16, whose affinity for human CD98hc having no N-glycan is higher than its affinity for human CD98hc having an N-glycan.

Item 1-18.

An antibody according to any one of Items 1-1 to 1-17, comprising

- a heavy chain variable region comprising
  - a heavy chain CDR1 comprising an amino acid sequence containing the amino acid sequence of SEQ ID NO: 1,
  - a heavy chain CDR2 comprising an amino acid sequence containing the amino acid sequence of SEQ ID NO: 2, and/or
  - a heavy chain CDR3 comprising an amino acid sequence containing the amino acid sequence of SEQ ID NO: 3; and/or
- a light chain variable region comprising
  - a light chain CDR1 comprising an amino acid sequence containing the amino acid sequence of SEQ ID NO: 5,
  - a light chain CDR2 comprising an amino acid sequence containing the amino acid sequence of SEQ ID NO: 6, and/or
  - a light chain CDR3 comprising an amino acid sequence containing the amino acid sequence of SEQ ID NO: 7.

Item 1-19.

An antibody according to any one of Items 1-1 to 1-18, comprising

- a heavy chain variable region comprising the amino acid sequence of SEQ ID NO: 4, and/or
- a light chain variable region comprising the amino acid sequence of SEQ ID NO: 8.

Item 1-20.

An antibody according to any one of Items 1-1 to 1-19, which is Fv, scFv, a diabody, a triabody, a tetrabody, or a combination thereof.

Item 1-21.

An antibody according to any one of Items 1-1 to 1-20, which is a monoclonal antibody.

Item 1-22.

An antibody according to any one of Items 1-1 to 1-7 and 1-21, comprising a constant region.

Item 1-23.

An antibody according to any one of Items 1-1 to 1-19 and 1-21, which is a chimeric antibody.

Item 1-24.

An antibody according to any one of Items 1-1 to 1-23, which is a humanized antibody.

Item 1-25.

An antibody according to any one of Items 1-1 to 1-24, which is a human antibody.

Item 1-26.

An antibody according to any one of Items 1-1 to 1-19 and 1-21 to 1-25, which is an immunoglobulin, Fab, F(ab)', minibody, scFv-Fc, or a combination thereof.

Item 1-27.

An antibody according to any one of Items 1-1 to 1-19 and 1-21 to 1-26, which is IgA, IgD, IGE, IGG, or IgM.

Item 1-28.

An antibody according to any one of Items 1-1 to 1-19 and 1-21 to 1-27, comprising a heavy chain containing the amino acid sequence of SEQ ID NO: 5, and/or a light chain containing the amino acid sequence of SEQ ID NO: 10.

Item 1-29.

An antibody according to any one of Items 1-1 to 1-19 and 1-21 to 1-28, having cytotoxic activity.

Item 1-30.

An antibody according to any one of Items 1-1 to 1-29, having a cytotoxin bound thereto.

Item 1-31.

An antibody according to any one of Items 1-1 to 1-30, which is a multispecific antibody.

Item 1-32.

A polynucleotide encoding the antibody according to any one of Items 1-1 to 1-31.

Item 1-33.

A host cell comprising the polynucleotide according to Item 1-33.

Item 1-34.

A host cell according to Item 1-33, which is a T cell.

2. Chimeric Antigen Receptor

Item 2-1.

An anti-human CD98hc chimeric antigen receptor, whose affinity for human CD98hc is increased by removing a sugar chain binding to the human CD98hc.

Item 2-1.5.

An anti-human CD98hc chimeric antigen receptor, whose affinity for a cell that expresses human CD98hc is increased by treating the cell with tunicamycine.

Item 2-2.

An anti-human CD98hc chimeric antigen receptor, whose affinity for a CD98hc variant in which amino acid residues at positions 395 to 397 of human CD98hc are replaced by amino acid residues of mouse-originated CD98hc is equivalent to its affinity for the mouse-originated CD98hc.

Item 2-3.

An anti-human CD98hc chimeric antigen receptor, whose affinity for a CD98hc variant in which amino acid residues at positions 400 and 401 of human CD98hc are replaced by amino acid residues of mouse-originated CD98hc is equivalent to its affinity for the mouse-originated CD98hc.

Item 2-4.

An anti-human CD98hc chimeric antigen receptor recognizing an epitope that comprises an N-glycosylation site of human CD98hc, and that is exposed by inhibiting N-linked glycosylation.

Item 2-5.

An anti-human CD98hc chimeric antigen receptor comprising characteristics recited in at least two items selected from the group consisting of Items 2-1 to 2-4.

Item 2-6.

An anti-human CD98hc chimeric antigen receptor, whose epitope is present within a region of the amino acid sequence of SEQ ID NO: 24 of human CD98hc.

Item 2-7.

An anti-human CD98hc chimeric antigen receptor according to any one of Items 2-1 to 2-5, whose epitope is present within a region of the amino acid sequence of SEQ ID NO: 24 of human CD98hc.

Item 2-8.

An anti-human CD98hc chimeric antigen receptor according to any one of Items 2-1 to 2-5, whose epitope is present within a region of the amino acid sequence of SEQ ID NO: 22 of human CD98hc.

Item 2-9.

An anti-human CD98hc chimeric antigen receptor, whose epitope is present within a region of the amino acid sequence of SEQ ID NO: 22 of human CD98hc.

Item 2-10.

An anti-human CD98hc chimeric antigen receptor according to any one of Items 2-1 to 2-9, whose epitope is present within a region of the amino acid sequence of SEQ ID NO: 23.

Item 2-11.

An anti-human CD98hc chimeric antigen receptor, whose epitope is present within a region of the amino acid sequence of SEQ ID NO: 23 of human CD98hc.

Item 2-12.

An anti-human CD98hc chimeric antigen receptor according to any one of Items 2-1 to 2-11, whose epitope is identical to an epitope for an R8H283 antibody.

Item 2-13.

An anti-human CD98hc chimeric antigen receptor according to any one of Items 2-1 to 2-12, whose affinity for human CD98hc having no N-glycan is higher than its affinity for human CD98hc having an N-glycan.

Item 2-14.

An anti-human CD98hc chimeric antigen receptor according to any one of Items 2-1 to 2-13, comprising a heavy chain variable region comprising a heavy chain CDR1 comprising an amino acid sequence containing the amino acid sequence of SEQ ID NO: 1, a heavy chain CDR2 comprising an amino acid sequence containing the amino acid sequence of SEQ ID NO: 2, and a heavy chain CDR3 comprising an amino acid sequence containing the amino acid sequence of SEQ ID NO: 3; and/or a light chain variable region comprising a light chain CDR1 comprising an amino acid sequence containing the amino acid sequence of SEQ ID NO: 6, a light chain CDR2 comprising an amino acid sequence containing the amino acid sequence of SEQ ID NO: 7, and a light chain CDR3 comprising an amino acid sequence containing the amino acid sequence of SEQ ID NO: 8.

Item 2-15.

An anti-human CD98hc chimeric antigen receptor according to any one of Items 2-1 to 2-14, comprising a heavy chain variable region containing the amino acid sequence of SEQ ID NO: 4, and/or a light chain variable region containing the amino acid sequence of SEQ ID NO: 9.

Item 2-16.

A polynucleotide encoding the anti-human CD98hc chimeric antigen receptor according to any one of Items 2-1 to 2-15.

Item 2-17.

A host cell comprising the polynucleotide according to Item 2-16.

Item 2-18.

A host cell according to Item 2-17, which is a T cell.

Item 2-19.

A host cell according to Item 2-18, which is a chimeric antigen receptor T cell or a chimeric antigen receptor NK cell.

3. Pharmaceutical Composition and Treatment Method

Item 3-1.

A pharmaceutical composition comprising at least one member selected from the group consisting of the antibody according to any one of Items 1-1 to 1-34, the anti-human CD98hc chimeric antigen receptor T cell according to Item 2-19, and the anti-human CD98hc chimeric antigen receptor NK cell according to Item 2-19.

Item 3-2.

A pharmaceutical composition according to Item 3-1, which is for use in the treatment or prevention of a tumor.

Item 3-3.

A pharmaceutical composition according to Item 3-1 or 3-2, which is for use in the treatment or prevention of a disease that causes neoplastic growth of a plasma cell.

Item 3-4.

A method comprising administering the pharmaceutical composition according to Item 3-1 to a patient in need of treatment of a disease.

Item 3-5.

A method according to Item 3-4, wherein the patient has cancer.

Item 3-6.

A method according to Item 3-5, wherein the patient has a disease that causes neoplastic growth of a plasma cell.

Item 3-7.

Use of at least one member selected from the group consisting of the antibody according to any one of Items 1-1 to 1-34, the anti-human CD98hc chimeric antigen receptor T cell according to Item 2-19, and the anti-human CD98hc chimeric antigen receptor NK cell according to Item 2-19 for production of a pharmaceutical composition.

Item 3-8.

Use according to Item 3-7, wherein the pharmaceutical composition is for treatment or prevention of a tumor.

Item 3-9.

Use according to Item 3-8, wherein the pharmaceutical composition is for treatment or prevention of a disease that causes neoplastic growth of a plasma cell.

4. Screening Method

Item 4-1.

A screening method for a substance that is effective in treating or preventing a tumor, the method comprising selecting, from a candidate substance group, a substance that specifically binds to a region that contains an N-glycosylation site of human CD98hc and that is exposed by inhibiting N-linked glycosylation.

Item 4-2.

A method according to Item 4-1, further comprising screening for a substance having cytotoxic activity.

5. Diagnostic Method 5-1.

A method for diagnosing a tumor, the method comprising bringing a sample collected from a test subject into contact with the antibody according to any one of Items 1-1 to 1-34.

5-2.

A method according to Item 5-1, the method comprising diagnosing the presence of a tumor when a cell that binds to the antibody is detected.

5-3.

A method according to Item 5-1 or 5-2, wherein the sample is blood or bone marrow fluid.

5-4.

A kit for diagnosing a tumor, the kit comprising the antibody according to any one of Items 1-1 to 1-34.

Advantageous Effects of Invention

Because the antibodies described above specifically recognize myeloma progenitor cells, myeloma plasma cells, and other tumor cells, the antibodies enable the effective treatment of diseases, such as malignant tumors, without targeting normal cells.

BRIEF DESCRIPTION OF DRAWINGS

FIG. 11 also shows (B) the results of FACS analysis of the binding of the R8H283 antibody or MEM-108 to U937 cells treated with thapsigargin (1 mM) for 48 hours and non-treated U937 cells.

FIG. 13 shows the results of FACS analysis of the binding of the R8H283 antibody and MEM-108 antibody to CD138-positive CD38-strong positive myeloma cells (MM) and CD3-positive T cells.

FIG. 18 shows (B) the results by which the R8H283 antibody was confirmed to have a capability of dose-dependently eliminating U266 cells engrafted in the bone marrow and (C) the spread of U266 cells on day 40 observed by IVIS after 5 mg/kg of the antibody was administered.

FIG. 19 also shows (C) changes in tumor volume of each treatment group.

FIG. 20 shows on the lower side the bond strength of the R8H283 antibody to 293T-cells transiently expressing human/mouse chimera CD98hc. The MFI in the vertical axis indicates the bond strength of the R8H283 antibody; the higher the value, the stronger the bond.

DESCRIPTION OF EMBODIMENTS

1. Definition

Figure 1:
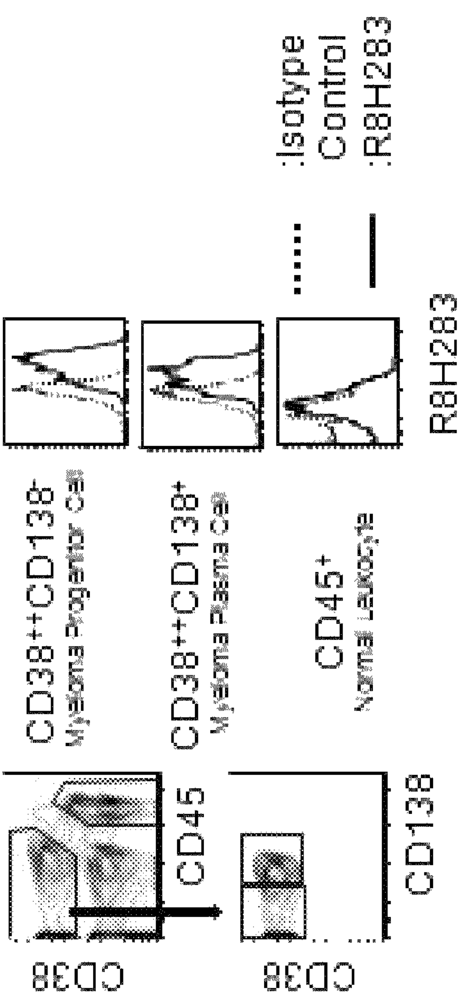
FIG. 1 shows (A) a process by which antibodies that bind to CD45−CD38++CD138+ myeloma plasma cells and CD45−CD38++CD138− myeloma progenitor cells but not to CD45+ blood cells were selected from candidate antibodies by flow cytometry, and (B) the results confirmed by FACS that the R8H283 antibody binds to CD45−CD38++ CD138+ myeloma plasma cells and CD45−CD38++ CD138− myeloma progenitor cells but not to CD45+ blood cells.

The "myeloma progenitor cell" is a progenitor cell at the stage immediately before differentiating into a myeloma plasma cell. Although the myeloma progenitor cell highly expresses CD38, the cell is characterized by the absence of CD138 expression, which is a marker specific to mature plasma cells. Thus, the myeloma progenitor cell may also be referred to as a "CD38++CD138− cell" or "CD19−CD38++ CD138− cell."

The "myeloma plasma cell" is also typically referred to as a "myeloma cell," and produces M protein, which is an abnormal immunoglobulin. In myeloma plasma cells, in addition to the high level of CD38 expression, CD138 is also expressed. Thus, the myeloma plasma cell may also be referred to as a "CD38++CD138+ cell" or "CD19−CD38++ CD138+ cell."

"Myeloma progenitor cell" and "myeloma plasma cell" also respectively mean a tumor progenitor cell and a neoplastic plasma cell in diseases that cause neoplastic growth of a plasma cell, other than multiple myeloma.

The "hematopoietic progenitor cell" is a cell capable of differentiating into various blood cells. The hematopoietic progenitor cell is characterized by the expression of CD34.

Thus, "hematopoietic progenitor cell" as used herein may be referred to as a "CD34+ cell."

In this specification, although "comprise," "contain," "include," and "have" are open-language terms, these terms include the concept of the closed-language term "consist of" and can be replaced by "consist of" in an embodiment.

2. Antibody

In an embodiment, provided is an antibody recognizing an epitope that contains an N-glycosylation site of human CD98hc and that is exposed by inhibiting N-linked glycosylation. CD98 (or "4F2") is a heterodimer protein of about 120 kDa that is expressed on a cell membrane and is known to function as an amino acid transporter. CD98hc is a type II transmembrane protein of about 80 kDa that constitutes CD98 and may be referred to as "4F2 hc" or "SLC3A2." Although there are several isoforms (e.g., b, c, e, and f) for human CD98hc, these isoforms have a common amino acid sequence for their extracellular domain. The sequence list shows the amino acid sequence of isoform f, which is a typical human CD98hc, as SEQ ID NO: 21. Human CD98hc has a structure in which N-glycans can bind to the position 264, position 280, position 323, and position 405 of the amino acid sequence of SEQ ID NO: 21. Although the amino acid sequence of isoform f of human CD98hc is referenced as a typical example in this specification, a person skilled in the art would understand that the corresponding sequence and the corresponding amino acid residues are present in other isoforms and function equivalently.

As shown in the Examples described later, N-glycans on CD98hc in myeloma cells, myeloma progenitor cells, and other tumor cells are considered to have undergone a change (e.g., failure of N-linked glycosylation). This is probably because myeloma cells, myeloma progenitor cells, and other tumor cells are always subjected to endoplasmic reticulum stress, and N-linked glycosylation is being inhibited. This suggests that an amino acid sequence of CD98hc that an antibody cannot access in other normal cells is exposed on the surface of myeloma cells, myeloma progenitor cells, or other tumor cells, and so the antibody can access the amino acid sequence. In this specification, this region of CD98hc specific to the myeloma cell and the myeloma progenitor cell is referred to as the "region that contains an N-glycosylation site of human CD98hc, and that is exposed by inhibiting N-linked glycosylation" or the "region affected by the presence of an N-glycan." Because an epitope is present in this region, the antibody can specifically recognize a myeloma cell or myeloma progenitor cell. The size of the region can be any size, and is not particularly limited. For example, the region is composed of 40 amino acid residues or less, 35 amino acid residues or less, 30 amino acid residues or less, 25 amino acid residues or less, 20 amino acid residues or less, 15 amino acid residues or less, or 10 amino acid residues or less. In an embodiment, it is possible for the epitope to contain no N-glycosylation site of human CD98hc.

"N-glycosylation site of human CD98hc" refers to, among the amino acid residues constituting human CD98hc, amino acid residues to which an N-glycan binds. In an embodiment, the N-glycosylation site is an asparagine residue at position 264, 280, 323, or 405 of the amino acid sequence of SEQ ID NO: 21. In a preferable embodiment, the N-glycosylation site is an asparagine residue at position 405 of the amino acid sequence of SEQ ID NO: 21.

In an embodiment, an anti-human CD98hc antibody preferably has the property that its affinity for CD98hc is increased by inhibiting the binding of an N-glycan to CD98hc expressed in a cell. The binding of an N-glycan to CD98hc can be inhibited, for example, by treating the cell that expresses CD98hc with tunicamycin, thapsigargin, or bortezomib. Thus, if the amount of binding of the antibody to human CD98hc is increased by treating a cell that expresses human CD98hc (e.g., U937 cell) with these medicinal agents compared with an untreated cell, the antibody is confirmed to have an increased affinity for human CD98hc by inhibiting the binding of an N-glycan to human CD98hc or to recognize an epitope exposed by inhibiting N-linked glycosylation. This method also can determine whether the epitope for the antibody is present within the region affected by the presence of an N-glycan. Specifically, if the binding capability of the antibody to human CD98hc is changed by treating a cell that expresses human CD98hc with the medicinal agents compared with an untreated cell, the epitope for the antibody is determined to be present within the region affected by the presence of an N-glycan.

In an embodiment, the antibody is preferably an anti-human CD98hc antibody whose affinity for human CD98hc is increased by removing a sugar chain that binds to human CD98hc. Whether an antibody has this property can be confirmed by any technique. For example, the affinity of an antibody for human CD98hc expressed under the condition that a sugar chain binds to human CD98hc can be compared with the affinity of the antibody for human CD98hc expressed under the condition that the binding of a sugar chain is inhibited or decreased; then, it is confirmed whether the antibody has the property that the affinity for human CD98hc is increased by removing the sugar chain that binds to human CD98hc. The binding of a sugar chain to human CD98hc can be inhibited or decreased, for example, by treating a cell that expresses CD98hc with tunicamycin, thapsigargin, or bortezomib as described above. Specific conditions under which the cell that expresses human CD98hc is treated with tunicamycin, thapsigargin, or bortezomib are not particularly limited, as long as the binding of a sugar chain is inhibited or decreased. For example, the conditions may comply with the conditions used in the Examples described later. The cell that expresses CD98hc for use is, for example, U937 cell. The increase in affinity can be measured using as an indicator an increase in fluorescent intensity (mean fluorescent intensity) caused by the binding of the antibody in flow cytometry analysis performed in accordance with the conditions used in the Examples described later. The degree of the increase in fluorescent intensity is not particularly limited. For example, when U937 cell is used, the degree of increase in fluorescent intensity is preferably 1.5 times or more, 1.7 times or more, or 2 times or more the fluorescent intensity before treatment. When THP-1 cell is used, the degree of increase in fluorescent intensity is preferably, for example, 3 times or more, 4 times or more, 5 times or more, or 6 times or more the fluorescent intensity before treatment.

In an embodiment, the anti-human CD98 antibody is preferably an anti-human CD98hc antibody whose affinity for a CD98hc variant in which the amino acid residues at positions 395 to 397 of human CD98hc are replaced by amino acid residues of mouse-originated CD98hc is equivalent to its affinity for the mouse-originated CD98hc. The CD98hc variant in which the amino acid residues at positions 395 to 397 of human CD98hc are replaced by amino acid residues of mouse-originated CD98hc is a human CD98hc variant in which F at position 395, P at position 396, and D at position 397 on human CD98hc are respectively replaced by I, F, and H. The affinity of the anti-human CD98hc antibody for a human CD98hc variant being equivalent to its affinity for mouse-originated human CD98hc means that the anti-human CD98hc antibody does not substantially bind to the human CD98hc variant.

In an embodiment, the anti-human CD98 antibody is preferably an anti-human CD98hc antibody whose affinity for a CD98hc variant in which the amino acid residues at positions 400 and 401 of human CD98hc are replaced by amino acid residues of mouse-originated CD98hc is equivalent to its affinity for the mouse-originated CD98hc. The CD98hc variant in which the amino acid residues at positions 400 and 401 of human CD98hc are replaced by amino acid residues of mouse-originated CD98hc is a human CD98hc variant in which G at position 400 and A at position 401 on human CD98hc are respectively replaced by R and P. The affinity of the anti-human CD98hc antibody for a human CD98hc variant being equivalent to its affinity for mouse-originated human CD98hc means that the anti-human CD98hc antibody does not substantially bind to the human CD98hc variant.

The affinity for a human CD98hc variant being equivalent to its affinity for mouse-originated CD98hc means the following: the bond strength of a mouse-originated CD98hc and the bond strength of a CD98hc variant are measured under the same conditions with a flow cytometer; the ratio of the bond strength represented by a mean fluorescent intensity (MFI) between them (the bond strength of the CD98hc variant/the bond strength of the mouse-originated CD98hc) is 1.1 to 0.9, and preferably 1.05 to 0.95.

An antibody having such a property can be obtained by the following procedure. First, an anti-human CD98hc antibody is obtained using, as an antigen, a mouse cell in which human CD98hc has been expressed in accordance with the method of the Examples described later. Next, a CHO cell expressing a CD98hc variant prepared by replacing the amino acid residues at positions 395 to 397 of human CD98hc by the amino acid residues of mouse-originated CD98hc in accordance with the method of the Examples (a construct F395I/P396F/D397H in the Examples described later) is stained with the obtained antibody, and flow cytometry analysis is performed. At the same time, a CHO cell expressing mouse CD98hc is also stained, and analyzed by flow cytometry. Ultimately, it is possible to obtain an anti-human CD98hc antibody whose affinity for the CD98hc variant in which the amino acid residues at positions 395 to 397 of human CD98hc are replaced by the amino acid residues of mouse-originated CD98hc is equivalent to its affinity for the mouse-originated CD98hc by selecting one whose affinity for the human CD98hc variant is equivalent to its affinity for the mouse-originated CD98hc. Equivalent affinity means that the ratio of the bond strength of a mouse-originated CD98hc to the bond strength of a CD98hc variant both measured under the same conditions with a flow cytometer (the bond strength of CD98hc variant/the bond strength of mouse-originated CD98hc) is 1.1 to 0.9, and preferably 1.05 to 0.95 (the bond strength is represented by a mean fluorescent intensity (MFI)).

In an embodiment, the epitope exposed by inhibiting N-linked glycosylation of human CD98hc is preferably present in the region corresponding to positions 203 to 427 of SEQ ID NO: 21 on human CD98hc. In a preferable embodiment, the epitope for the antibody is preferably present in the region corresponding to positions 365 to 427 of SEQ ID NO: 21 on human CD98hc. In another preferable embodiment, the epitope for the antibody is preferably present in the region corresponding to positions 365 to 409 of SEQ ID NO: 21 on human CD98hc. The phrase "corresponding to" is used here because the two regions described above in human CD98hc other than isoform f are not necessarily positions 365 to 427 and positions 365 to 409 from the amino acid residue at the N-terminus taken as position 1. The amino acid sequence at positions 365 to 427 of SEQ ID NO: 21 is as follows: FSYGDEIGLDAAALPGOPMEAPVMLWDESSFPDIPGAVSANMTVKGQSEDPGSLLSLFRRLSDQR (SEQ ID NO: 22). The amino acid sequence at positions 365 to 409 of SEQ ID NO: 21 is as follows: FSYGDEIGLDAAALPGOPMEAPVMLWDESSFPDIPGAVSANMTVK (SEQ ID NO: 23). Thus, in a preferable embodiment, the epitope exposed by inhibiting N-linked glycosylation of human CD98hc is preferably present in the region of the amino acid sequence of SEQ ID NO: 22 of human CD98hc, and more preferably present in the region of the amino acid sequence of SEQ ID NO: 23. The amino acid sequence at positions 203 to 427 of SEQ ID NO: 21 is shown as SEQ ID NO: 24 in the sequence list.

In an embodiment, the epitope for the anti-human CD98hc antibody is preferably present in the region at positions 365 to 376 and in the region at positions 395 to 409 of human CD98hc. In an embodiment, the epitope for the anti-human CD98hc antibody preferably contains the amino acid residues at positions 374, 375, 395, 396, 397, 400, and 401 of human CD98hc. As used herein, the position of an amino acid residue of human CD98hc is the position on the amino acid sequence of SEQ ID NO: 21 unless indicated otherwise.

Whether an epitope for the antibody is present in the region of the amino acid sequence represented by SEQ ID NO: 23 can be confirmed by the following procedure. Specifically, a polynucleotide is constructed; the polynucleotide encodes human/mouse chimera CD98hc in which the region other than the amino acid sequence represented by SEQ ID NO: 23 is replaced by amino acid sequences of mouse-originated CD98hc. The polynucleotide is then forcibly expressed in a suitable cell. Separately, a cell of the same kind in which mouse CD98hc has been forcibly expressed is prepared. The binding of the antibody to these cells is measured. When the antibody binds to the cell that expresses chimera CD98hc, but not to the cell that expresses mouse CD98hc, an epitope is determined to be present in the region. Here, the amino acid sequence of SEQ ID NO: 23 is described as an example, and measurement can also be performed in the same manner in the case of other regions or sites.

An example of the antibody recognizing an epitope that contains an N-glycosylation site of human CD98hc and that is exposed by inhibiting N-linked glycosylation, and exhibiting increased affinity for human CD98hc by inhibiting the binding of the N-glycan to human CD98hc, is the R8H283 antibody obtained in the Examples described later. Thus, in an embodiment, the epitope for the antibody is preferably identical to the epitope for the R8H283 antibody. In another embodiment, the antibody is preferably the R8H283 antibody.

In an embodiment, the antibody may have any structure, as long as the antibody exhibits the properties described above. The antibody preferably has a complementarity-determining region identical to at least one complementarity-determining region selected from the group consisting of three heavy-chain complementarity-determining regions (CDR-H1, CDR-H2, and CDR-H3) and three light-chain complementarity-determining regions (CDR-L1, CDR-L2, and CDR-L3) of the R8H283 antibody. The amino acid sequences of the heavy-chain hypervariable region and light-chain hypervariable region of the R8H283 antibody are as shown in Table 1 below.

TABLE 1

| Amino Acid Sequence of R8H283 Antibody | | |
|---|---|---|
| Heavy Chain | CDR-H1 (SEQ ID NO: 1) | GFTF |
| | CDR-H2 (SEQ ID NO: 2) | IRLKSNNYAT |
| | CDR-H3 (SEQ ID NO: 3) | SRLPSFDY |
| | Variable Region (SEQ ID NO: 4) | EVKLEESGGGLVQPGGSMKLSCVASGFTFSNYWMNWVR QSPEKGLEWVAEIRLKSNNYATHYAESYKGRFTISRDD SKSSVYLQMNNLRAEDTGIYYCSRLPSFDY |
| Light Chain | CDR-L1 (SEQ ID NO: 6) | KSLLHSNGNTY |
| | CDR-L2 (SEQ ID NO: 7) | RMS |
| | CDR-L3 (SEQ ID NO: 8) | MQHLEYPFTF |
| | Variable Region (SEQ ID NO: 9) | MRCLAEPLGLLVLWIPGAIGDIVMTQAAPSVPVTPGES VSISCRSTKSLLHSNGNTYLYWFLQRPGQSPQLLIYRM SNLASGVPDRFSGSGSGTAFTLRITRVEAEDVGIYYCM QHLEYPFTFGAGYKLR LK |

In an embodiment, the antibody contains at least one CDR selected from the group consisting of CDR-H1, CDR-H2, CDR-H3, CDR-L1, CDR-L2, and CDR-L3 of the R8H283 antibody, preferably at least 2, preferably at least 3, preferably at least 4, preferably at least 5, and preferably all of the 6 CDRs. In an embodiment, the antibody preferably contains at least CDR-H3 and/or CDR-L3 of the R8H283 antibody.

In an embodiment, the heavy chain variable region of the antibody preferably has the same amino acid sequence as that of the heavy chain variable region of the R8H283 antibody (SEQ ID NO: 4). In an embodiment, the light chain variable region of the antibody preferably has the same amino acid sequence as that of the light chain variable region of the R8H283 antibody (SEQ ID NO: 9). The antibody preferably has the same amino acid sequence as that of the heavy chain variable region of the R8H283 antibody (SEQ ID NO: 4) and the same amino acid sequence as that of the light chain variable region of the R8H283 antibody (SEQ ID NO: 9). As used herein, the meaning of "the same" includes the meaning of not only a complete match of amino acid sequences but also having substantially the same epitope as that of the R8H283 antibody with one or several (e.g., 15 or less, preferably 10 or less, preferably 5 or less, preferably 3 or less, preferably 2) amino acid residues being different.

In an embodiment, the amino acid sequence of the heavy chain variable region of the antibody has at least 90%, preferably at least 95%, preferably at least 98%, and preferably at least 99% identity with the amino acid sequence of SEQ ID NO: 4. In an embodiment, the light chain variable region of the antibody has at least 95%, preferably at least 98%, and preferably at least 99% identity with the amino acid sequence of SEQ ID NO: 9. The identity of amino acids sequences is measured by the technique described later.

The antibody may have any structure as long as the antibody recognizes an epitope that contains an N-glycosylation site of human CD98hc and that is exposed by inhibiting N-linked glycosylation, and the antibody does not necessarily need to contain a constant region. For example, the structure of the antibody can be any structure selected from the group consisting of Fv, scFv, diabody, triabody, tetrabody, and any combinations thereof.

"Fv" is considered to be the smallest structure unit of an antibody and has the heavy chain variable region and the light chain variable region that are aggregated by non-covalent, intermolecular interaction. In Fv, a thiol group of the cysteine residue present in the heavy chain variable region and a thiol group of the cysteine residue present in the light chain variable region may be disulfide bonded.

"scFv" has the structure in which the C-terminus of the heavy chain variable region and the N-terminus of the light chain variable region are bound through a linker, and is also referred to as a "single-chain antibody." scFv may have the structure in which the N-terminus of the heavy chain variable region and the C-terminus of the light chain variable region are bound through a linker.

The "diabody," "triabody," and "tetrabody" respectively refer to a dimer, a trimer, and a tetramer formed by scFv described above and are each an aggregated and structurally stabilized structure, for example, by non-covalent, intermolecular interaction of the variable regions, as with Fv.

An antibody having such a structure can be prepared by selecting any method known in the art. For example, the antibody can be obtained by constructing an expression vector using a gene genetic engineering technique, and allowing it to be expressed in a host cell or cell-free expression system suitable for the production of the antibody. The host cell can be of any type and the type is not particularly limited. For example, the host cell can be suitably selected from prokaryotic cells (e.g., *Escherichia coli* and actinomycete) and eukaryotic cells (e.g., yeast cells, insect cells, and mammalian cells). A high-purity antibody can be obtained by subjecting the expressed antibody to any purification technique.

In an embodiment, the antibody preferably has a constant region. It is known that a heavy chain possesses three types of constant regions, CH1, CH2, and CH3, and a light chain possesses one type of constant region CL. The region containing CH2 and CH3 is also called an "Fc domain." The antibody may contain at least one constant region selected from the group consisting of CH1, CH2, CH3, and CL, and may contain all of the constant regions.

The amino acid sequence of the constant region is somewhat constant depending on the origin and the class of the antibody. The constant region may be of any origin. For example, the constant region can be of human origin, mouse origin, rat origin, rabbit origin, monkey origin, or chimpanzee origin. The origin of the constant region can be selected depending on the purpose, such as mass production or a decrease in immunogenicity for humans.

In an embodiment, the antibody is preferably a chimeric antibody. The chimeric antibody can be obtained, for example, by replacing the constant region of a mouse antibody by the constant region of human origin. The chimeric antibody can be prepared in accordance with a known method.

In an embodiment, the antibody is preferably a humanized antibody. The humanized antibody can be obtained, for example, by replacing not only the amino acid sequence of the constant region of a mouse antibody but also the amino acid sequence in the region other than the hypervariable region present in the variable region by the amino acid sequences of a human antibody. The region other than the hypervariable region present in the variable region is called "FR." FR1 region between the N-terminus and CDR1, FR2 region between CDR1 and CDR2, FR3 region between CDR2 and CDR3, and FR4 region between CDR3 and the carboxyl terminus (C-terminus) of the variable region are present both in the heavy chain variable region and the light chain variable region. A humanized antibody can be obtained by humanizing at least one region among these regions or all. About 90% or more of the amino acid sequence of a humanized antibody is typically of human origin, but the percentage is not limited to this. The humanized antibody can be prepared in accordance with a known method.

In an embodiment, the antibody is preferably a human antibody. The human antibody refers to an antibody whose entire structure, including the variable regions, is originated from a human. The human antibody may also be referred to as a "completely humanized antibody." The human antibody can be prepared, for example, by a human antibody gene cloning method using phage display, a preparation method involving immunization against a human-type transgenic mouse, immortalization of a human-antibody-producing cell with EB virus, or a method in which a fusion partner is fused with a human peripheral blood mononuclear cell.

In an embodiment, the antibody preferably contains a constant region. The structure of the antibody including a constant region can be any structure. For example, the antibody may be an immunoglobulin that is a combination of two structures each composed of a single heavy chain having a heavy chain variable region and a heavy chain constant region and a single light chain having a light chain variable region and a light chain constant region; or the antibody may also have the structure called "Fab," "F(ab') 2," "minibody," "scFv-Fc," or any combination thereof. In an embodiment, the antibody may be a chimeric antigen receptor, a chimeric antigen receptor T cell, a chimeric antigen receptor NK cell, or the like described later.

"Fab" contains a fragment of a heavy chain containing the heavy chain variable region and CH1 in the heavy chain constant region and a light chain containing the light chain variable region and the light chain constant region (CL), and the heavy chain variable region and the light chain variable region are aggregated by non-covalent, intermolecular interaction described above, or bound to each other through the disulfide bond. In Fab, CH1 and CL may be disulfide-bonded by the thiol groups of the respective cysteine residues.

"$F(ab')_2$" refers to the structure that contains a pair of Fabs in which CH1 of one Fab is disulfide-bonded to CH1 of another Fab by thiol groups of the respective cysteine residues.

"Minibody" refers to the structure in which two fragments each containing CH3 bound to a heavy chain variable region constituting scFV are aggregated between CH3-CH3 by non-covalent, intermolecular interaction.

"scFv-Fc" refers to the structure in which two antibody fragments each containing scFv, CH2, and CH3 are aggregated between CH3-CH3 by non-covalent, intermolecular interaction, as with the minibody, and the fragments are disulfide-bonded through thiol groups of the cysteine residues contained in respective CH3.

A variety of antibodies containing these constant regions can be prepared by any method known in the art, as with the antibody containing none of these constant regions described above. Fab can also be obtained, for example, by breaking down IgG (immunoglobulin) using a protease such as papain. $F(ab')_2$ can also be obtained by breaking down IgG using a protease such as pepsin.

In an embodiment, the antibody is preferably an immunoglobulin. The class of the immunoglobulin is not particularly limited. Examples include IgA, IgD, IgE, IgG, and IgM, and a subclass thereof. In an embodiment, the antibody is preferably IgG. For example, if the antibody is mouse-originated IgG, IgG2 is preferable among the four subclasses.

Examples of the structure of the antibody containing a constant region include a heavy chain having the amino acid sequence of SEQ ID NO: 5 and/or a light chain having the amino acid sequence of SEQ ID NO: 10. The amino acid sequence of SEQ ID NO: 5 is an amino acid sequence containing the heavy chain variable region of the R8H283 antibody and the heavy chain constant region of the IgG antibody. The amino acid sequence of SEQ ID NO: 10 contains the amino acid sequence of the light chain variable region of the R8H283 antibody and the amino acid sequence of the light chain constant region of the IgG antibody. In an embodiment, the antibody contains a heavy chain having the amino acid sequence of SEQ ID NO: 5 and a light chain having the amino acid sequence of SEQ ID NO: 10.

When the antibody contains at least one amino acid sequence selected from the group consisting of SEQ ID NOs: 1 to 10, the at least one amino acid sequence may contain any mutation as long as the epitope for the antibody is present within the region affected by the presence of an N-glycan on human CD98hc. In an embodiment, there is preferably no mutation in the hypervariable region or complementarity-determining region of the antibody. This is because a mutation in the hypervariable region or the complementarity-determining region is considered to typically affect the epitope. Thus, in an embodiment, a mutation in the variable region is preferably present in the heavy chain FR region and light chain FR region. It is also possible to adjust the ADCC activity and/or CDC activity of the antibody by inserting a mutation into the constant region.

The number of mutations introduced into the at least one amino acid sequence selected from the group consisting of SEQ ID NOs: 1 to 10 (amino acid residue conversion) is not particularly limited. In an embodiment, the identity of the amino acid sequence before mutation introduction with the amino acid sequence after mutation introduction is at least 70%, preferably at least 75%, preferably at least 80%, preferably at least 85%, preferably at least 90%, preferably at least 958, preferably at least 96%, preferably at least 97%, preferably at least about 98%, and preferably at least 998. The identity percentage is determined by rounding off.

The identity of amino acids can be calculated with a commercially available analytical tool or an analytical tool available through the Internet (e.g., software such as FASTA, BLAST, PSI-BLAST, or SSEARCH). For example, the main initial conditions generally applied for a BLAST search are as described below. Specifically, a value (%) of the identity of an amino acid sequence with another sequence can be calculated by performing a search on Advanced BLAST 2.1 with blastp for the program, with the expect value set to 10, all filters turned off, BLOSUM62 used for matrix, the gap existence cost, per residue gap cost, and lambda ratio set to 11, 1, and 0.85 (default values), respectively, and other various parameters also set to default values.

The mutation introduced into an amino acid sequence described above is, for example, substitution, deletion, or insertion. Specific introduction of mutations is not particularly limited, as long as it can be achieved using a conventional method. The substitution of an amino acid is preferably a conservative substitution. Conservative substitution refers to replacement of an amino acid residue by another amino acid residue having a side chain similar to the side chain of the replaced amino acid residue.

Specific conservative amino acid substitutions include the following: substitution between amino acid residues each having a basic side chain, such as lysine, arginine, and histidine; substitution between amino acid residues each having an acidic side chain, such as aspartic acid and glutamic acid; substitution between amino acid residues each having an uncharged polar side chain, such as glycine, asparagine, glutamine, serine, threonine, tyrosine, and cysteine; substitution between amino acid residues each having a nonpolar side chain, such as alanine, valine, leucine, isoleucine, proline, phenylalanine, methionine, and tryptophan; substitution between amino acid residues each having a β-branched side chain, such as threonine, valine, and isoleucine; and substitution between amino acid residues each having an aromatic side chain, such as tyrosine, phenylalanine, tryptophan, and histidine.

In an embodiment, the antibody preferably has cytotoxic activity. Cytotoxic activity refers to the activity by which the antibody binds to a cell to kill the cell (or proliferative arrest), and its mechanism is not particularly limited. For example, the cytotoxic activity is produced by complement-dependent cytotoxicity (CDC), antibody-dependent cellular cytotoxicity (ADCC), apoptosis-inducing action, or survival signaling inhibition by blocking a ligand bond, or by a combination of two or more of these.

ADCC activity refers to the activity by which a cell having cytotoxic activity, such as an NK cell expressing a receptor specific to the constant region of an antibody, is recruited to the vicinity of the antibody to damage another cell to which the antibody has bound by the action of the cell etc. CDC activity refers to the activity by which an antibody recruits complements to its vicinity to damage a cell to which the antibody is bound by the action of complements. ADCC activity and CDC activity can be adjusted by adding a mutation to the constant region of the antibody.

For example, if the constant region is human IgG1, ADCC activity can be increased by introducing at least one of the following mutations (substitutions): S239D, 1332E, S239D/1332E, S239D/I332E/A330L, S298A, K334A, S298A/K334A, S298A/E333A/K334A etc. ADCC activity can be increased by introducing these mutations. Here, "S239D" indicates that serine(S) at position 239 of the constant region is replaced by aspartic acid (D). The same applies to other substitutions.

When the constant region is human IgG1, ADCC activity can be reduced, for example, by introducing at least one of the following mutations (substitutions): V234A/G237A, H268Q/V309L/A330S/P331S.

Regarding CDC activity, when the constant region is human IgG1, CDC activity can be increased, for example, by introducing at least one of the following mutations (substitutions): S267E, H268F, S324T, S267E/H268F, S267E/S324T, H268F/S324T, and S267E/H268F/S324T.

ADCC Activity Measurement Method

ADCC activity can be measured in accordance with the method of Brunner K. T. et al. (Brunner, K. T. et al., Immunology, 1968. 14:181-96). For example, a myeloma cell is cultured in an RPMI1640 medium containing 10% FCS, and the number of cells is adjusted to $0.5\times10^4$ to $1.0\times10^4$. A suitable amount of $Na_2{}^{51}CrO_4$ is then added thereto, and reacted at 37° C. for 1 hour, followed by labeling the cell with $^{51}Cr$. The washed result is then used as a target cell. Usable effector cells include those obtained by culturing the bone marrow cell of a SCID mouse in RPMI1640 that contains 10% FBS, 10 ng/ml mouse GM-CSF, and 40 IU/ml human IL2 for 6 days, or the like. A test antibody or its isotype antibody as control is added to a 96-well plate to give a final concentration of 0.05 to 10 μg/mL, and a target cell ($1.0\times10^4$) and an effector cell ($5\times10^5$) are further added thereto. A reaction is performed at 37° C. for 4 hours, and after centrifugation, $^{51}Cr$ released into the supernatant is measured with a γ-counter. ADCC activity can be determined from the following equation.

ADCC Activity={([$^{51}$Cr release from a target cell]−[voluntary $^{51}$Cr release in the absence of an antibody])/([a maximum $^{51}$Cr release amount achieved by adding 1% TRITON X-100 (a surfactant)]−[voluntary $^{51}$Cr release in the absence of an antibody])}×100

CDC Activity Measurement Method

CDC activity can also be measured in accordance with the method of Brunner K. T. et al. (Brunner, K. T. et al., Immunology, 1968. 14:181-96). For example, a myeloma cell that is a target cell is cultured in an RPMI1640 medium containing 10% FCS, and the number of cells is adjusted to $0.5\times10^4$ to $1.0\times10^4$. A suitable amount of $Na_2{}^{51}CrO_4$ is then added thereto, and reacted at 37° C. for 1 hour, followed by labeling the cell with $^{51}Cr$. The washed result is used as a target cell. A test antibody or its isotype antibody as control suspended in an RPMI1640 medium to which cow fetal serum has been added is added to a 96-well plate to give a final concentration of 0.5 to 50 μg/mL. Subsequently, the target cell and complements are added thereto, followed by reaction for 1.5 hours. The reaction solution is separated by centrifugation, and $^{51}Cr$ that has been released into the supernatant is measured with a γ-counter. CDC activity can be determined from the following equation.

CDC Activity={([$^{51}$Cr release from a target cell]−[voluntary $^{51}$Cr release in the absence of an antibody])/([a maximum $^{51}$Cr release amount achieved by adding 1% TRITON X-100 (a surfactant)]−[voluntary $^{51}$Cr release in the absence of an antibody])}×100

An antibody having cytotoxic activity can be obtained by assessing the presence or absence of cytotoxic activity using the method mentioned above, and selecting an antibody having the activity.

The antibody having cytotoxic activity is useful because such an antibody can be used alone for treating a disease (e.g., malignant tumor).

In an embodiment, the antibody may be a multispecific antibody whose epitope is present in the region affected by the presence of an N-glycan on CD98hc, and may specifically bind to other antigens. Other antigens can be freely selected depending on the purpose, and are not particularly limited.

The multispecific antibody can be prepared suitably using a method known in the art. For example, a multispecific antibody can be obtained by the following procedure.

(1) Prepare hybridomas that produce an antibody whose epitope is present in the region affected by the presence of an N-glycan on CD98hc.

(2) Separately prepare hybridomas using an antibody-producing cell, such as B cells obtained from an animal immunized with another antigen.

(3) Prepare hybridomas by subjecting these two kinds of hybridomas to cell fusion (a bispecific antibody is also referred to as "quadroma").

(4) Screen for a hybridoma that produces the target multispecific antibody from hybridomas prepared in step (3).

A bispecific antibody can also be obtained by the following procedure.

(a) Prepare an antibody in the form of $F(ab')_2$ whose epitope is present in the region affected by the presence of an N-glycan on CD98hc.

(b) Separately prepare an antibody in the form of $F(ab')_2$ that specifically binds to another antigen.

(c) Treat the two kinds of antibodies in the form of $F(ab')_2$ obtained in steps (a) and (b) with a reducing agent such as DTT and further treat either of the treated products with an Ellman's reagent.

(d) Mix the treated antibodies in the form of $F(ab')_2$ obtained in step (c) to perform a reaction.

The antibody may have any other substance bound to it. Examples of other substances include substances having cytotoxic activity, enzymes, tags, and immunomodulators.

Cytotoxic activity can be added to an antibody by allowing a substance having cytotoxic activity to bind to the antibody. Cytotoxin is a substance having cytotoxic activity (e.g., cell-killing activity and/or cell growth inhibiting activity), and the type of cytotoxin is not particularly limited as long as it has this activity. Examples include substances known as anticancer agents.

Specific examples of cytotoxin include the following: alkylating agents, such as cyclophosphamide hydrate, ifosfamide, thiotepa, busulfan, melphalan, nimustine hydrochloride, ranimustine, dacarbazine, and temozolomide; antimetabolites, such as methotrexate, pemetrexed sodium hydrate, fluorouracil, doxifluridine, capecitabine, tegafur, cytarabine, gemcitabine hydrochloride, fludarabine phosphate ester, nelarabine, cladribine, and calcium levofolinate; antibiotics, such as doxorubicin hydrochloride, daunorubicin hydrochloride, pirarubicin, epirubicin hydrochloride, idarubicin hydrochloride, aclarubicin hydrochloride, amrubicin hydrochloride, mitoxantrone hydrochloride, mitomycin C, actinomycin D, bleomycin hydrochloride, peplomycin hydrochloride, zinostatin stimalamer, and calicheamicin; microtubule inhibitors, such as vincristine sulfate, vinblastine sulfate, vindesine sulfate, and paclitaxel; aromatase inhibitors, such as anastrozole, exemestane, letrozole, and fadrozole hydrochloride hydrate; platinum-based drugs, such as cisplatin, carboplatin, nedaplatin, and oxaliplatin; topoisomerase inhibitors, such as irinotecan hydrochloride hydrate, nogitecan hydrochloride, etoposide, and sobuzoxane; corticosteroids, such as prednisolone and dexamethasone; thalidomide and its derivative lenalidomide; bortezomib, which is a protease inhibitor; and radioisotopes, such as 90-Ittrium. Of these, calicheamicin, melphalan, vincristine sulfate, doxorubicin hydrochloride, prednisolone, dexamethasone, thalidomide, lenalidomide, and bortezomib are preferable, and calicheamicin that has demonstrated excellent binding to antibodies is more preferable. These cytotoxins are all commercially available, and one or a combination of two or more of these can be suitably selected.

A cytotoxin and an antibody can be bound to each other by any method. For example, a cytotoxin can be bound to a functional group such as the amino group, thiol group, guanidyl group, hydroxyl group, or carboxyl group of the side chain of an amino acid residue of an antibody through a linker.

The antibody may be either a polyclonal antibody or a monoclonal antibody. In an embodiment, the antibody is preferably a monoclonal antibody.

The anti-human CD98hc antibody described above can be produced by any technique known in the art with reference to the information disclosed in this specification. In a preferable embodiment, an antibody recognizing an epitope that contains an N-glycosylation site of human CD98hc and that is exposed by inhibiting N-linked glycosylation can be obtained using a peptide fragment or a protein (e.g., CD98ch) containing the amino acid sequence of SEQ ID NO: 22 (preferably the amino acid sequence of SEQ ID NO: 23), or a cell that expresses the protein as an immunogen. In an embodiment, a preferable immunogen is human/animal chimera CD98ch composed of the amino acid sequence of SEQ ID NO: 22 (preferably the amino acid sequence of SEQ ID NO: 23) and other amino acid sequences of CD98hc originated from a mammal other than a human, such as a mouse, as well as its fragment, or a cell that expresses it. The mammal other than a human can be any mammal, and is not particularly limited; however, a mammal used as an immunized animal is preferable. Examples of immunized animals include mice, rats, hamsters, rabbits, cows, goats, monkeys, swine, and ostriches. In an embodiment, a preferable immunized animal is a mouse. By immunizing these animals with such a human/animal chimera CD98ch as an immunogen, only the region of the amino acid sequence of SEQ ID NO: 22 (preferably the amino acid sequence of SEQ ID NO: 23) becomes an exogenous protein for the immunized animal, and an antibody that recognizes this region as an epitope is efficiently induced.

Human/animal chimera CD98hc can be obtained by any technique with reference to the information of known amino acid sequences and gene sequences of CD98hc of various animals. In an embodiment, CD98hc for use as an immunogen preferably has no N-glycan added thereto. This CD98hc can be obtained, for example, by replacing an asparagine residue (e.g., the asparagine residue at position 405) to which an N-glycan of CD98hc binds by another amino acid residue (e.g., glutamine). In an embodiment, the immunogen for obtaining the antibody is preferably a cell that expresses human/animal (e.g., a mouse) chimera CD98hc or its fragment. The cell can be of any type, and is not particularly limited; however, the cell is preferably originated from the same animal species as the immunized animal. This prevents the cell in the immunized animal from being recognized as an exogenous cell, thus efficiently inducing an antibody that recognizes the region of the amino acid sequence of SEQ ID NO: 22 (preferably the amino acid sequence of SEQ ID NO: 23) as an epitope.

Immunization to prepare an immunized animal is typically performed every 3 to 10 days multiple times. The number of cells used for one immunization time can be any number. However, $10^3$ to $10^8$ cells are typically administered. In the use of a protein or its fragment as an immunogen, an animal is typically immunized with 1 to 100 μg. Antibody-producing cells are collected from the spleen or lymph node of the immunized animal that underwent immunization multiple times, and the cell that produces the target antibody is cloned, thereby obtaining a monoclonal antibody. Cloning can be performed by fusing an antibody-producing cell with a suitable cell line (e.g., a myeloma cell) to prepare a hybridoma and measuring the desired binding capability of the antibody produced by the hybridoma. Measurement of the binding capability can be performed using a known method, such as FACS, ELISA, RIA, and EIA.

The antibody obtained in this manner specifically recognizes the region affected by the presence of an N-glycan on human CD98hc, and thereby specifically recognizes myeloma cells, myeloma progenitor cells, and other tumor cells. Thus, the antibody is useful for treatment or prevention of tumors etc. The type of tumor is not particularly limited, and is a malignant tumor, including solid cancer and blood cancer. Examples of solid cancer include lung cancer, colorectal cancer, ovarian cancer, breast cancer, brain tumor, stomach cancer, liver cancer, tongue cancer, thyroid cancer, kidney cancer, prostate cancer, uterine cancer, osteosarcoma, chondrosarcoma, and rhabdomyosarcoma. Examples of blood cancer include leukemia, diseases involving neoplastic growth of plasma cells (e.g., multiple myeloma), and malignant lymphoma. In an embodiment, leukemia is preferably lymphatic leukemia.

3. Polynucleotide

A polynucleotide encoding the antibody described in section 2 above (which hereinafter may be referred to as "antibody A") is provided. The term "polynucleotide" refers to a high-molecular compound composed of linearly polymerized nucleotides (e.g., ribonucleotides or deoxyribonucleotides). The polynucleotide may be a single-stranded or double-stranded chain.

The base sequences of polynucleotides encoding the amino acid sequences of the hypervariable region, variable region, heavy chain, and light chain of the R8H283 antibody are indicated as SEQ ID NOS: 11 to 20. Table 2 below shows the correspondence of these sequences.

TABLE 2

| | Region | Amino Acid Sequence | Base Sequence |
|---|---|---|---|
| Heavy Chain | CDR-H1 | SEQ ID NO: 1 | SEQ ID NO: 11 |
| | CDR-H2 | SEQ ID NO: 2 | SEQ ID NO: 12 |
| | CDR-H3 | SEQ ID NO: 3 | SEQ ID NO: 13 |
| | Variable Region | SEQ ID NO: 4 | SEQ ID NO: 14 |
| | Total Length | SEQ ID NO: 5 | SEQ ID NO: 15 |
| Light Chain | CDR-L1 | SEQ ID NO: 6 | SEQ ID NO: 16 |
| | CDR-L2 | SEQ ID NO: 7 | SEQ ID NO: 17 |
| | CDR-L3 | SEQ ID NO: 8 | SEQ ID NO: 18 |
| | Variable Region | SEQ ID NO: 9 | SEQ ID NO: 19 |
| | Total Length | SEQ ID NO: 10 | SEQ ID NO: 20 |

In an embodiment, the polynucleotide comprises at least one base sequence selected from the group consisting of SEQ ID NOs: 11 to 20 (the combination of two or more sequences can be any combination). In a preferable embodiment, the polynucleotide comprises at least one base sequence selected from the group consisting of SEQ ID NOs: 11 to 13 (preferably 2 or more, and more preferably all) and/or at least one base sequence selected from the group consisting of SEQ ID NOs: 16 to 18 (preferably 2 or more, and more preferably all). In a preferable embodiment, the polynucleotide comprises the base sequences of SEQ ID NOs: 11 to 13 and the base sequences of SEQ ID NOs: 16 to 18. In a preferable embodiment, the polynucleotide comprises the base sequence of SEQ ID NO: 14 and/or the base sequence of SEQ ID NO: 19. In another preferable embodiment, the polynucleotide comprises the base sequence of SEQ ID NO: 15 and/or the base sequence of SEQ ID NO: 20.

The base sequence of the polynucleotide is not necessarily a complete match with SEQ ID NOs: 11 to 20 as long as the polynucleotide encodes antibody A. For example, the base sequence of the polynucleotide may have at least 80%, preferably, at least 85%, preferably at least 90%, preferably at least 95%, preferably at least 98%, and preferably at least 99% identity with SEQ ID NOs: 11 to 20. The identity can be calculated using a commercially available analytical tool or an analytical tool available through telecommunication lines (the Internet). Specifically, the value (%) of the homology of nucleotide sequences can be calculated, for example, by performing a search using blastn for the program in Advanced BLAST 2.1, with various parameters set to default values. The frequency of codon usage for the polynucleotide may be optimized depending on the type of the vector or cell expressing it.

The state of the polynucleotide is not particularly limited; for example, the polynucleotide may be an isolated polynucleotide or a polynucleotide incorporated in a vector. The type and use of the vector are not particularly limited. For example, the vector can be a plasmid vector or a virus vector (e.g., adenovirus or retrovirus). The vector can be, for example, a vector for cloning or for expression. The vector for expression includes vectors for prokaryotic cells, such as *Escherichia coli*, and actinomycete, and vectors for eukaryotic cells, such as yeast cells, insect cells, and mammalian cells. The polynucleotide may have any modification; for example, the polynucleotide may suitably have a base sequence encoding a signal peptide at the 5' terminus.

4. Host Cell

A host cell comprising the polynucleotide encoding antibody A described above is provided. The form in which a host cell contains the polynucleotide is not particularly limited. For example, the host cell may contain the polynucleotide in the form of vector or may contain the polynucleotide integrated in the intracellular genomic DNA of the host organism.

The host cell may be of any type and is not particularly limited. For example, the host cell can be a eukaryotic cell, such as a yeast cell, an insect cell, and a mammal cell, and a prokaryotic cell, such as *Escherichia coli* and actinomycete. In an embodiment, the host cell is preferably a eukaryotic cell; for example, the host cell is preferably a T cell or NK cell.

The host cell comprising the polynucleotide encoding the antibody described above can be obtained, for example, by incorporating the polynucleotide (e.g., in the form of vector) into a host cell.

5. Chimeric Antigen Receptor

Provided are a chimeric antigen receptor (CAR) recognizing an epitope that contains an N-glycosylation site of human CD98hc and that is exposed by inhibiting N-linked glycosylation, a chimeric antigen receptor whose epitope is present in the region affected by the presence of an N-glycan on human CD98hc, an anti-human CD98hc chimeric antigen receptor whose affinity for human CD98hc is increased by removing a sugar chain bound to human CD98hc, an anti-human CD98hc chimeric antigen receptor whose affinity for a CD98hc variant in which the amino acid residues at positions 395 to 397 of human CD98hc are replaced by amino acid residues of mouse-originated CD98hc is equivalent to its affinity for the mouse-originated CD98hc, and an anti-human CD98hc chimeric antigen receptor whose affinity for a CD98hc variant in which the amino acid residues at positions 400 and 401 of human CD98hc are replaced by amino acid residues of mouse-originated CD98hc is equivalent to its affinity for the mouse-originated CD98hc etc. The chimeric antigen receptor is typically a T-cell receptor (TCR)-like artificial protein and is known as a protein constructed such that an antigen-recognition site expressed on the cell membrane of a T cell (corresponding to the extracellular domain) is replaced by a desired antigen-recognition site, and that T-cell functions such as cytotoxic activity can be more effectively produced. The chimeric antigen receptor typically has its single-chain antibody (scFv) composed of a light chain variable region bound to a heavy chain variable region in tandem on the N-terminus side and its T-cell receptor (TCR) ζ chain on the C-terminus side. A T cell or the like expressing the chimeric antigen receptor recognizes an antigen in its scFv domain, and then intracellularly transfers a recognition signal through the ζ chain. The chimeric antigen receptor preferably contains a costimulatory molecule (e.g., CD28 and/or 4-1BB) between the scFv and the ζ chain in order to increase the activation of T cell.

The following characteristics are all explained by the description of antibody A: "an epitope that contains an N-glycosylation site of human CD98hc and that is exposed by inhibiting N-linked glycosylation," "the region affected by the presence of an N-glycan on human CD98hc," "affinity for human CD98hc is increased by removing a sugar chain bound to human CD98hc," "affinity for a CD98hc variant in which the amino acid residues at positions 395 to 397 of human CD98hc are replaced by amino acid residues of mouse-originated CD98hc is equivalent to its affinity for the mouse-originated CD98hc," and "affinity for a CD98hc variant in which the amino acid residues at positions 400 and 401 of human CD98hc are replaced by amino acid residues of mouse-originated CD98hc is equivalent to its affinity for the mouse-originated CD98hc." Thus, in an embodiment, the epitope for the chimeric antigen receptor is preferably present in the region of the amino acid sequence represented by SEQ ID NO: 22 of CD98hc. In another preferable embodiment, the epitope for the chimeric antigen receptor is preferably present in the region of the amino acid sequence represented by SEQ ID NO: 23. In an embodiment, the epitope for the chimeric antigen receptor is preferably present in the region at positions 365 to 376 and the region at positions 395 to 409 of human CD98hc. In an embodiment, the epitope for the chimeric antigen receptor preferably contains the amino acid residues at positions 374, 375, 395, 396, 397, 400, and 401 of human CD98hc.

In another embodiment, the epitope for the chimeric antigen receptor is preferably identical to the epitope for the R8H283 antibody. Thus, scFv of the chimeric antigen receptor preferably contains the heavy chain variable region and light chain variable region of the antibody described above. More specifically, scFv of the chimeric antigen receptor preferably has the following structure:

- a heavy chain variable region comprising
  - a heavy chain CDR1 comprising an amino acid sequence containing the amino acid sequence of SEQ ID NO: 1,
  - a heavy chain CDR2 comprising an amino acid sequence containing the amino acid sequence of SEQ ID NO: 2, and/or
  - a heavy chain CDR3 comprising an amino acid sequence containing the amino acid sequence of SEQ ID NO: 3, and/or
- a light chain variable region comprising
  - a light chain CDR1 comprising an amino acid sequence containing the amino acid sequence of SEQ ID NO: 6,
  - a light chain CDR2 comprising an amino acid sequence containing the amino acid sequence of SEQ ID NO: 7, and/or
  - a light chain CDR3 comprising an amino acid sequence containing the amino acid sequence of SEQ ID NO: 8.

In a preferable embodiment, scFv of the chimeric antigen receptor contains a heavy chain variable region containing the amino acid sequence of SEQ ID NO: 4 and/or a light chain variable region containing the amino acid sequence of SEQ ID NO: 9.

The chimeric antigen receptor preferably has a structure in which the following are arranged from its N-terminus in order: a scFv domain composed of a light chain variable region and a heavy chain variable region of the antibody bound in tandem described above; a spacer sequence; a transmembrane domain; a costimulator; and an intracellular domain of TCR.

The scFv domain may contain a spacer sequence of, for example, about 10 to 25 amino acid residues between the heavy chain variable region and the light chain variable region. Such a spacer sequence may be identical to or different from the spacer sequence provided between the scFv domain and the transmembrane domain.

The length of the spacer sequence provided between the scFv domain and the transmembrane domain and the types of the amino acid residues constituting the spacer sequence are not limited, as long as the function of the chimeric antigen receptor is not hindered. For example, the spacer sequence can be designed to contain about 10 to 25 amino acid residues.

The type of the transmembrane domain is not limited, as long as the function of the chimeric antigen receptor is not hindered. For example, CD28, 4-1BB, and the like that are expressed in T cells or other cells can be used. A mutation may suitably be introduced into these transmembrane domains, as long as the function of the chimeric antigen receptor is not hindered.

The costimulator is not particularly limited, as long s it is a costimulator contained in T cells or the like. For example, at least one member suitably selected from the group consisting of OX40, 4-1BB, and CD28 may be used. A mutation may suitably be introduced into these costimulators, as long as the function of the chimeric antigen receptor is not hindered.

The intracellular domain of TCR may be, for example, an intracellular domain originated from CD3, which may also be called a TCR ζ chain. A mutation may suitably be introduced into CD3, as long as the function of the chimeric antigen receptor is not hindered. When a mutation is introduced into CD3, it is preferable to perform the introduction such that ITAM (an immunoreceptor tyrosine-based activation motif) is contained.

The chimeric antigen receptor can be produced with reference to, for example, the method disclosed in Non-patent Literature 2 to 4.

A polynucleotide encoding the chimeric antigen receptor is provided. The base sequence of the polynucleotide can be any sequence and is not particularly limited, as long as the sequence encodes the chimeric antigen receptor. The state of the polynucleotide is not particularly limited; for example, the polynucleotide may be an isolated polynucleotide or a polynucleotide incorporated in a vector. The description of the polynucleotide encoding the antibody also applies to the polynucleotide encoding the chimeric antigen receptor.

A host cell comprising the polynucleotide encoding the chimeric antigen receptor is provided. The description of the host cell comprising the polynucleotide encoding the antibody also applies to the host cell comprising the polynucleotide encoding the chimeric antigen receptor. The host cell can be of any type; however, a cell having cytotoxic activity is preferable. Examples of the cell having cytotoxic activity include T cells, NK cells, and K cells, with killer T cells (which is also referred to as "cytotoxic T cells" or "CTL") being preferable.

The host cell may be in the state of expressing the polynucleotide encoding the chimeric antigen receptor, or in the state of not expressing the polynucleotide. When the polynucleotide encoding the chimeric antigen receptor is being expressed in the host cell, the scFv domain constituting the chimeric antigen receptor is preferably exposed on the outside of the cell, and the transmembrane domain, the costimulator, and the intracellular domain of TCR are preferably present in the cell membrane or inside the cell.

When the scFv domain recognizes its epitope, the scFv domain intracellularly activates a signal for evoking the cytotoxic activity through the transmembrane domain and costimulator. In conjunction with this, the cell mounts attacks against other cells or tissues expressing the epitope or exerts its cytotoxic activity on the cells or tissues.

When a cell exhibiting such a function is CTL, this cell is called a "chimeric antigen receptor T cell" ("CAR-T cell"). Cells that have potential to exhibit this cytotoxic activity, such as NK cells, also exhibit cytotoxic activity when their scFv domain is bound to their epitope, as with the chimeric antigen receptor T cell.

Thus, a host cell comprising the polynucleotide encoding the chimeric antigen receptor (in particular, host cells having cytotoxic activity) is useful as an active ingredient of pharmaceutical compositions. A host cell comprising the polynucleotide encoding the chimeric antigen receptor (e.g., CAR-T cell) can be produced with reference to, for example, the method disclosed in Non-patent Literature 2 to 4.

Such CAR-T cells recognize an epitope that contains an N-glycosylation site of human CD98hc and that is exposed by inhibiting N-linked glycosylation to thereby specifically recognize myeloma cells, myeloma progenitor cells, and other tumor cells; thus, these CAR-T cells are useful for treatment or prevention of tumors or the like. The type of tumor is not particularly limited, and includes solid cancer and blood cancer. Examples of solid cancer include lung cancer, colorectal cancer, ovarian cancer, breast cancer, brain tumor, stomach cancer, liver cancer, tongue cancer, thyroid cancer, kidney cancer, prostate cancer, uterine cancer, osteosarcoma, chondrosarcoma, and rhabdomyosarcoma. Examples of blood cancer include leukemia, diseases involving neoplastic growth of plasma cells (e.g., multiple myeloma), and malignant lymphoma. In an embodiment, leukemia is preferably lymphatic leukemia.

6. Pharmaceutical Composition and Treatment Method

A pharmaceutical composition comprising antibody A, a CAR-T cell, a CAR-NK cell, or the like and a treatment or prevention method of disease using antibody A, a CRT-T-cell, a CAR-NK cell, or the like are provided.

The content of the antibody or the cell in the pharmaceutical composition can be suitably determined taking into consideration the type of the target disease, intended treatment effect, administration method, treatment period, patient's age, patient's body weight, etc. For example, the content of the antibody in the pharmaceutical composition can be about 0.001 parts by weight to 10 parts by weight based on the entire pharmaceutical composition taken as 100 parts by weight. The content of the cell in the pharmaceutical composition can be, for example, about 1 cell/mL to $10^4$ cell/mL.

The administration form of the pharmaceutical composition is not particularly limited, as long as a desired effect is achieved. The composition can be administered to mammals, including humans, through an administration route, either peroral administration or parenteral administration, (e.g., intravenous injection, intramuscular injection, subcutaneous administration, rectal administration, transdermal administration, and local administration). Because the active ingredient is an antibody or a cell, the preferable administration form is parenteral administration, and more preferably intravenous injection. The dosage form and production method of the composition for peroral administration or parenteral administration would be well known to a person skilled in the art, and the pharmaceutical composition in any dosage form can be produced in accordance with a conventional method by mixing the antibody or cell of the present invention with a pharmaceutically acceptable carrier and the like.

The dosage form of the composition for parenteral administration includes injectable drugs (e.g., drip-injectable drugs, intravenously injectable drugs, intramuscularly injectable drugs, subcutaneously injectable drugs, and intradermally injectable drugs), drugs for external use (e.g., ointments, cataplasms, and lotions), suppositories, inhalants, eye drops, eye ointments, nasal drops, ear drops, and liposome drugs. For example, an injectable drug can be prepared by dissolving the antibody or cell in injectable distilled water; and a solubilizing agent, a buffer, a pH adjuster, a tonicity agent, a soothing agent, a preservative, a stabilizer, and the like can be optionally added thereto. The pharmaceutical composition may be in the form of freeze-dried formulation, which will be prepared when used.

The pharmaceutical composition may further comprise other medicinal agent effective in treatment or prevention of diseases. The pharmaceutical composition may also optionally contain components such as a sterilizer, an antiphlogistic, a cellular stimulant, vitamins, and an amino acid.

For the carrier used in preparing a drug of the pharmaceutical composition, an excipient, a binder, a disintegrant, a lubricant, a colorant, and a flavoring agent typically used in the art can be used; and a stabilizer, an emulsifier, an absorption promoter, a surfactant, a pH adjuster, an antiseptic, an antioxidant, a filler, a moisture agent, a surface activation agent, a dispersant, a buffer, a preservative, a solubilizing agent, a soothing agent, and the like can also optionally be used.

The type of disease treated or prevented using the pharmaceutical composition is not particularly limited, as long as the treatment or prevention can be achieved. Examples of specific target diseases include tumors. The type of tumor is not particularly limited, and includes solid cancer and blood cancer. Examples of solid cancer include lung cancer, colorectal cancer, ovarian cancer, breast cancer, brain tumor, stomach cancer, liver cancer, tongue cancer, thyroid cancer, kidney cancer, prostate cancer, uterine cancer, osteosarcoma, chondrosarcoma, and rhabdomyosarcoma. Examples of blood cancer include leukemia, diseases involving neoplastic growth of plasma cells (e.g., multiple myeloma), and malignant lymphoma. In an embodiment, leukemia is preferably lymphatic leukemia. In an embodiment, a preferable disease is a disease that causes neoplastic growth of plasma cells. A "disease that causes neoplastic growth of plasma cells" is a disease characterized by abnormal neoplastic growth of plasma cells and an increase in abnormal protein secreted by the plasma cells. Examples of these diseases include multiple myeloma, plasma cell leukemia, plasmacytoma, H-chain disease, and systemic AL amyloidosis. In an embodiment, a preferable target disease is multiple myeloma.

The administration target (test subject) of the pharmaceutical composition is, for example, an animal having a disease described above or an animal with a potential to develop such a disease. A "potential to develop such a disease" can be determined, for example, by the diagnostic method described later. The animal is, for example, a mammal, and preferably a human.

The dose of the pharmaceutical composition can be determined by a clinical physician, taking into consideration various factors, such as administration route, the type of disease, the degree of symptoms, patient's age, gender, body weight, severity of disease, pharmacological findings such as pharmacokinetics and toxicological characteristics, use or non-use of drug delivery system, and whether the composition is administered as part of a combinational drug with other medicinal agents. For example, when the active ingredient is the antibody, the dose of the pharmaceutical composition can be about 1 μg/kg (body weight) to 10 g/kg (body weight) per day. When the active ingredient is the cell (VI), the dose can be about $10^4$ cell/kg (body weight) to $10^9$ cell/kg (body weight). The administration schedule of the pharmaceutical composition can also be determined taking into consideration the same factors as those for the dose. For example, the composition can be administered once every day to once every month in the daily dose described above.

As described above, the antibody, CAR-T cell, or CAR-NK cell can be used for producing the pharmaceutical composition.

7. Screening Method

A screening method for an active ingredient of the pharmaceutical composition for treatment or prevention of tumor is provided. This method comprises selecting a substance that specifically binds to the region affected by the presence of an N-glycan on CD98hc from a compound library (a candidate substance group). The type of tumor is as described above for the pharmaceutical composition.

The compound library is not particularly limited, and an existing library may be used. The compound library is preferably an antibody library, and it is preferable to use as a library hybridomas prepared using antibody-producing cells, such as B cells obtained from an animal immunized with a desired antigen. The desired antigen is not particularly limited, and is preferably, for example, CD98hc or its fragment (a fragment containing the region affected by the presence of an N-glycan on CD98hc).

The method for selecting a substance that specifically binds to the region affected by the presence of an N-glycan on CD98hc can be any method, and is not particularly limited. For example, two types of cells, a cell expressing the region affected by the presence of an N-glycan on CD98hc and a cell not expressing the region, are prepared. These two types of cell are identical except for the presence or absence of the expression of the region. Subsequently, a labeled test substance (e.g., fluorescent labeling) is added to both cells, and whether there is a bond between the cells and the test substance is measured by flow cytometry. A substance that only binds to the cell expressing the region has specific affinity for the region, and an antibody that does not so behave has no or low specific affinity for the region. The degree of the affinity of an antibody for the region can be measured based on the intensity of the fluorescence signal detected in flow cytometry.

In addition to the method using flow cytometry, immunoassay can also be used to measure the affinity. In this case, a microtiter plate is coated with the region purified, and a test substance is added to each well, followed by reaction. Subsequently, an antibody that can recognize the substance and that is labeled with an enzyme, a fluorescent substance, a luminescent substance, a radioactive substance, biotin, or the like is added thereto to allow the antibody to react with the substance. Thereafter, the affinity of the test substance for the region can be measured with the labeled antibody as an indicator.

The test substance is not particularly limited, as long as its affinity for the region affected by the presence of an N-glycan on CD98hc can be measured by these methods, but the test substance is preferably an antibody.

The screening method may comprise the step of selecting a substance having cytotoxic activity. Selection of a substance having cytotoxic activity is optional and is not particularly limited. For example, when a candidate substance is an antibody, the measurement method for ADCC activity and/or the measurement method for CDC activity described above may be used for the selection.

8. Diagnostic Method

A method for diagnosing whether a subject has a tumor is provided. This method comprises bringing the antibody described above into contact with a sample collected from a test subject. The type of tumor is as described above for the pharmaceutical composition.

The antibody specifically binds to an epitope that contains an N-glycosylation site of human CD98hc and that is exposed by inhibiting N-linked glycosylation to thereby specifically recognize myeloma progenitor cells, myeloma plasma cells, and other tumor cells. Thus, neoplastic plasma cells in a sample can be identified by allowing the antibody to act on the sample containing neoplastic plasma cells and detecting the antibody bound to a cell expressing the region corresponding to the epitope.

The sample is preferably a biological sample containing neoplastic plasma cells collected from a cancer patient (e.g., bone marrow, blood, and tumor mass), more preferably body fluid, and still more preferably blood. For easy detection, the antibody is preferably labeled (e.g., fluorescent dye or radioisotope). Identification of myeloma plasma cells may be performed using only the antibody or using a combination of the antibody with another antibody (e.g., anti-human CD38 monoclonal antibody or anti-CD48 monoclonal antibody). For example, a myeloma cell population can be easily identified by co-staining a sample collected from the bone marrow of a patient with myeloma with these antibodies labeled with fluorescence and separating cells in the sample by flow cytometry.

When myeloma progenitor cells and/or myeloma plasma cells are detected in a sample in this manner, the test subject is diagnosed with cancer (or as highly likely having cancer).

9. Kit

Kits comprising the antibody for different purposes are provided. For example, a kit may be for treatment or prevention of a tumor or for diagnosis of cancer. The type of tumor is as described above for the pharmaceutical composition.

The kit may comprise only the antibody, but may also comprise other components (e.g., other antibodies, a buffer solution, and a fluorescent dye), instruments, and a manual, depending on the intended use.

EXAMPLES

The following describes the present invention with reference to the Examples. However, the invention disclosed in this specification is not limited to the Examples.

1. Flow Cytometry and Sorting

In the following test, flow cytometry for cell selection was performed in accordance with the following procedure. Bone marrow mononuclear cells collected from the ilium of a myeloma patient, from whom informed consent had been obtained, were suspended in an ACK solution (150 mM $NH_4Cl$, 10 mM $KHCO_3$), and allowed to stand at 4° C. for 3 minutes, followed by removing red blood cells. The result was washed with PBS (phosphate-buffered saline) containing 2% fetus cow serum, and blocking was performed in PBS containing 10% human AB serum at 4° C. for 20 minutes to prevent an antibody from non-specifically binding to it. Thereafter, each antibody labeled with a fluorescent dye (see the below) was added thereto, and staining was performed at 4° C. for 30 minutes, followed by washing with PBS. The cells were suspended in PBS containing 1 μg/ml propidium iodide (PI) and subjected to flow cytometry analysis. The analysis and cell sorting were performed with an FACS Aria cell sorter (Becton Dickinson Immunocytometry System). For staining of the cells, the following monoclonal antibodies were suitably selected and used.

APC-conjugated anti-CD34 antibody (BD Pharmingen), Cy7-PE-conjugated anti-CD34 antibody (BD Pharmingen), Cy7-APC-conjugated anti-CD19 antibody (Biolegend), FITC-conjugated anti-CD38 antibody (eBioscience), APC-conjugated anti-CD138 antibody (Biolegend), Cy7-PE-conjugated anti-CD3 antibody (Biolegend), FITC-conjugated anti-CD14 antibody (BD Pharmingen), Cy7-PE conjugated human CD45 antibody (Biolegend)

2. Preparation of Library of Monoclonal Antibodies That Bind to Myeloma Cell Line But Do Not Bind to Healthy Individual Peripheral Blood In antibody treatment of multiple myeloma, it is preferable to use an antibody that binds to myeloma cells but not normal blood cells. Thus, an antibody useful in treating multiple myeloma was identified by the following method.

First, 10,000 or more clones of monoclonal antibodies that bind to a variety of myeloma cell lines were prepared in accordance with the following technique. Footpads of Balb/c mice were immunized with 6 types of human myeloma cell lines (MM1s, RPMI8226, INA6, U266, OPM2, and KMS121BM) as antigens two times a week for 2 to 3 weeks. Thereafter, lymph nodes below the knees were removed, and cell suspensions were prepared, followed by cell fusion with a SP2/0 mouse myeloma cell line. The cell fusion was performed by a method using polyethyleneglycol (PEG method). The cells were cultured in a hypoxanthine-aminopterin-thymidine medium (HAT medium) to select hybridomas. Finally, the hybridomas were fused to the myeloma cell lines used for immunization using the culture supernatant of the hybridomas, and a supernatant containing antibodies that do not bind to mononuclear cells originated from peripheral blood of a healthy individual was selected by flow cytometry. The resulting candidates for myeloma-cell-specific-antibody were about 200 clones, and these were grown and cryopreserved.

Figure 2:
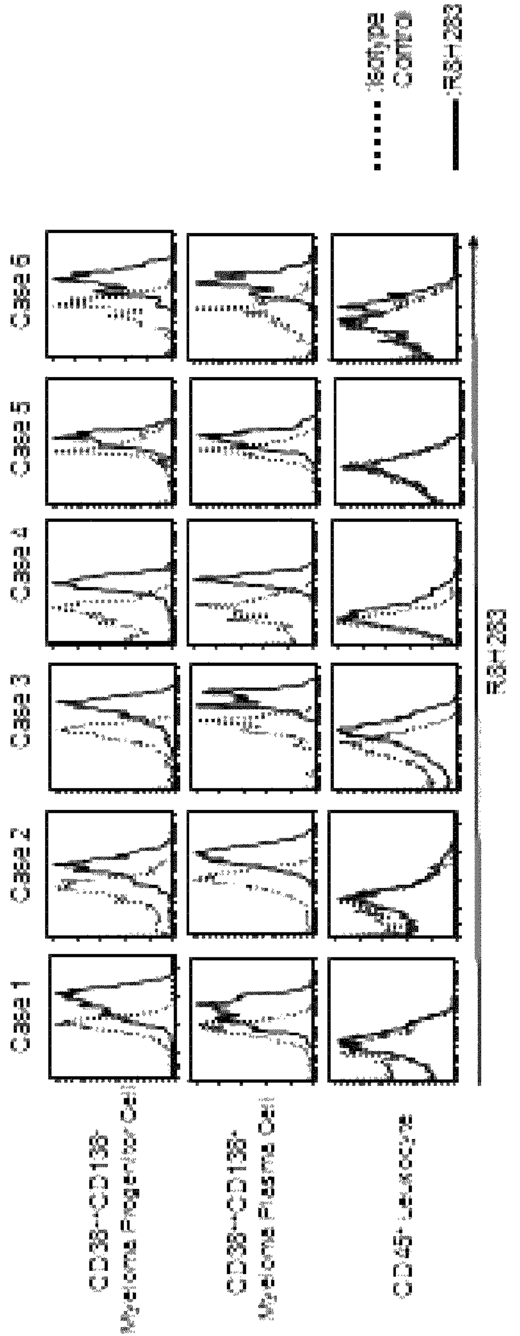
FIG. 2 shows the binding of the R8H283 antibody to myeloma progenitor cells, myeloma plasma cells, and CD45-positive leukocyte cells originated from multiple myeloma patients.

3. Identification of Antibody R8H283 That Specifically Binds to Myeloma Cell in Bone Marrow of Human Multiple-Myeloma Patient Bone marrow cells originated from a myeloma patient were stained with about 200 clones of candidate antibodies obtained in section 2 above, and analyzed by FACS. Each antibody was added to bone marrow cells originated from a multiple-myeloma patient, and incubated at 4° C. for 30 minutes, followed by washing. PE-conjugated anti-mouse IgG-PE as a secondary antibody was added thereto and further incubated at 4° C. for 30 minutes. After washing, the result was finally stained with an APC-conjugated anti-CD138 antibody (Biolegend), a FITC-conjugated anti-CD38 antibody (Biolegend), or a Cy7-PE-conjugated anti-CD45 antibody (Biolegend). Instead of candidate antibodies, a sample containing mouse IgG was also prepared as an isotype control. These were analyzed by flow cytometry, and antibodies that bind to CD45−CD38++CD138+ myeloma plasma cells and CD45−CD38++CD138− myeloma progenitor cells, but not to CD45+ blood cells were selected. As a result, the R8H283 antibody was identified as an antibody that satisfies these conditions (FIGS. 1 and 2). In each histogram, the Y axis indicates the number of cells and the X axis indicates the bond strength of the R8H283 antibody. Examination was further performed on many cases, and the binding of the R8H283 antibody to CD45−CD38++CD138+ myeloma plasma cells and CD45−CD38++CD138-myeloma progenitor cells was confirmed in many cases. However, it became clear that the R8H283 antibody binds almost not at all to CD45+ blood cells.

4. Identification of Antigenic Protein to Which R8H283 Antibody Binds

Figure 3:
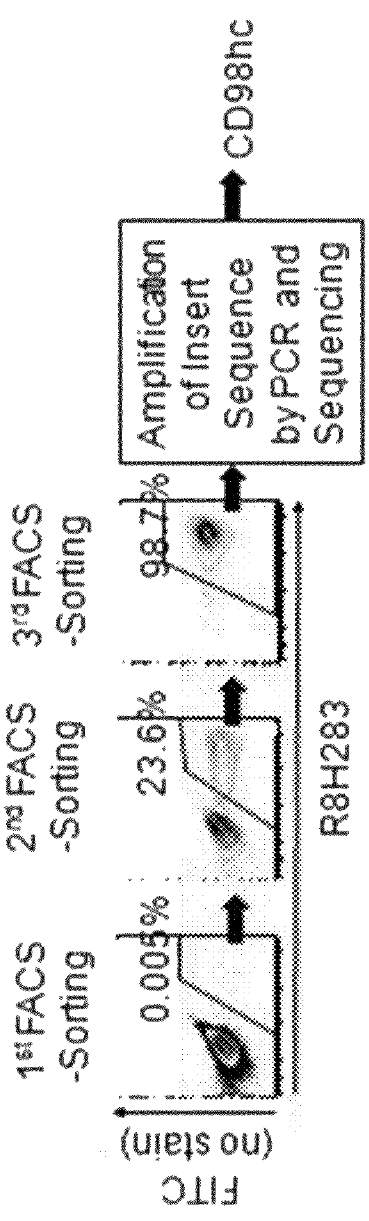
FIG. 3 shows a process by which R8H283 antibody-bound BaF3 cells (initially less than 0.1%) were concentrated by FACS-sorting, and CD98hc, which was the bound antigen, was identified.

Identification of an antigenic protein to which the R8H283 antibody binds was performed by an expression cloning method. First, a DNA library was prepared from RPMI8226 cells that are known to be bound by the R8H283 antibody using a superscript choice system for cDNA synthesis (Invitrogen), and was introduced into a pMXs retroviral vector (provided by Professor Toshio Kitamura at the Institute of Medical Sciences, University of Tokyo) using an BstXI adaptor (Invitrogen). BaF3 cells were infected with a retrovirus obtained by introducing the thus-prepared CDNA library into plat-E cells (provided by Professor Toshio Kitamura), thereby obtaining BaF3 cells that express a cDNA library originated from RPMI8226. Subsequently, these cells were stained with the R8H283 antibody, and an operation of concentrating positive cells with FACS-sorting was repeated (FIG. 3). After the third sorting, most cells were those that bind to R8H283. Thus, the insert of the retrovirus possessed by the cells was amplified by PCR and then identified by sequencing. The results revealed that CD98hc is the antigenic protein.

5. Confirmation that Antigen to which R8H283 Antibody Binds is CD98hc Protein

Figure 4:
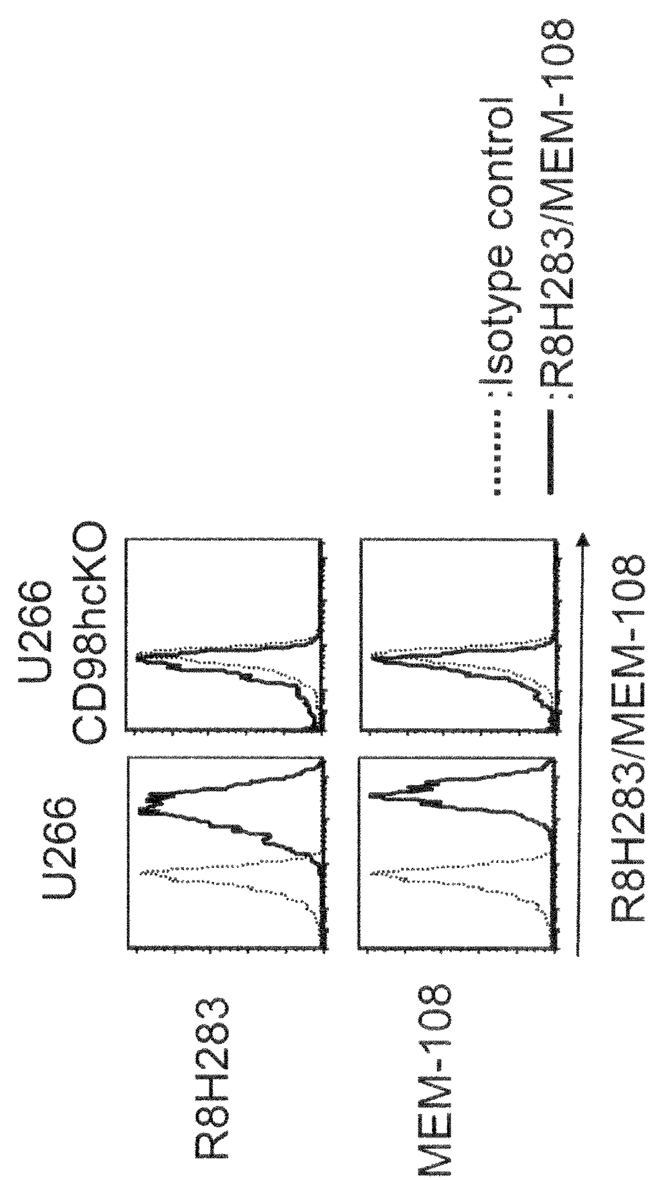
FIG. 4 shows the results confirmed by FACS that the R8H283 antibody binds to U266 cells but not to CD98hc-defective U266 cells. MEM-108 is an anti-human CD98 antibody.

A CD98hc-defective U266 myeloma cell line was prepared using a Crispa-Cas9 system in accordance with the following procedure, and the antigenic protein to which the R8H283 antibody binds was confirmed to be CD98hc. First, a vector was prepared by inserting a double-stranded DNA sequence (a CD98hc-specific target sequence) into a PX330 vector (adgene). The obtained vector together with a linear hygromycin-resistance gene expression vector (Clontech), which is a vector for selecting a medicinal agent, was introduced into U266 cells using NucleofectorII (Lonza). Thereafter, CD98hc expression in clones growing in a medium containing hygromycin were stained with a MEM-108 antibody (anti-CD98 antibody, Biolegend) and analyzed by FACS, thereby identifying CD98hc-defective cells (U266CD98hcKO). Second, the CD98hc-defective cell were stained with the R8H283 antibody and analyzed with FACS. As a result, while the R8H283 antibody bound to the wild-type U266 cell, the binding of the R8H283 antibody to the CD98hc-defective line was completely lost (FIG. 4). This indicates that R8H283 binds only to CD98hc protein, and thus, the CD98hc protein was confirmed to be the antigen of the R8H283 antibody.

Figure 5:
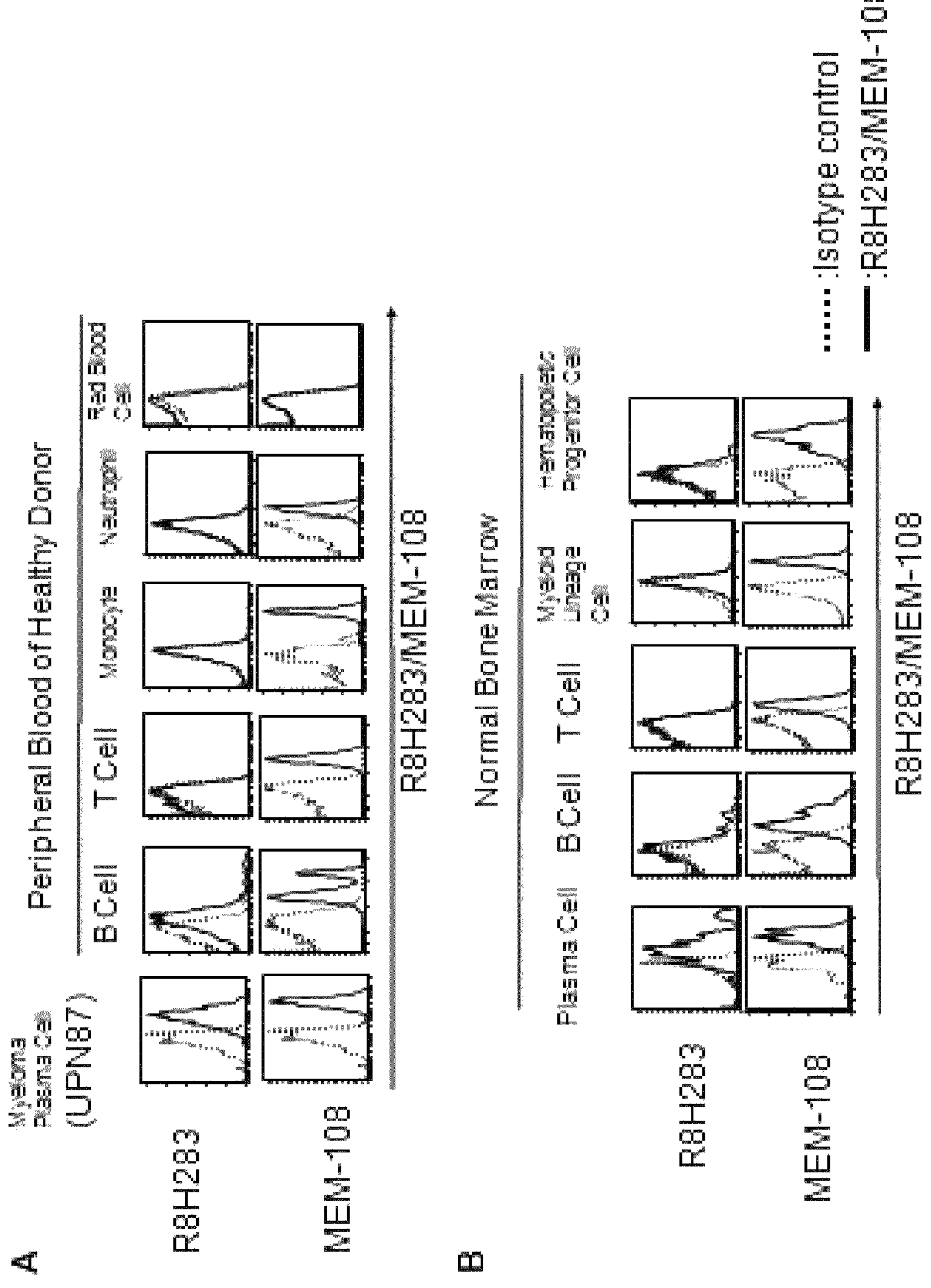
FIG. 5 shows the results of FACS analysis of the binding of the R8H283 antibody and MEM-108 antibody to cell fractions of peripheral blood cells (A) and bone marrow cells (B) from a healthy individual.

6. Measurement of Binding Pattern of R8H283 Antibody in Cell Fractions of Peripheral Blood and Bone Marrow of Healthy Individuals Using a commercially available anti-CD98 antibody (MEM-108, Biolegend) and the R8H283 antibody, the binding of these antibodies to various cell fractions in peripheral blood and bone marrow cells in healthy individuals was measured. After red blood cells were removed using HES40 from peripheral blood cells originated from a healthy individual, an Fc receptor blocking reagent (Miltenyi) was added thereto to block antibodies that exhibited non-specific binding. Thereafter, the R8H283 antibody, MEM-108 antibody, or mouse IgG2 isotype control was added thereto and incubated at 4° C. for 30 minutes. After washing, PE-conjugated anti-mouse IgG-PE as a secondary antibody was added thereto, and further incubated at 4° C. for 30 minutes. After washing, the result was finally stained with a Cy7-APC-conjugated anti-CD19 antibody (Biolegend), FITC-conjugated anti-CD14 antibody (Biolegend), or Cy7-PE-conjugated anti-CD3 antibody (Biolegend). These were analyzed by flow cytometry to measure the binding of the R8H283 antibody or MEM-108 antibody in each fraction (FIG. 5A). Additionally, 1 μl of peripheral blood was added to 100 μl of EDTA-PBS and also stained with the R8H283 antibody or MEM-108 antibody in the same manner. Finally, the result was stained with a Pacific-blue-conjugated anti-CD235 antibody (BD Pharmingen) to examine the presence or absence of each antibody in CD235-positive red blood cells (FIG. 5A).

Bone marrow cells originated from a healthy individual were also stained with the R8H283 antibody or MEM-108 antibody as with peripheral blood cells, and finally stained with an APC-conjugated anti-CD34 antibody (BD Pharmingen), Cy7-APC-conjugated anti-CD19 antibody (BD Pharmingen), Cy7-PE-conjugated anti-CD38 antibody (eBioscience), ALEXA FLUOR 647 (fluorescent dye)—conjugated anti-CD3 antibody (BD Pharmingen), or FITC-conjugated anti-CD14 antibody (eBioscience). These were analyzed by flow cytometry, and the binding of the R8H283 antibody or MEM-108 antibody in each fraction was measured (FIG. 5B). The results indicate that while the MEM-108 antibody binds to all blood cells except for red blood cells, R8H283 does not bind to normal blood cells except for a small portion of plasma cells and B cells.

Figure 6:
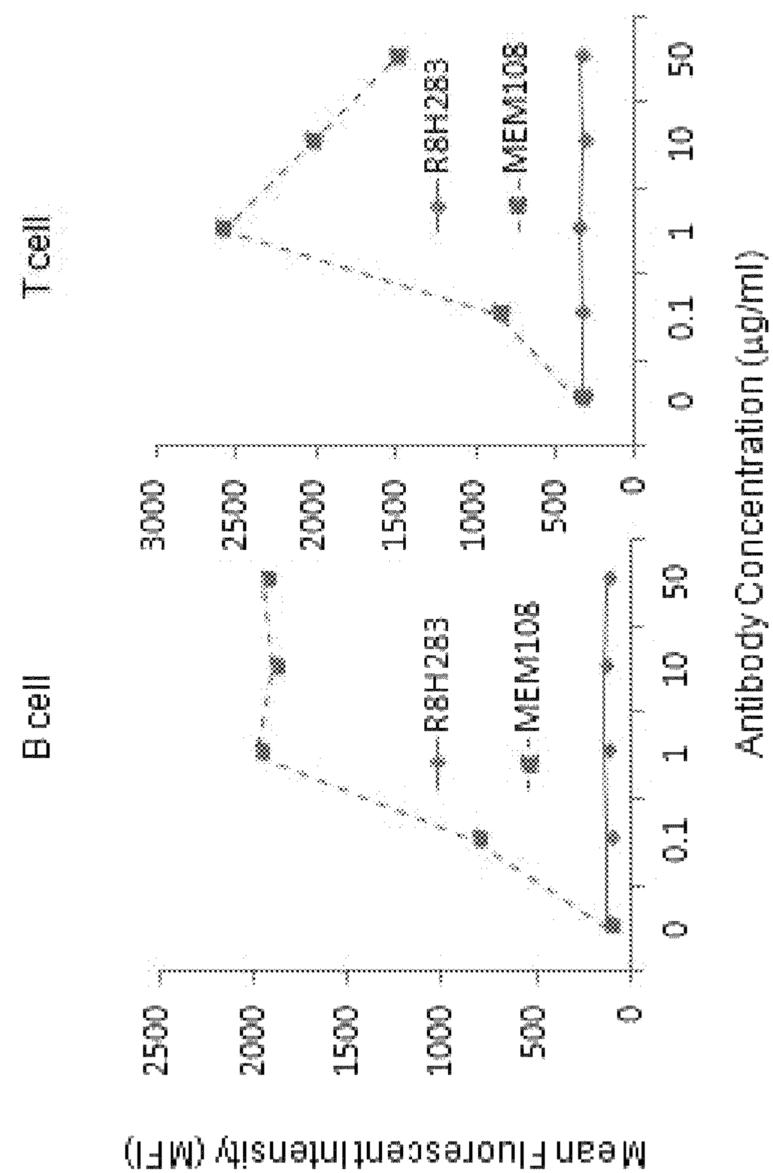
FIG. 6 shows the results of a study in which the R8H283 antibody and MEM-108 antibody of different concentrations were bound to B lymphocytes and T lymphocyte cells from peripheral blood of a healthy individual and stained with an anti-mouse IgG-PE antibody, followed by FACS analysis. The horizontal axis indicates the antibody concentration, and the vertical axis indicates the fluorescent intensity. Unlike MEM108, R8H283 did not at all bind to lymphocytes, even when the concentration of the antibody was increased.

Additionally, B cells and T cells of peripheral blood from a healthy individual were stained with the R8H283 or MEM-108 antibody of different concentrations, and the binding of each antibody was measured by FACS. While the MEM-108 antibody exhibited a concentration-dependent increase in fluorescent intensity, which indicates the bond amount of antibody, the R8H283 antibody did not exhibit its binding to lymphocytes from a healthy individual even when the antibody concentration was increased to 50 μg/ml (FIG. 6). This indicates that the CD98hc protein is present in lymphocytes, but that the R8H283 antibody does not bind to normal lymphocytes.

Figure 7:
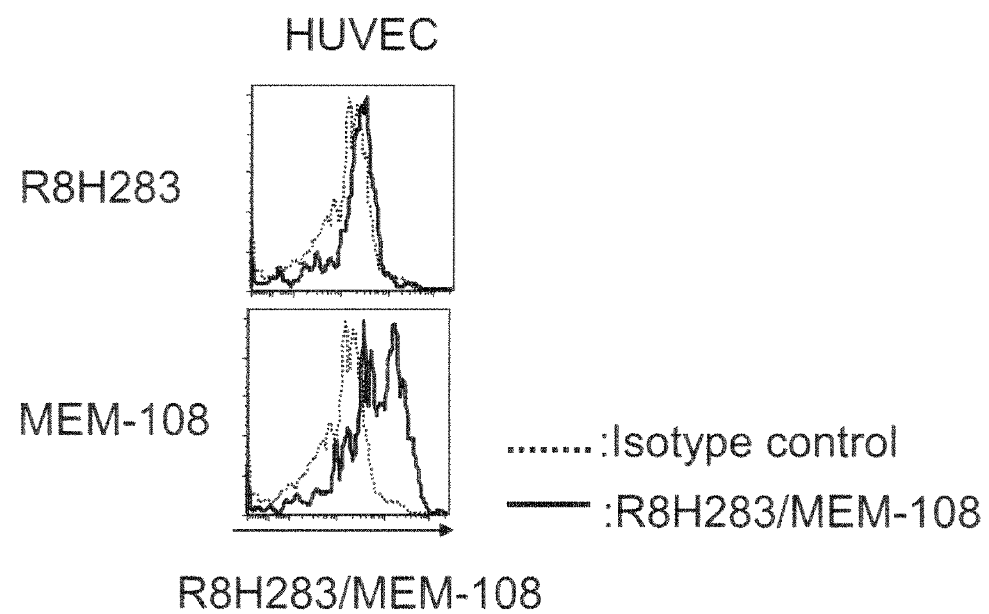
FIG. 7 shows the results of FACS analysis of the binding of the R8H283 antibody and MEM-108 antibody to normal vascular endothelial cells (HUVEC cells).

CD98 protein is known to be expressed in organs other than the blood system. Analysis was performed on the binding of the R8H283 antibody or MEM-108 antibody to a HUVEC cell, which is a normal vascular endothelial cell and is a cell analyzable by FACS among normal cells other than the blood system. The results indicate that while MEM-108 binds to HUVEC, R8H283 binds almost not at all to HUVEC (FIG. 7).

Figure 8:
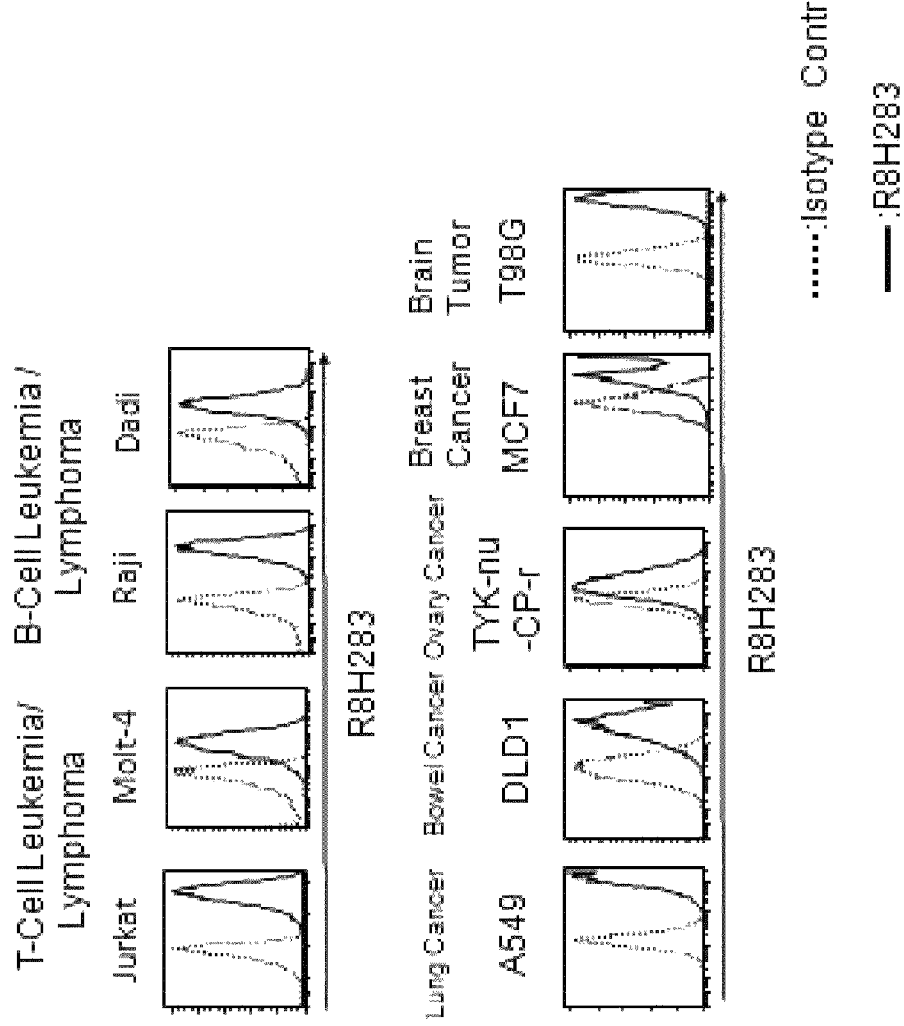
FIG. 8 shows the results of FACS analysis of the binding of the R8H283 antibody to various cancer cell lines.

In the same manner as above, the binding of the R8H283 antibody to cancer cell lines other than myeloma was analyzed. The results revealed that as shown in FIG. 8, the R8H283 antibody binds to any of the following: Jurkat cell and Molt4 cell, which are a T-cell leukemia/lymphoma cell line; Raji cell and Daudi cell, which are a B-cell leukemia/lymphoma cell line; A549 cell, which is a lung cancer cell line; DLD-1cell, which is a bowel cancer cell line; TYK-nu-CPr cell, which is an ovary cancer cell line; MCF-7 cell, which is a breast cancer cell line; and T98G cell, which is a brain tumor cell line. These results suggest that the R8H283 antibody does not bind to normal cells, but specifically binds to an extensive range of cancer cells. In the cancer cells, a specific structure alteration occurs on CD98hc, and the R8H283 antibody appears to specifically recognize the altered structure.

Figure 9:
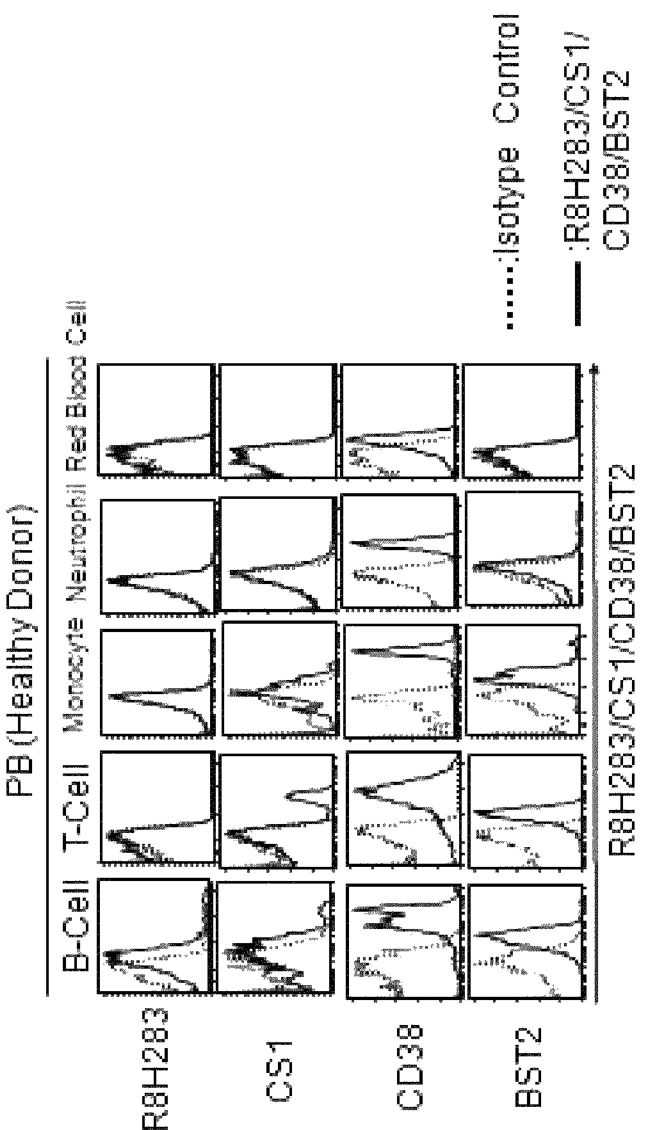
FIG. 9 shows the results of FACS analysis of the binding of the R8H283 antibody, anti-CS1 antibody, CD38 antibody, and anti-BST2 antibody to various cell fractions of peripheral blood cells from a healthy individual.

7. Comparison of Binding Capability of R8H283 Antibody to Peripheral Blood Cell of Healthy Individual with Binding Capability of Other Antibody The binding of the R8H283 antibody to peripheral blood of a healthy individual was compared with the binding of other antibodies that are reported as useful in treating multiple myeloma to these cells. Except that an anti-CS1 antibody (Biolegend), anti-CD38 antibody (Biolegend), and anti-BST2 antibody (Biolegend) were used as a primary antibody, staining was performed in the same manner as above, followed by FACS analysis (FIG. 9). The results confirmed that while the R8H283 antibody does not bind to normal T cells at all, the anti-CS1 antibody binds to some normal T cells. The anti-CD38 antibody was confirmed to significantly bind to all normal peripheral blood cells compared with the R8H283 antibody. The anti-BST2 antibody was confirmed to significantly bind to normal T cells and monocytes compared with the R8H283 antibody. These results indicate that R8H283 has higher specificity to cancer cells, including myeloma cells.

8. Analysis of Association of R8H283 Biding with CD98hc Protein Glycosylation

Figure 10:
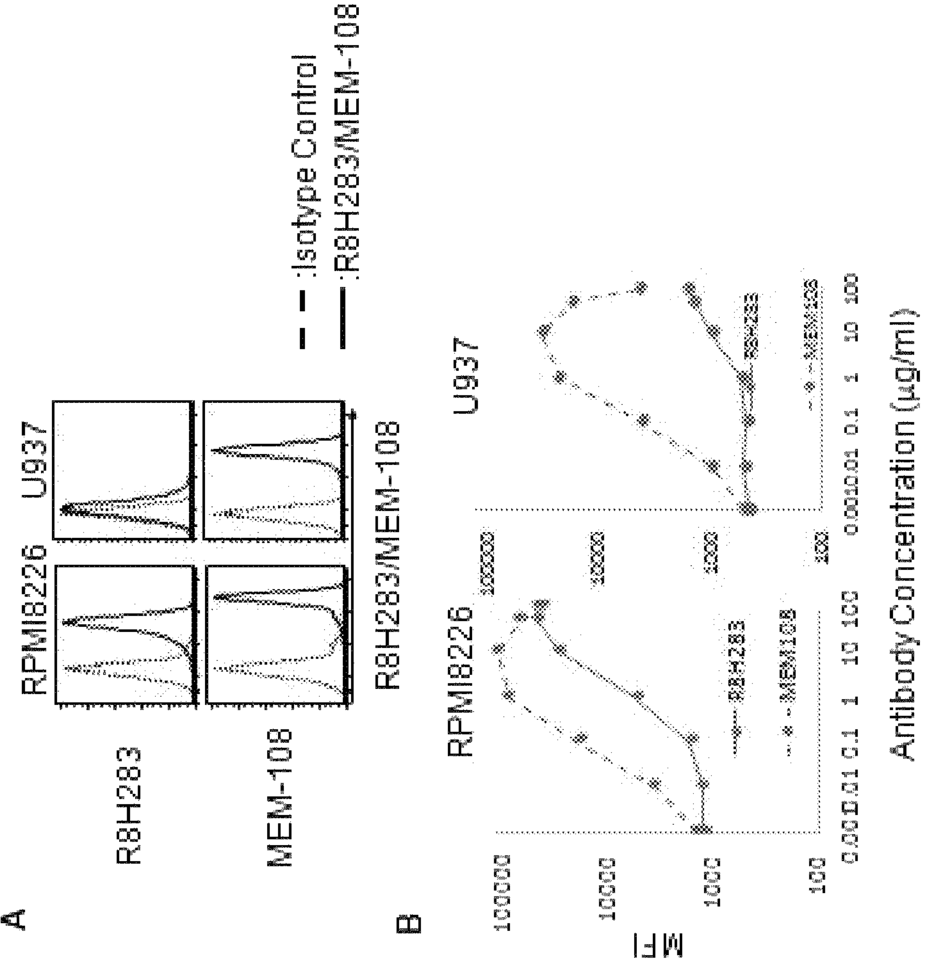
FIG. 10 shows (A) the results of FACS analysis of the binding of the R8H283 antibody and MEM-108 antibody to myeloma cell line RPMI8226 and myeloid leukemia cell line U937, and (B) the results of a study in which the R8H283 antibody and MEM-108 antibody of different concentrations were bound to myeloma cell line RPMI8226 and myeloid leukemia cell line U937 and stained with an anti-mouse IgG-PE antibody, followed by FACS analysis. The horizontal axis indicates the antibody concentration, and the vertical axis indicates the fluorescent intensity. Unlike MEM108, R8H283 bound almost not at all to U937, even when the concentration of the antibody was increased.

The binding of the R8H283 antibody or MEM-108 antibody to myeloma cell line RPMI8226 or myeloid leukemia cell line U937 was analyzed by FACS. The staining method was the same as in the test with peripheral blood in section 6 above. The results confirmed that despite the fact that the CD98hc protein is an antigen for both of them, while the MEM-108 antibody binds to almost all cell lines, the R8H283 antibody binds to some cell lines, but not to other cell lines. For example, both antibodies bind well to RPMI8226 (myeloma cell line); however, while the MEM-108 antibody binds well to U937 (myeloid leukemia cell line), the R8H283 antibody binds almost not at all to U937 (FIG. 10A). RPMI8226 cells and U937 cells were stained with the R8H283 or MEM-108 antibody of different concentrations, and the binding of each antibody was measured by FACS. The results show that while RPMI8226 exhibited a concentration-dependent increase in fluorescent intensity for both the MEM-108 antibody and R8H283 antibody, U937 cells exhibited almost no binding of R8H283 even when the antibody concentration of the R8H283 antibody was increased to 50 μg/ml (FIG. 10B).

Figure 11:
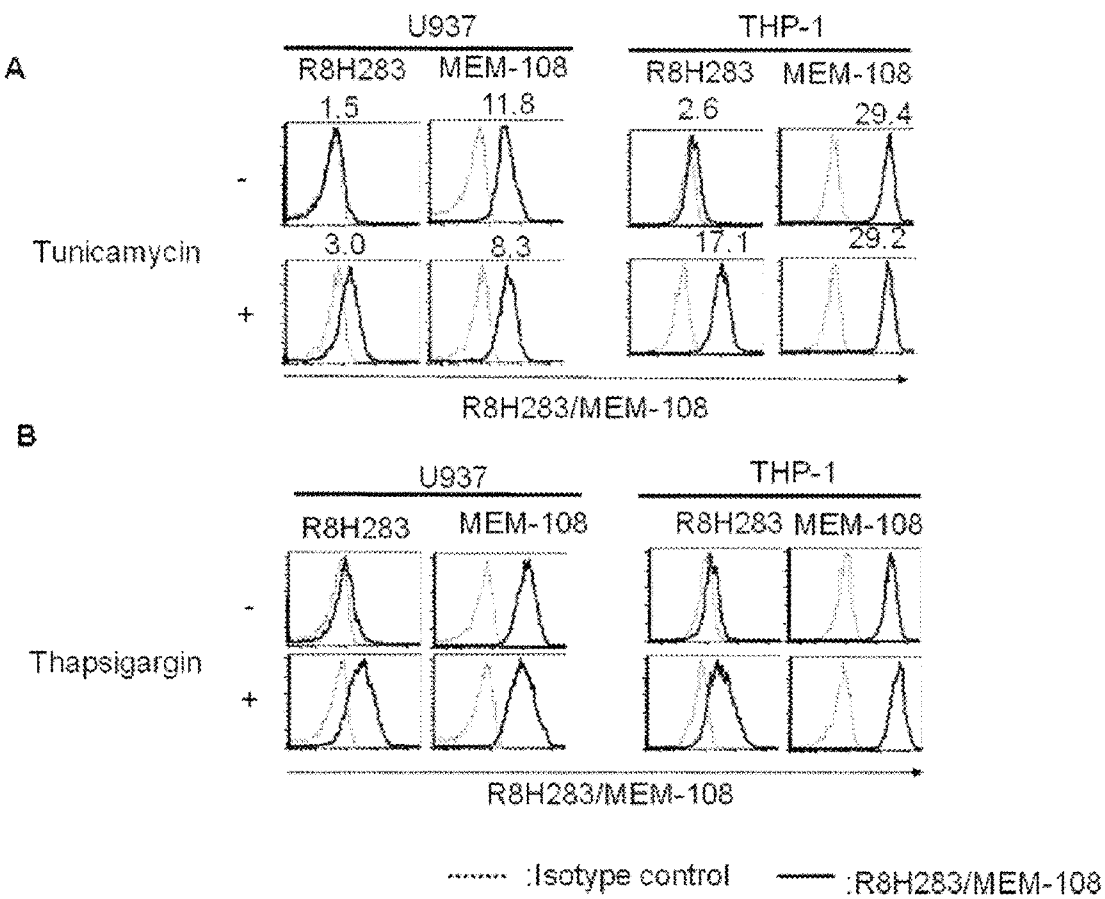
FIG. 11 shows (A) the results of FACS analysis of the binding of R8H283 and MEM-108 to U937 cells treated with tunicamycin (2.5 μg/ml) for 48 hours and non-treated U937 cells. The values indicate a mean fluorescent intensity of R8H283 binding (a corrected value obtained by dividing the mean fluorescent intensity (MFI) by MFI of the isotype control).

This is probably because of the difference in post-translational modification to CD98hc, which is expressed in myeloma cell lines and leukemia cell lines. CD98hc is a protein that is subject to N-linked glycosylation to a significantly high degree, and the degree of glycosylation may vary. Thus, tunicamycin (2.5 mg/ml), which is an N-glycan synthesis inhibitor, was added to a culture solution of U937 cells or THP1 cells, which are not bound by the R8H283 antibody, for 24 hours and the binding of the R8H283 antibody or MEM-108 antibody was analyzed by FACS. Staining of each antibody was performed by the following method. $1\times10^5$ cells were suspended in 50 μl of PBS+2% cow fetal serum, and 1 μl of an FC blocking reagent (Miltenyi Biotec, #130-059-901) was added thereto. Subsequently, R8H283 or MEM-108 was added to give a final concentration of 50 μg/ml and 2.5 μg/ml, and the mixture was allowed stand on ice for 30 minutes. Separately, respective isotype control antibodies were added to give the same concentrations to other cell suspensions prepared in the same manner. The cells were washed with PBS+2% cow fetal serum twice and suspended again in 50 μl of a phycoerythin (PE)-conjugated goat anti-mouse IgG antibody diluted to 1 μg/ml in PBS+2% cow fetal serum. The cells were further allowed to stand for 30 minutes. Thereafter, the cells were washed with PBS+2% cow fetal serum twice and suspended again in PBS+2% cow fetal serum containing 1 μg/ml propidium iodide (PI), followed by analysis by FACS Canto II (Beckton Dickinson). At this stage, PI-positive dead cells were excluded from the analysis, and the amount of antibodies that bind to viable cells was quantified as a mean value of fluorescent intensity of PE (mean fluorescent intensity (MFI)). The value of MFI that indicates the amount of the binding of the R8H283 antibody (a corrected value obtained by dividing with the value of isotype control (mouse IgG2a isotype control, Biolegend, #401502)) was as follows: before tunicamycin treatment, U937 cell 1.5, and THP-1 cell 2.6; and after tunicamycin treatment, U937 cell 3.0, and THP-1 cell 17.1; this indicates that the binding of the R8H283 antibody after tunicamycin treatment increased (U937: 2.0 times, THP-1:6.6 times in MFI). However, the value of MFI that indicates the amount of the binding of the MEM-108 antibody (a corrected value obtained by dividing with an isotype control (mouse IgG1 isotype control, Biolegend, #400102)) was as follows: before treatment, U937 cell 11.8 and THP-1 cell 29.4; and after treatment, U937 cell 8.3 and THP-1 cell 29.1; this indicates no increase in the amount of the binding of R8H283 (FIG. 11A). This clearly indicates that the difference in N-linked glycosylation determines the amount of the binding of the R8H283 antibody.

Figure 12:
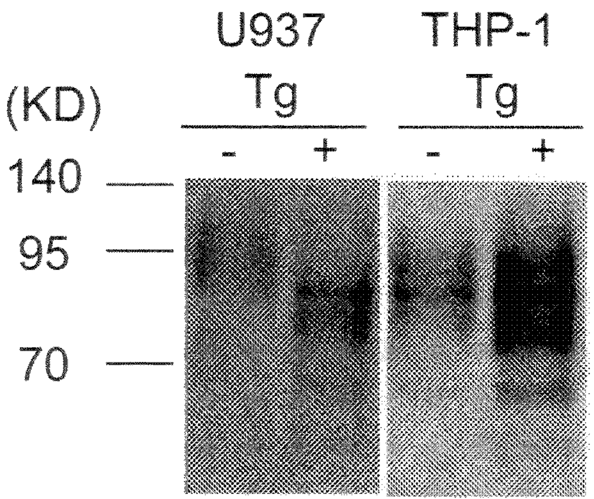
FIG. 12 shows the results of a study in which cell lysates of U937 cells or THP1 cells both treated with thapsigargin (1 mM) for 48 hours and a cell lysate of non-treated cells were each subjected to electrophoresis on SDS-PAGE gel, and then subjected to western blotting using a polyclonal anti-CD98 antibody (H300: Santa Cruz Biotechnology, Inc.). The molecular weight of CD98 was decreased by inhibition of endoplasmic reticulum function due to the thapsigargin treatment, indicating its possible expression with incomplete glycosylation.

Because tunicamycin is an N-glycan synthesis inhibitor and also causes high endoplasmic reticulum stress, tunicamycin is used as a medicinal agent to evoke endoplasmic reticulum stress. Because a significantly great amount of protein synthesis is always happening in myeloma cells, endoplasmic reticulum stress is always being placed on myeloma cells. The inventors speculated that glycosylation of CD98hc may change under endoplasmic reticulum stress, thereby enabling the R8H283 antibody to bind to CD98hc. Thus, U937 cells or THP1 cells were treated with thapsigargin (1 nM, an endoplasmic reticulum stress inducer), which does not directly inhibit glycosylation, unlike tunicamycin, and the binding of the R8H283 antibody or MEM-108 antibody was analyzed by FACS. The results indicated that the binding of the R8H283 antibody appeared due to thapsigargin treatment (FIG. 11B). Additionally, the molecular weight of CD98hc in the cells treated with thapsigargin and non-treated cells was examined by western blotting, and it became clear that CD98hc of a lower molecular weight or CD98hc with incomplete glycosylation was expressed under endoplasmic reticulum stress caused by thapsigargin (FIG. 12).

Figure 13:
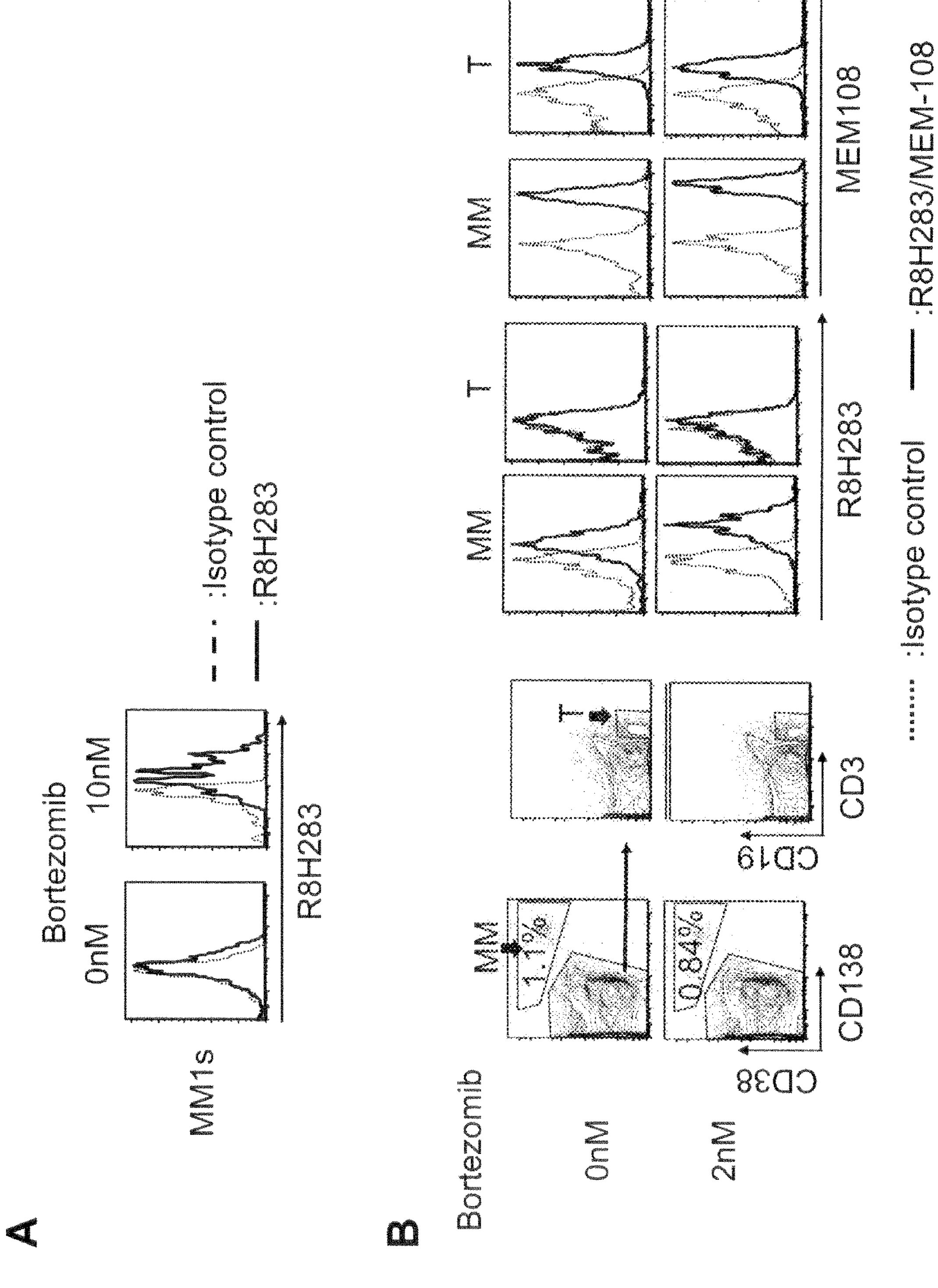
FIG. 13 shows (A) the results of FACS analysis of the binding of the R8H283 antibody to MM1s myeloma cells treated with bortezomib (10 nM) for 16 hours and non-treated MM1s cells, and (B) the results of FACS analysis of the binding of the R8H283 antibody and MEM-108 antibody to bone marrow cells treated with bortezomib (2 nM) for 48 hours and non-treated cells originated from a myeloma patient.

Bortezomib, which is a proteasome inhibitor, also causes high endoplasmic reticulum stress on myeloma cells. Next, MM1s, which is a myeloma cell line to which R8H283 binds in a relatively weak manner, was treated with bortezomib (10 nM), and compared with non-treated cells in terms of R8H283 binding. As a result, bortezomib treatment clearly increased the binding of R8H283 (FIG. 13A). The same experiment was performed on bone marrow cells originated from a myeloma patient. Despite the fact that the amount of the binding of MEM-108 in myeloma cells did not change, the amount of the binding of R8H283 increased; however, such a change did not occur in T lymphocytes in which an increase in endoplasmic reticulum stress by bortezomib does not occur (FIG. 13B). These results suggest that alteration of glycosylation caused by high endoplasmic reticulum stress that typically occurs in myeloma cells may be associated with the emergence of the epitope to which the R8H283 antibody binds.

9. Identification of Epitope

To identify the epitope that R8H283 recognizes, various human/mouse chimera CD98hc protein expression vectors were prepared using overlapping PCR as described below. The sequences of the primers used are as follows.

```
EcoRIhCD98F,
                                        (SEQ ID NO: 25)
CCGGAATTCCCACCATGAGCCAGGACACCGAGGTGGATATGA

BamHIhCD98R,
                                        (SEQ ID NO: 26)
AAAGGATCCTCATCAGGCCGCGTAGGGGAAGCGGAGCAGCAGCC

EcoRImCD98F,
                                        (SEQ ID NO: 27)
CCGGAATTCCCACCATGAGCCAGGACACCGAAGTGGACATGAAA

BamHImCD98R,
                                        (SEQ ID NO: 28)
CGCGGATCCTCATCAGGCCACAAAGGGGAACTGTA

cCD98-203F,
                                        (SEQ ID NO: 29)
TCATTCTGGACCTTACTCCCAACTACC

cCD98-203R,
                                        (SEQ ID NO: 30)
GGTAGTTGGGAGTAAGGTCCAGAATGA

cCCD98-365F,
                                        (SEQ ID NO: 31)
TTCCGGCGGCTGAGTGAC

cCD98-365R,
                                        (SEQ ID NO: 32)
GTCACTCAGCCGCCGGAA

cCD98-427F,
                                        (SEQ ID NO: 33)
AGCTACGGGGATGAGATTGGCCT

cCD98-427R,
                                        (SEQ ID NO: 34)
AGGCCAATCTCATCCCCGTAGCT

cCD98-370F,
                                        (SEQ ID NO: 35)
TTGGCCTGGATGCAGCTGCCCTTCCTGGACAGC

cCD98-370R,
                                        (SEQ ID NO: 36)
GCTGTCCAGGAAGGGCAGCTGCATCCAGGCCAA

cCD98-376F,
                                        (SEQ ID NO: 37)
TGCCCTTCCTGGACAGCC

cCD98-376R,
                                        (SEQ ID NO: 38)
GGCTGTCCAGGAAGGGCA

cCD98-402F,
                                        (SEQ ID NO: 39)
CCAGCTTCCCTGACATCCCAGGGGCTGTAA

cCD98-402R,
                                        (SEQ ID NO: 40)
TTACAGCCCCTGGGATGTCAGGGAAGCTGG

cCD98-409F,
                                        (SEQ ID NO: 41)
CTGTAAGTGCCAACATGACTGTGAAG

cCD98-409R,
                                        (SEQ ID NO: 42)
CTTCACAGTCATGTTGGCACTTACAG
```

PCR was performed using as a template an MSCV-ires-GFP vector to which human or mouse CD98hc CDNA was inserted. PCR was performed using a prime star (Takara Bio Inc.), KODfx (Toyobo Co., Ltd.), and Accuprime taq (Invitrogen). Chimeric CDNA (FIG. 14) was prepared as described below. First, 25-cycle PCR was performed with F primer 1 and R primer 1 using cDNA1 as a template, and also 25-cycle PCR was separately performed with F primer 2 and R primer 2 using cDNA2 as a template, with any of the PCR enzymes listed above. The PCR products were subjected to electrophoresis on 1% agarose gel, and then purified with a QIAquick gel extraction kit. 5 μl of water was added to 2.5 μl of each PCR product, and PCR at 94° C. for 15 seconds, 55° C. for 30 seconds, and 68° C. for 2 minutes was performed in three cycles, followed by incubation at 99° C. for 5 minutes. Overlapping PCR was then performed with F primer 1 and R primer 2 using 1 μl of each result as a template. After the PCR products were confirmed by electrophoresis on agarose gel, the products were cloned using a TA cloning kit (Invitrogen). The sequences were confirmed by sequencing. Thereafter, inserts were cut out with EcoRI and BamHI, and inserted into MSCV-ires-GFP vectors for use as expression vectors. Table 3 shows the combinations of primers and templates and the names of the obtained expression vectors.

TABLE 3

| cDNA1 (MIG-) | Fprimer1 (-CD98F) | Rprimer1 (CD98-) | cDNA2 | Fprimer2 (CD98-) | Rprimer2 (-CD98R) | Expression Vector |
|---|---|---|---|---|---|---|
| hCD98 | EcoRIh | 203R | mCD98 | 203F | BamHIm | h203m |
| mCD98 | EcoRIm | 203R | hCD98 | 203F | BamHIh | m203h |
| hCD98 | EcoRIh | 365R | mCD98 | 365F | BamHIm | H365m |
| mCD98 | EcoRIm | 365R | hCD98 | 365F | BamHIh | m365h |
| hCD98 | EcoRIh | 427R | mCD98 | 427F | BamHIm | h427m |
| mCD98 | EcoRIm | 427R | hCD98 | 427F | BamHIh | m427h |
| m365h | EcoRIm | 427R | mCD98 | 427F | BamHIm | m365h427m |
| m365h | EcoRIm | 409R | mCD98 | 409F | BamHIm | m365h409m |
| m365h | EcoRIm | 402R | mCD98 | 402F | BamHIm | m368h402m |
| mCD98 | EcoRIm | 370R | m365h409m | 370F | BamHIm | m370h409m |
| mCD98 | EcoRIm | 376R | m365h409m | 376F | BamHIm | m376h409m |

The expression vectors were individually introduced into a CHO cell using lipofectamine 2000 (Invitrogen) and stained with the R8H283 antibody and MEM-108 antibody for 24 hours, thereby analyzing the binding of each antibody by FACS in GFP positive cells (having a vector introduced). The staining method is the same as in section 3 above.

Figure 14:
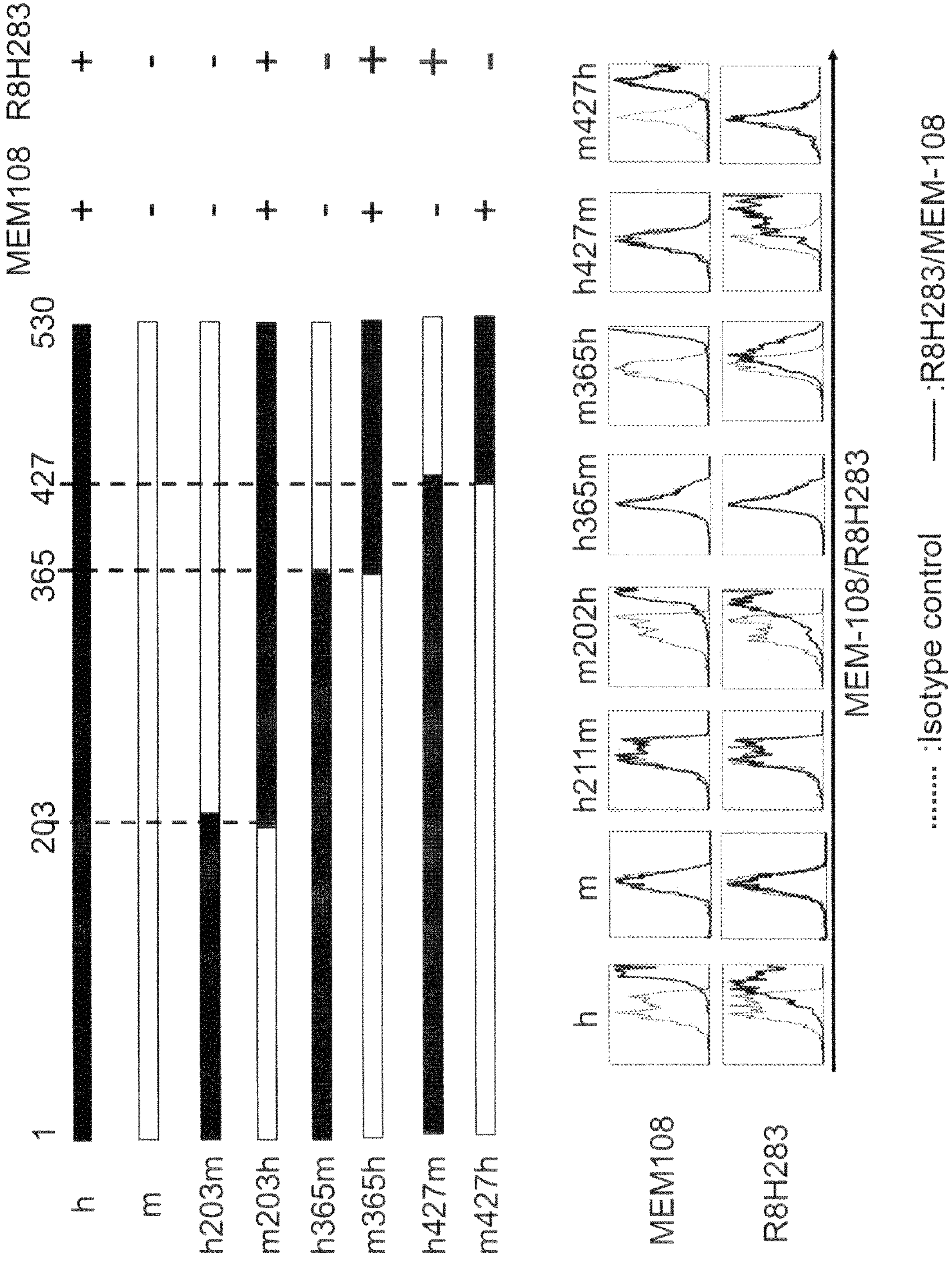
FIG. 14 shows the construction of human/mouse chimera CD98hc proteins and the presence or absence of the binding of the R8H283 antibody or MEM-108 antibody to CHO cells transiently expressing the proteins (the upper figure), and the results of FACS analysis of the binding of the R8H283 antibody and MEM-108 antibody to CHO cells transiently expressing human/mouse chimera CD98hc proteins (the lower figure).
Figure 15:
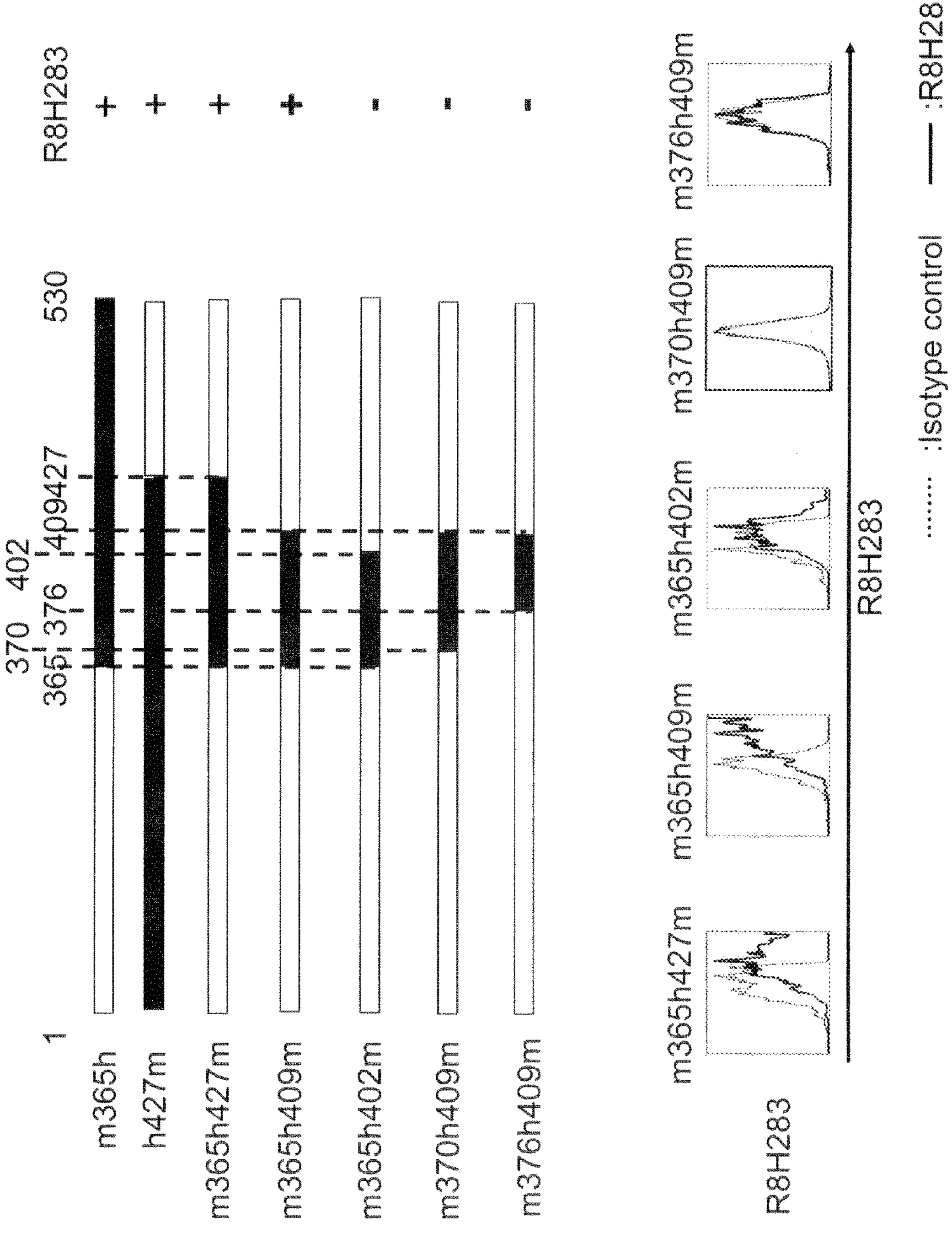
FIG. 15 shows the construction of human/mouse chimera CD98hc proteins and the presence or absence of the binding of the R8H283 antibody to CHO cells transiently expressing the proteins (the upper figure) and the results of FACS analysis of the binding of the R8H283 antibody to CHO cells transiently expressing human/mouse chimera CD98hc proteins (the lower figure).

The results revealed that first, the amino acid sequence of the epitope necessary to form an antigen that is recognized by R8H283 is present in the region at positions 203 to 427 of human CD98hc. Further refined search revealed that the epitope is present in the region between the amino acid at position 365 and the amino acid at position 427 of human CD98hc. However, the epitope recognized by the MEM-108 antibody was thought to be present in the region between position 428 and the C-terminus (FIG. 14). Still further refined search confirmed that the epitope is present in the region from position 365 to position 407 of human CD98hc (YGDEIGLDAAALPGQPMEAPVMLWDESSFPDIPGAVSANMTVK (SEQ ID NO: 23)) (FIG. 15). In this sequence, the fifth N from the C-terminus is an N-glycosylation site.

10. Determination of Base Sequence of Antibody Molecule Variable Region of R8H283 Antibody The subclass of the R8H283 monoclonal antibody was confirmed using an Isotyping Kit (Roche), and the subclass was determined to be IgG2sa. Additionally, the base sequence and the amino acid sequence of the variable region of the antibody molecule produced by hybridoma R8H283 were determined. The determination of the sequences was performed using a Smarter RACE CDNA Amplification Kit (Clontech). Specifically, CDNA fragments of H chain and κ chain variable regions were amplified by PCR reaction using cDNA prepared from mRNA originated from the hybridoma that produces the R8H283 antibody as a template, and the base sequences were decoded. Tables 4 and 5 show the amino acid sequences and base sequences of the variable regions and complementarity-determining regions (CDR1 to CDR3) of the decoded H chain and L chain (κ chain).

TABLE 4

| Region | | SEQ ID NO | Amino Acid Sequence |
|---|---|---|---|
| Heavy Chain | CDR-H1 | SEQ ID NO: 1 | GFTF |
| | CDR-H2 | SEQ ID NO: 2 | IRLKSNNYAT |
| | CDR-H3 | SEQ ID NO: 3 | SRLPSFDY |
| | Variable Region | SEQ ID NO: 4 | EVKLEESGGGLVQPGGSMKLSCVASGFTFS NYWMNWVRQSPEKGLEWVAEIRLKSNNYA THYAESYKGRFTISRDDSKSSVYLQMNNLR AEDTGIYYCSRLPSFDY |
| Light Chain | CDR-L1 | SEQ ID NO: 6 | KSLLHSNGNTY |
| | CDR-L2 | SEQ ID NO: 7 | RMS |
| | CDR-L3 | SEQ ID NO: 8 | MQHLEYPFT |
| | Variable Region | SEQ ID NO: 9 | MRCLAEPLGLLVLWIPGAIGDIVMTQAAPSV PVTPGESVSISCRSTKSLLHSNGNTYLYWFL QRPGQSPQLLIYRMSNLASGVPDRFSGSGS GTAFTLRITRVEAEDVGIYYCMQHLEYPFTF GAGTKLELK |

TABLE 5

| Region | | SEQ ID NO | Base Sequence |
|---|---|---|---|
| Heavy Chain | CDR-H1 | SEQ ID NO: 11 | GGATTCACTTTC |
| | CDR-H2 | SEQ ID NO: 12 | ATTAGATTGAAATCTAATAATTATGCAACA |
| | CDR-H3 | SEQ ID NO: 13 | TCCAGACTCCCGTCCTTTGACTAC |
| | Variable Region | SEQ ID NO: 14 | GAAGTGAAGCTTGAGGAGTCTGGAGGAGGCTTGGTGCAACCTGGAGGATCCATGAAACTCTCCTGTGTTGCCTCTGGATTCACTTTCAGTAATTACTGGATGAACTGGGTCCGCCAGTCTCCAGAGAAGGGGCTTGAGTGGGTTGCTGAAATTAGATTGAAATCTAATAATTATGCAACACATTATGCGGAGTCTGTGAAAGGGAGGTTCACCATCTCAAGAGATGATTCCAAAAGTAGTGTCTACCTGCAAATGAACAACTTAAGAGCTGAAGACACTGGCATTTATTACTGTTCCAGACTCCCGTCCTTTGACTAC |
| Light Chain | CDR-L1 | SEQ ID NO: 16 | AAGACTCTCCTGCATAGTAATGGCAACCTTAC |
| | CDR-L2 | SEQ ID NO: 17 | CGGATGTCC |
| | CDR-L3 | SEQ ID NO: 18 | ATGCAACATCTAGAATATCCTTTCACG |
| | Variable Region | SEQ ID NO: 19 | AAGGGGACTCAAGACTTTTTGTATCAAGTTCTCAGAATGAGGTGCCTAGCTGAGTTCCTGGGGCTGCTTGTGCTCTGGATCCCTGGAGCCATTGGGGATATTGTGATGACTCAGGCTGCACCCTCTGTACCTGTCACTCCTGGAGAGTCAGTATCCATCTCCTGCAGGTCTACTAAGAGTCTCCTGCATAGTAATGGCAACACTTACTTGTATTGGTTCCTGCAGAGGCCAGGCCAGTCTCCTCAGCTCCTGATATATCGGATGTCCAACCTTGCCTCAGGAGTCCCAGACAGGTTCAGTGGCAGTGGGTCAGGAACTGCTTTCACACTGAGAATCACTAGAGTGGAGGCTGAGGATGTGGGTATTTATTACTGTATGCAACATCTAGAATATCCTTTCACGTTCGGTGCTGGGACCAAGCTGGAGCTGAAACGG |

11. Measurement of Cytotoxic Activity of R8H283 Monoclonal Antibody

Whether cytotoxic activity is present in vitro was examined for an R8H283 monoclonal antibody purified from the supernatant of an R8H283 antibody-producing hybridoma culture by a protein G (GE healthcare). The test was performed by examining whether complement-dependent cytotoxicity (CDC) activity is present by a chromium release assay. A baby rabbit complement (Cedarene) was used as a complement. For myeloma cells, U266, OPM2, NCI-H929, and RPMI8226, which are known to be bound by the R8H283 antibody, were used. Each myeloma cell line was labeled with $^{51}Cr$ for 2 hours and washed three times. The labeled cells ($1\times10^4$ cells) were cultured in 160 μL of RPMI1640 medium+cow fetal serum to which an R8H283 monoclonal antibody or an isotype control and a 25% baby rabbit complement had been added in a 96-well U-bottomed plate ($1\times10^4$ cells). In the test using U266, each antibody used had a final concentration of 0.1 mg/ml or 1 mg/ml. In the tests using OPM2, NCI-H929, or RPMI8226, each antibody used had a final concentration of 10 μg/ml. After culture at 37° C. with 5% $CO_2$ for 90 minutes, $^{51}Cr$ released into the supernatant was counted. Specific cytotoxic activity was calculated as described below.

CDC Activity=($^{51}Cr$ release from the cells used in the test-voluntary $^{51}Cr$ release in the absence of an antibody)/(maximum $^{51}Cr$ release by addition of 1% TRITON X-100 (a surfactant)−voluntary $^{51}Cr$ release in the absence of an antibody)×100

Figure 16:
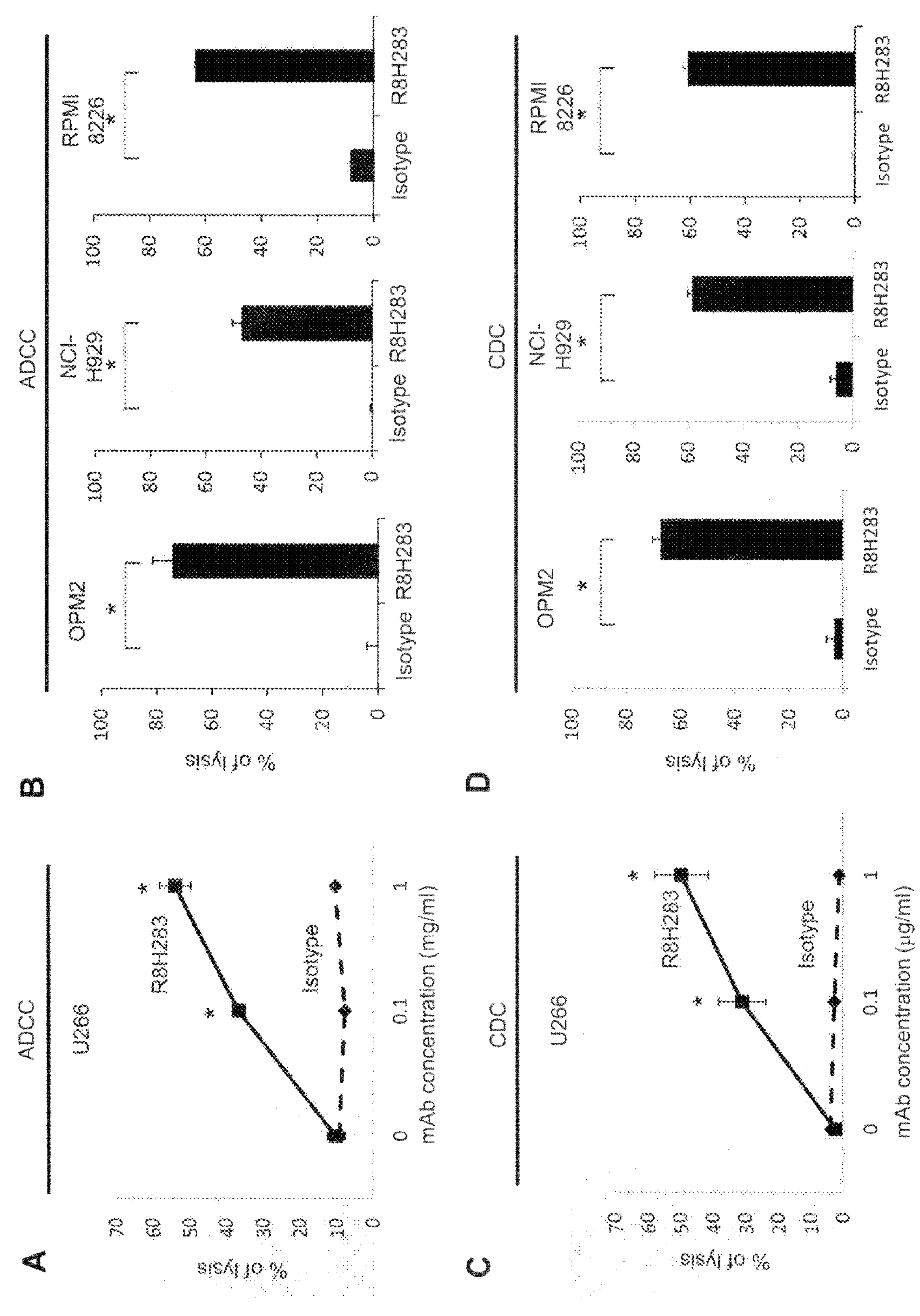
FIG. 16 shows (A) and (B) the presence or absence of antibody-dependent cellular cytotoxicity due to the R8H283 antibody, and shows (C) and (D) the presence or absence of complement-dependent cellular cytotoxicity due to the R8H283 antibody. U266, OPM2, NCI-H929, and RPMI8226 are all myeloma cell lines. In the tests the results of which are shown in (B) and (D), each antibody was added to give a final concentration of 10 μg/ml.

FIGS. 16C and 16D show the measurement results. The R8H283 monoclonal antibody was confirmed to have clear complement-dependent cellular cytotoxicity against all of the examined myeloma cell lines.

Additionally, antibody-dependent cellular cytotoxicity (ADCC) activity was also examined. Target cells were labeled with $^{51}Cr$ as with the measurement of complement-dependent cellular cytotoxicity, and bone marrow cells of a SCID mouse cultured in an RPMI1640 medium containing 10% FBS, 10 ng/ml mouse GM-CSF, and 40 IU/ml human IL2 for 6 days were used as effector cells. The R8H283 antibody or its isotype antibody (control) was added to a 96-well plate, and the target cells ($1.0\times10^4$) and effector cells ($5\times10^5$) were added thereto. In the test using U266, each antibody for use had a final concentration of 0.1 mg/ml or 1 mg/ml. In the tests using OPM2, NCI-H929, or RPMI8226, each antibody for use had a final concentration of 10 μg/ml. A reaction was performed at 37° C. for 4 hours. After separation by centrifugation, $^{51}Cr$ released into the supernatant was measured with a γ-counter. ADCC activity was determined in accordance with the following equation.

ADCC activity=($^{51}Cr$ release from cells used in the test-voluntary $^{51}Cr$ release in the absence of an antibody)/(maximum $^{51}Cr$ release caused by addition of 1% TRITON X-100 (a surfactant)−voluntary $^{51}Cr$ release in the absence of an antibody)×100

FIGS. 16A and 16B show the measurement results. The R8H283 monoclonal antibody was confirmed to have clear ADCC activity against all of the examined myeloma cell lines.

These results indicate that the R8H283 monoclonal antibody and antibodies that recognize an epitope identical to the epitope recognized by the R8H283 monoclonal antibody can be an active ingredient for treatment of multiple myeloma.

12. Inhibition Effect on Myeloma Cell Growth by Anti-human CD98hc Monoclonal Antibody Having Cytotoxic Activity in Vivo (Subcutaneous Tumor Model)

Figure 17:
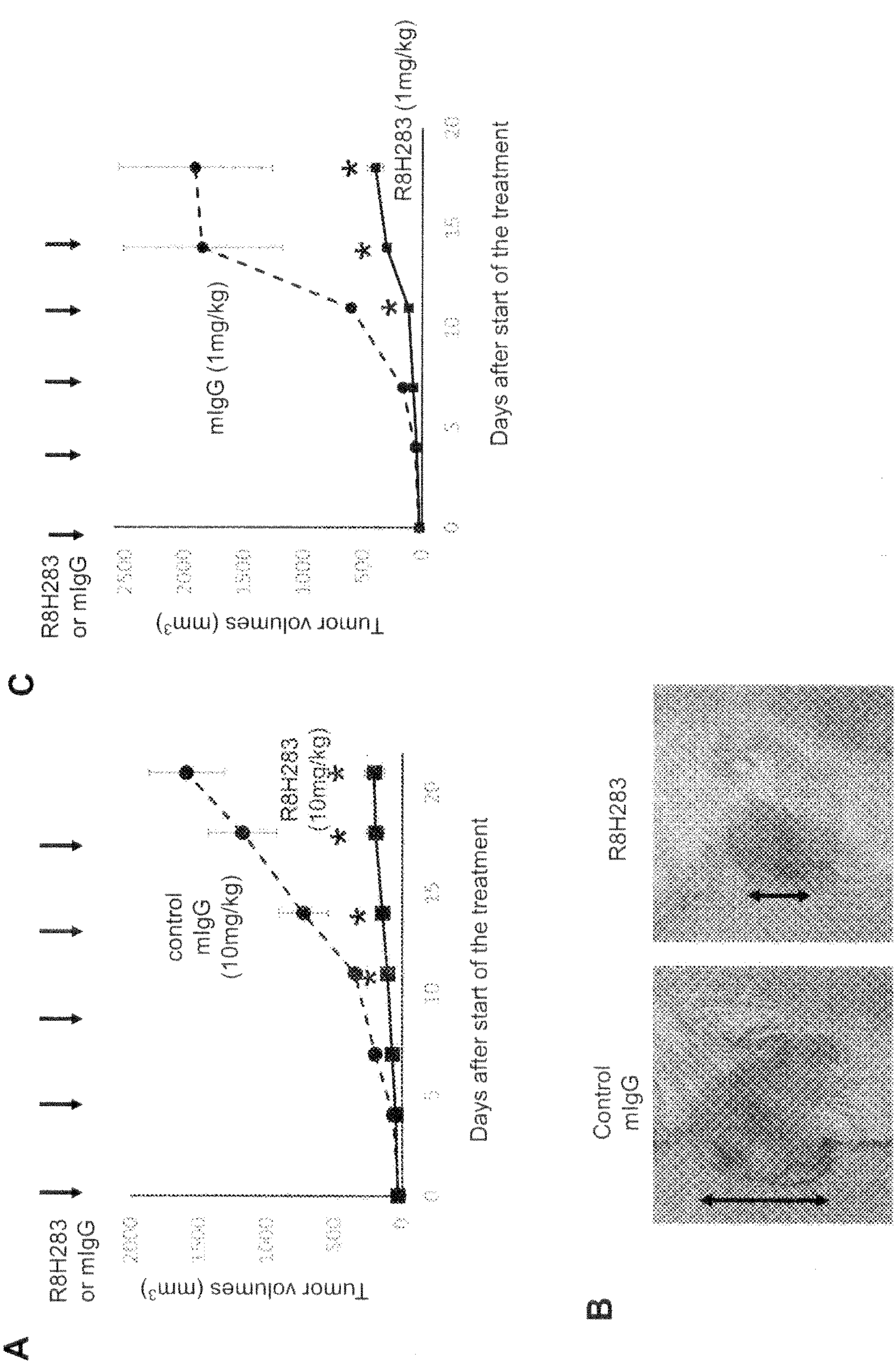
FIG. 17 shows (A) and (C) changes in volume of the tumor mass formed by myeloma cell line OPM2 that had been subcutaneously transplanted into SCID mice, and (B) the size of tumor of a control mouse and a mouse administered with the R8H283 antibody on day 21. The arrows indicate the width of the tumor.

A therapeutic effect on multiple myeloma in vivo was examined using the R8H283 monoclonal antibody that was confirmed to have cytotoxic activity in section 11 above. SCID mice were subcutaneously transplanted with a myeloma cell line OPM2 ($1\times10^7$). When the tumor volume exceeded 30 $mm^3$, the mice were divided into a group to which an anti-CD98hc antibody is administered and a control group to which IgG is administered; 10 mg/kg of the R8H283 monoclonal antibody or control IgG was administered to the groups twice a week. The tumor volume was measured twice a week, and the volume was expressed as the following approximated value: longest diameter×shortest diameter×height/2. The time point at which the volume of tumor mass formed by the transplanted myeloma cell line OPM2 exceeded 30 $mm^3$ is day 0, and FIG. 17A shows the changes in tumor volume from day 0. FIG. 17B shows the size of tumors of a control mouse (administered with IgG) and a mouse administered with the R8H283 antibody on day 21. The arrows indicate the width of the tumors. As shown in FIGS. 17A and 17B, when the control IgG was administered, myeloma cells grew in an exponential fashion; however, when the R8H283 monoclonal antibody having cytotoxic activity (R8H283) was administered, the growth of myeloma cells was almost completely inhibited. Subsequently, the dose was decreased to 1 mg/kg or 0.1 mg/kg, and completely the same test was performed. The results indicated that even administration of 1 mg/kg provides a sufficient effect (FIG. 17C).

13. Inhibition Effect on Myeloma Cell Growth by Anti-human CD98hc Monoclonal Antibody Having Cytotoxic Activity in Vivo (Parenterally Administered Model)

Figure 18:
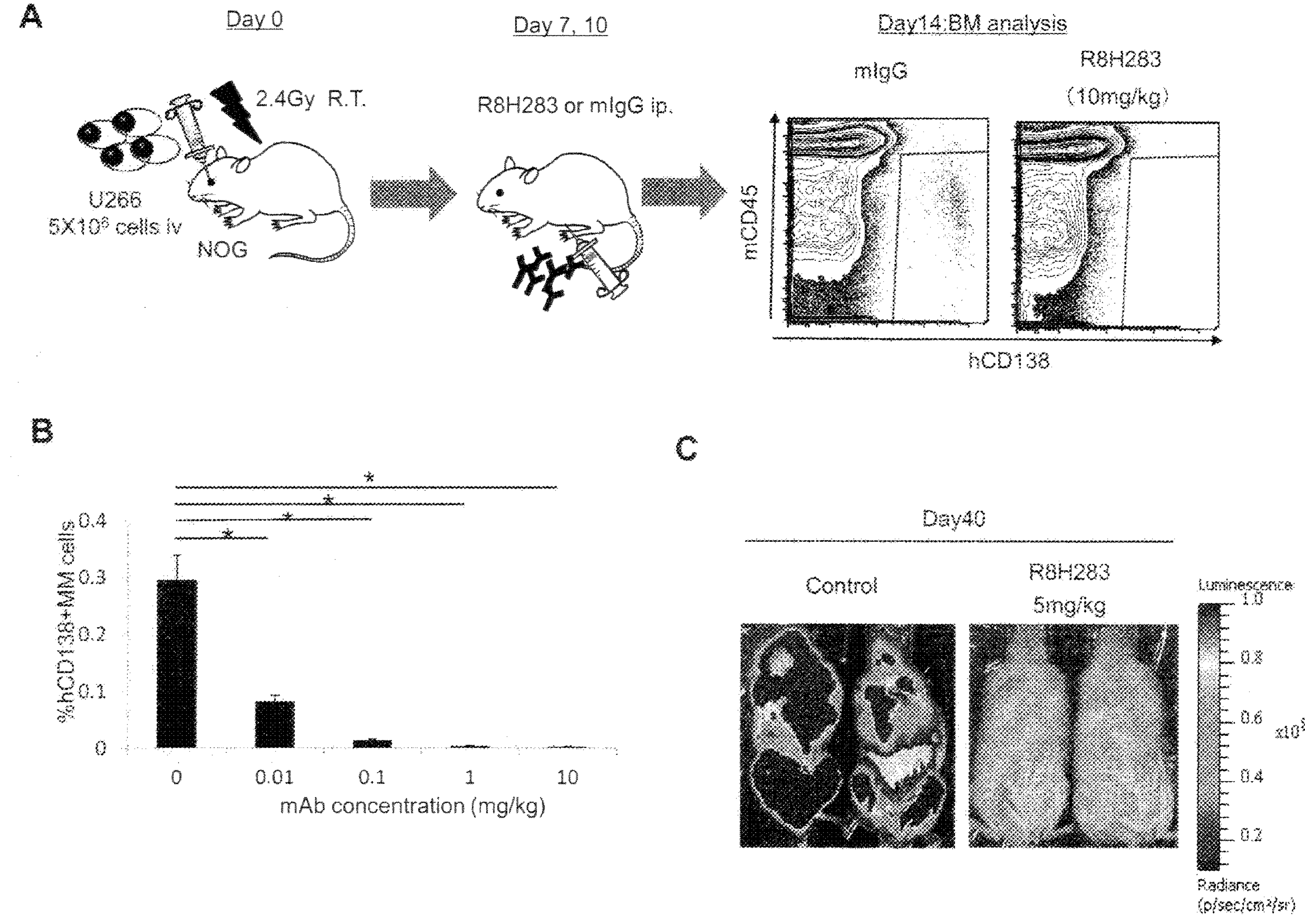
FIG. 18 shows (A) an experiment design for confirming the therapeutic effect of the R8H283 antibody on myeloma cell line U266 transplanted into a NOG mouse through the venous circulation (left) and an example of the results of bone marrow analysis on day 14 (right).

To examine the effect on myeloma cells under a more physiological environment, the effect of an antibody on myeloma cells transferred through the venous circulation and engrafted in a bone marrow was examined. $5\times10^6$ cells of myeloma cell line U266 to which a luciferase expression vector had been introduced were transplanted into a vein of NOD/SCIDγC−/−(NOG) mice that had been exposed to radiation of 2.4 Gy. After 7 days and 10 days, the R8H283 antibody or control IgG was administered intraperitoneally into the mice. To examine the effect of the antibodies, the chimerism of the human myeloma cells in mouse bone marrows was analyzed on day 14. While engraftment of CD138+U266 cells in bone marrows was clearly observed in every mouse of the group administered with the control IgG antibody, myeloma cells were found to have disappeared in the group of mice administered with the R8H283 antibody in both doses of 10 mg/kg and 1 mg/kg. Surprisingly, even in an extremely low dose of 0.01 mg/kg, the number of U266 cells in the bone marrow was significantly decreased (FIGS. 18A and 18B). Additionally, in the experiment in which an antibody was administered in a dose of 5 mg/kg, the mice were not analyzed on day 14, but subjected to tumor imaging on day 40 using IVIS. While tumor spreading was observed throughout the entire body of the mice in the group administered with the control IgG, no tumor was detected in the group administered with R8H283, indicating that the tumor appeared to have been cured (FIG. 18C). These results revealed that the R8H283 monoclonal antibody (R8H283) and antibodies that recognize an epitope identical to that for R8H283 have potent cytotoxic activity against myeloma cells expressing CD98hc.

14. Inhibition Effect on Myeloma Cell Growth by Anti-human CD98hc Monoclonal Antibody Having Cytotoxic Activity in Vivo (Bone Marrow Transplant Model)

Figure 19:
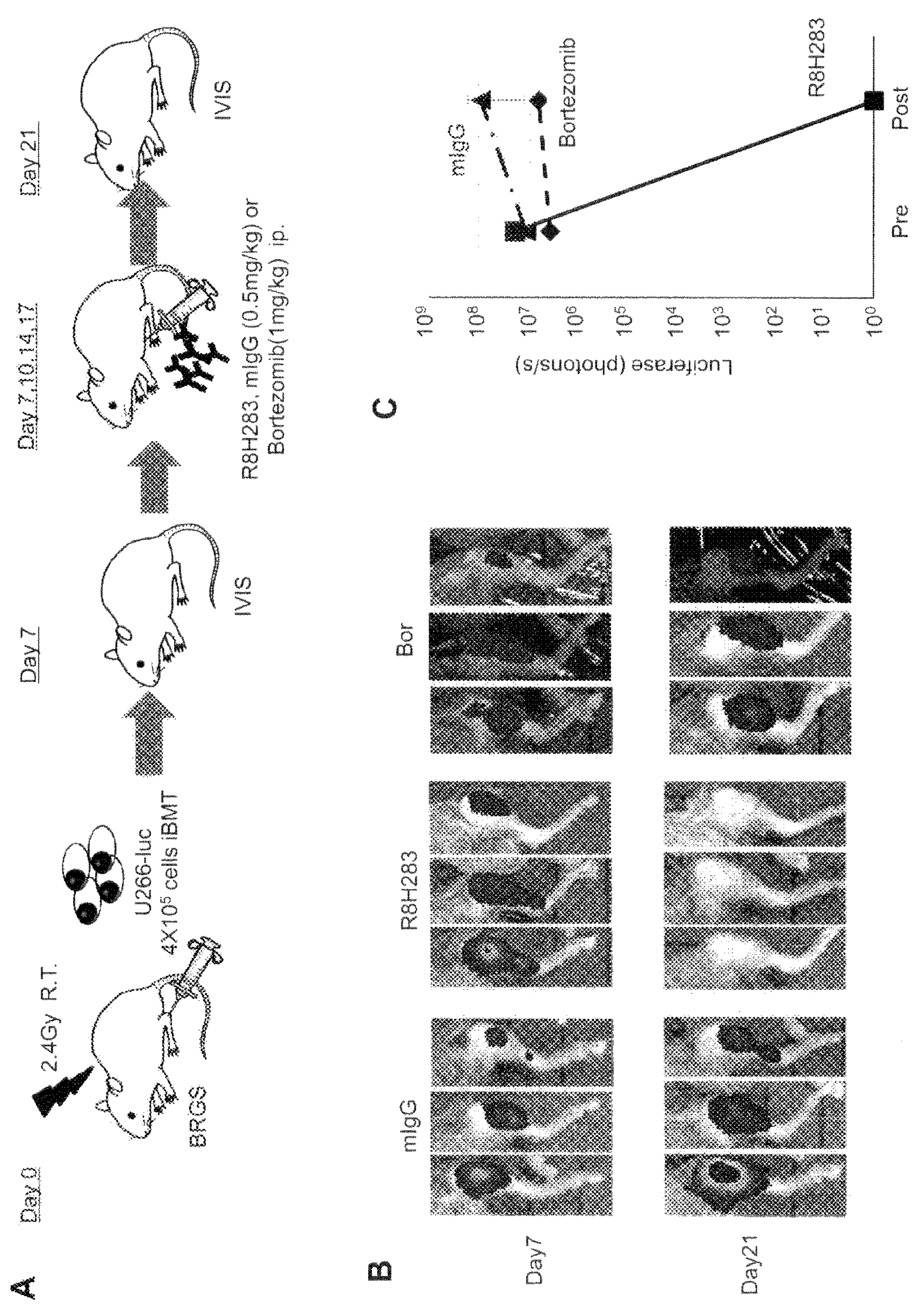
FIG. 19 shows (A) a treatment experiment design for confirming the therapeutic effect of the R8H283 antibody on myeloma cell line U266 transplanted into a BRGS-mouse bone marrow and (B) the results of the tumor volume in the bone marrow before and after the administration of the antibody or bortezomib (Bor) detected by luciferase expression.

In most cases, myeloma cells are a tumor that grows only in the bone marrow and are considered to receive great survival support from the bone marrow microenvironment. To further examine the effect on myeloma cells under a physiological environment, myeloma cells were directly transplanted into the bone marrow, and the effect of an antibody on a large amount of myeloma cells engrafted in the bone marrow was examined. $4\times10^5$ cells of myeloma cell line U266 to which a luciferase expression vector had been introduced were transplanted into the tibia bone marrow of B6-Rag2−/−γc−/−sirpa (BRGS) mice that had been exposed to radiation of 2.4 Gy. After 7 days, U266 cells expressing luciferase were confirmed to have engrafted in the tibia bone marrow by an IVIS. Thereafter, on days 7, 10, 14, and 17, the mice were intraperitoneally administered with the R8H283 antibody or control IgG in a dose of 0.5 mg/kg, or with bortezomib in a dose of 1 mg/kg. To examine the effect of the antibodies and bortezomib, luciferase expression imaging was performed with an IVIS on day 21. While U266 cells expressing luciferase were detected in the group administered with the control IgG and the group administered with bortezomib, no tumor was detected in the group administered with the R8H283 antibody (FIG. 19). These results revealed that the R8H283 monoclonal antibody (R8H283) and antibodies that recognize an epitope identical to the epitope for R8H283 have potent cytotoxic activity against myeloma cells expressing CD98hc, even when the myeloma cells are present in the bone marrow.

15. Analysis of Epitope

The results of the examination on the epitope for the R8H283 antibody in section 9 above were further examined in more detail. Expression vectors for 6 types of human/mouse chimera CD98hc proteins shown in FIG. 20 were prepared and introduced into CHO cells by lipofection. After 48 hours, the presence or absence of the binding of the R8H283 antibody was analyzed by FACS.

Figure 20:
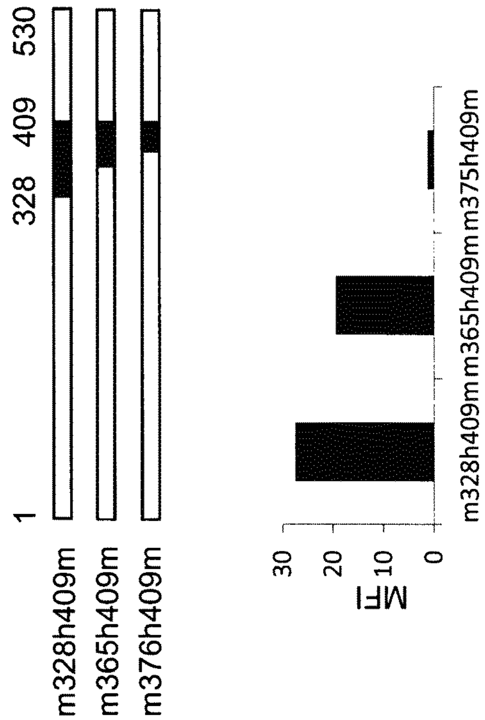
FIG. 20 shows the structures of human/mouse chimera CD98hc on the upper side. "m328h427" means that the amino acid residues at positions 328 to 427 of CD98hc are amino acid residues of human-originated CD98hc, and that the remaining amino acid residues are those of mouse origin. The same applies to the other chimera CD98hc.
Figure 20:
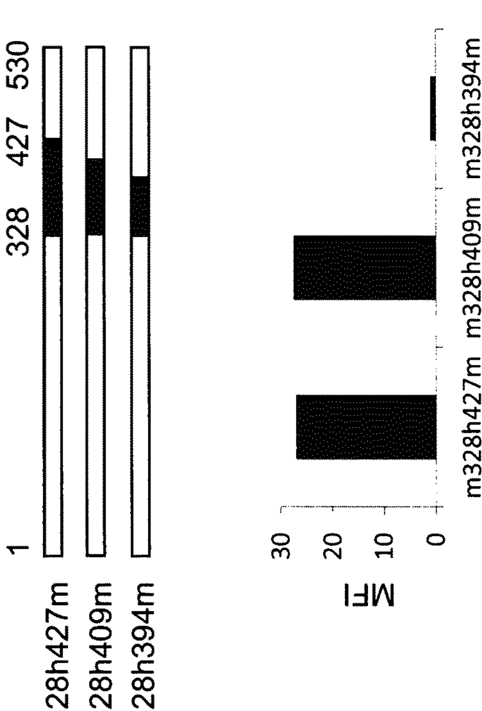
Figure 21:
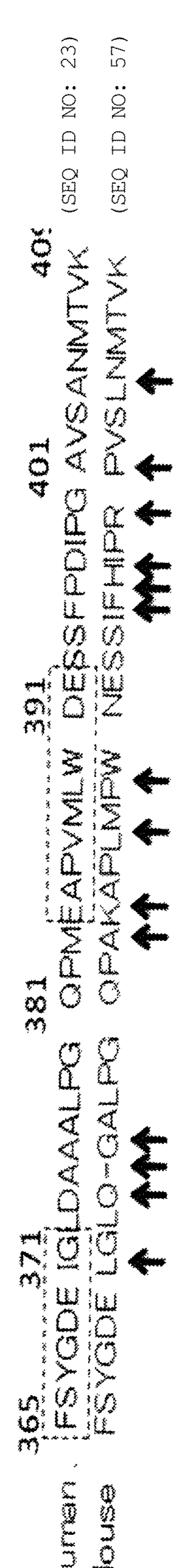
FIG. 21 shows the amino acid sequences at positions 365 to 409 of human CD98hc and mouse CD98hc. The regions surrounded by a dotted line indicate that when the amino acid residues in these regions are replaced by mouse-originated amino acid residues, the R8H283 antibody will not bind to these sequences. The amino acid residues indicated by arrows are those that differ between human CD98hc and mouse CD98hc.

The results confirmed that replacement of the region of the amino acid residues at positions 365 to 376 or 395 to 409 on CD98hc protein by the mouse-originated amino acid residues causes the R8H283 antibody to not bind to the CD98hc protein (FIG. 20). As shown in FIG. 21, amino acid residues that differ between human-originated CD98hc and mouse-originated CD98hc in a fragment composed of the amino acid residues at positions 365 to 409 of CD98hc protein are 15 amino acid residues at positions 371, 374, 375, 376, 383, 384, 387, 389, 391, 395, 396, 397, 400, 401, and 404. Thus, the results shown in FIG. 20 suggest that the R8H283 antibody recognizes the amino acid residues at positions 371, 374, 375, 376, 395, 396, 397, 400, 401, and/or 404.

Thus, vectors that express 7 types of variants (I371L, D374/A375Q, A376G, D391N/F395I/P396F/D397H, F395I/P396F/D397H, G400R/A401P, and A404L) were prepared by replacing the amino acid residues at positions 1 to 4 of human CD98hc by the mouse-originated amino acid sequences and introduced into CHO cells by lipofection. The expression vectors for the 7 types of CD98hc variant proteins were prepared using a Primestar mutagenesis basal kit (Takara Bio Inc.). The sequences of the primers used and DNAs used as templates are as shown below.

TABLE 6

| Construct | Primer1 | Primer2 | Template DNA |
|---|---|---|---|
| I371L | GG GAT GAG TTA GGC CTG GAT GCA GCT G CC (SEQ ID NO: 43) | G GCC TAA CTC ATC CCC GTA GCT GAA (SEQ ID NO: 44) | MSCV-hCD98hc-IRES-GFP |
| D374/A375Q | GGC CTG CAG GCT GC C CTT CCT GGA CAG (SEQ ID NO: 45) | GGC AGC CTG CAG GC C AAT CTC ATC CCC (SEQ ID NO: 46) | MSCV-hCD98hc-IRES-GFP |
| A376G | GAT GCA GGT GCC CT T CCT GGA CAG CCT (SEQ ID NO: 47) | AAG GGC ACC TGC AT C CAG GCC AAT CTC (SEQ ID NO: 48) | MSCV-hCD98hc-IRES-GFP |
| D391N/F395I/P396F/D397H | CTG TGG AAT GAG TC C AGC ATC TTT CAC (SEQ ID NO: 49) | GGA CTC ATT CCA CA G CAT GAC TGG AGC (SEQ ID NO: 50) | F395I/P396F/D397H |
| F395I/P396F/D397H | AGC TTA TTT CAC AT C CCA GGG GCT GTA AGT (SEQ ID NO: 51) | GAT GTG AAA TAA GC T GGA CTC ATC CCA CAG (SEQ ID NO: 52) | MSCV-hCD98hc-IRES-GFP |
| G400R/A401P | TC CCA AGG CCT GTA AGT GCC AAC ATG A CT (SEQ ID NO: 53) | T TAC AGG CCT TGG GAT GTC AGG GAA GC T (SEQ ID NO: 54) | MSCV-hCD98hc-IRES-GFP |
| A404L | GTA AGT CTC AAC AT G ACT GTG AAG GGC (SEQ ID NO: 55) | CAT GTT GAG ACT TA C AGC CCC TGG GAT (SEQ ID NO: 56) | MSCV-hCD98hc-IRES-GFP |

Figure 22:
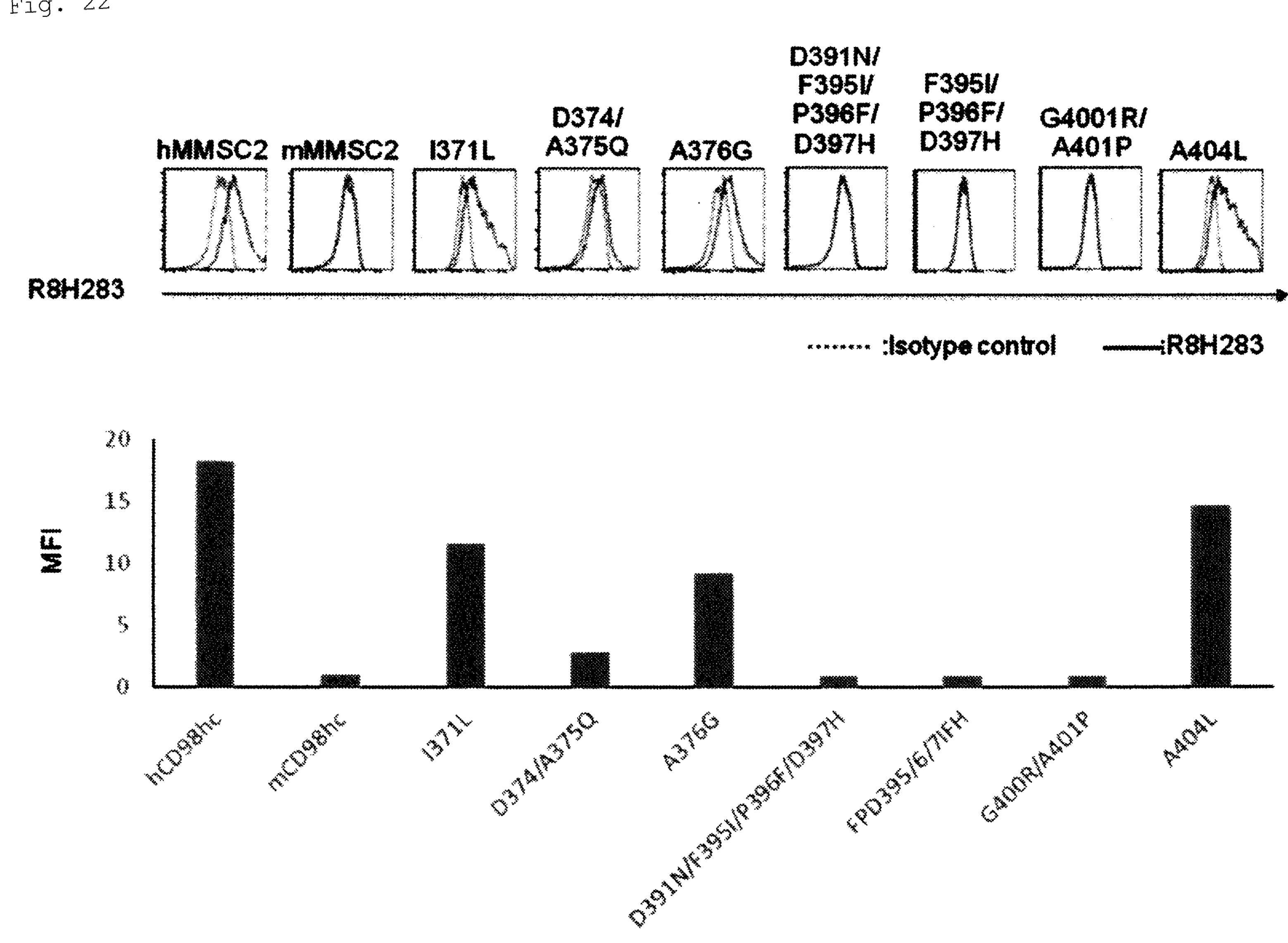
FIG. 22 shows the bond strength of the R8H283 antibody to 293T-cells expressing human CD98hc, mouse CD98hc, or 7 types of human CD98hc variants. The charts on the upper side show the results of flow cytometry and the chart on the lower side graphically shows MFI.

For the control, human CD98hc and mouse CD98hc were also expressed in CHO cells. Whether the binding of the R8H283 antibody to these cells is present was analyzed by FACS. As shown in FIG. 22, the results indicated that the R8H283 antibody does not bind to D391N/F395I/P396F/D397H, F395I/P396F/D397H, and G400R/A401P (i.e., in the measurement of fluorescent intensity by flow cytometry, the ratio of the fluorescent intensity of an antibody to the isotype control (mouse-originated CD98hc) is less than 1.05 (mean fluorescent intensity or MFI)). These results indicate that the amino acids at positions 395 to 397 and the amino acids at positions 401 and 402 are essential for the R8H283 antibody to bind to CD98. Additionally, notable attenuation of R8H283 was observed in the D374/A375Q variant, indicating that the amino acids at positions 374 and 375 also contribute to the binding of R8H283.

Sequence List

PCT_antibody_20160809_143516_6.txt

What is claimed is:

1. An anti-human CD98hc scFv comprising: a heavy chain variable region having the amino acid sequence set forth in SEQ ID NO: 4, and a light chain variable region having the amino acid sequence set forth in SEQ ID NO: 9.

2. A chimeric antigen receptor comprising the anti-human CD98hc scFv of claim 1.

3. The chimeric antigen receptor of claim 2, which is a monospecific chimeric antigen receptor or a multispecific chimeric antigen receptor.

4. A cell comprising the chimeric antigen receptor of claim 2.

5. The cell according to claim 4, wherein the cell is a T cell or a NK cell.

6. A pharmaceutical composition comprising the cell of claim 4.

7. A method of treating cancer, comprising administering the cell of claim 4 to a subject in need thereof.

8. The method of claim 7, wherein the dose is from $10^4$ cells/kg to $10^9$ cells/kg.

* * * * *